US011319356B2

(12) United States Patent
Behrens et al.

(10) Patent No.: US 11,319,356 B2
(45) **Date of Patent: *May 3, 2022**

(54) INTERFERON ALPHA 2B VARIANTS

(71) Applicant: Teva Pharmaceuticals Australia PTY LTD., Macquarie Park (AU)

(72) Inventors: Collette Behrens, Macquarie Park (AU); Anthony Doyle, Macquarie Park (AU); Adam Clarke, Macquarie Park (AU); Matthew Pollard, Macquarie Park (AU); Teresa Domagala, Macquarie Park (AU)

(73) Assignee: Teva Pharmaceuticals Australia Pty Ltd, Macquarie Park (AU)

( * ) Notice: Subject to any disclaimer, the term of this patent is extended or adjusted under 35 U.S.C. 154(b) by 92 days.

This patent is subject to a terminal disclaimer.

(21) Appl. No.: 16/710,574

(22) Filed: Dec. 11, 2019

(65) Prior Publication Data

US 2020/0102364 A1 Apr. 2, 2020

Related U.S. Application Data

(62) Division of application No. 14/921,420, filed on Oct. 23, 2015, now Pat. No. 10,544,199.

(30) Foreign Application Priority Data

Oct. 29, 2014 (AU) ................................ 2014904326

(51) Int. Cl.

| | |
|---|---|
| ***C07K 14/56*** | (2006.01) |
| ***C07K 16/28*** | (2006.01) |
| ***A61K 39/00*** | (2006.01) |
| ***A61K 39/395*** | (2006.01) |

(52) U.S. Cl.

CPC .......... *C07K 14/56* (2013.01); *C07K 16/2833* (2013.01); *C07K 16/2896* (2013.01); *C07K 2319/33* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 4,908,431 | A | 3/1990 | Colman et al. |
| 5,055,289 | A | 10/1991 | Frincke et al. |
| 5,225,539 | A | 7/1993 | Winter |
| 5,441,734 | A | 8/1995 | Reichert et al. |
| 5,545,405 | A | 8/1996 | Page |
| 5,558,864 | A | 9/1996 | Bendig et al. |
| 5,565,332 | A | 10/1996 | Hoogenboom et al. |
| 5,585,089 | A | 12/1996 | Queen et al. |
| 5,650,150 | A | 7/1997 | Gillies |
| 5,677,171 | A | 10/1997 | Hudziak |
| 5,693,761 | A | 12/1997 | Queen et al. |
| 5,770,195 | A | 6/1998 | Hudziak |
| 5,772,997 | A | 6/1998 | Hudziak |
| 5,795,965 | A | 8/1998 | Tsuchiya et al. |
| 5,837,821 | A | 11/1998 | Wu |
| 5,840,299 | A | 11/1998 | Bendig et al. |
| 5,844,093 | A | 12/1998 | Kettleborough et al. |
| 5,976,531 | A | 11/1999 | Mezes et al. |
| 5,977,322 | A | 11/1999 | Marks et al. |
| 6,054,297 | A | 4/2000 | Carter et al. |
| 6,180,370 | B1 | 1/2001 | Queen et al. |
| 6,217,866 | B1 | 4/2001 | Sela et al. |
| 6,248,516 | B1 | 6/2001 | Winter et al. |
| 6,277,375 | B1 | 8/2001 | Ward |
| 6,300,064 | B1 | 10/2001 | Knappik et al. |
| 6,339,070 | B1 | 1/2002 | Emery et al. |
| 6,417,337 | B1 | 7/2002 | Anderson et al. |
| 6,512,097 | B1 | 1/2003 | Marks et al. |
| 6,569,430 | B1 | 5/2003 | Waldmann et al. |
| 6,602,684 | B1 | 8/2003 | Umana et al. |
| 6,800,735 | B2 | 10/2004 | Whitty et al. |
| 6,821,505 | B2 | 11/2004 | Ward |
| 6,872,392 | B2 | 3/2005 | Nakamura et al. |
| 6,872,568 | B1 | 3/2005 | Ni et al. |
| 6,903,203 | B2 | 6/2005 | Copley et al. |
| 7,083,784 | B2 | 8/2006 | Dall et al. |
| 7,091,321 | B2 | 8/2006 | Gillies et al. |

(Continued)

FOREIGN PATENT DOCUMENTS

| | | |
|---|---|---|
| CN | 101045156 A | 10/2007 |
| CN | 103118706 A | 5/2013 |

(Continued)

OTHER PUBLICATIONS

Vijayasaradhi et al., "The Melanoma Antigen gp75 is the Human Homologue of the Mouse b (Brown) Locus Gene Product", J. Exp. Med., vol. 171, Apr. 1990, pp. 1375-1380.

Wahl et al., "The Anti-CD30 Monoclonal Antibody SGN-30 Promotes Growth Arrest and DNA Fragmentation in Vitro and Afects Antbumor Activity in Models of Hodgkin's Disease", Can. Res. vol. 62, Jul. 2002, pp. 3736-3742.

Ward et al., "Binding Activities of a Repertoire of Single Immunoglobulin variable domains secreted from *Escherichia coli*", Nature, Oct. 1989, 341, 544-546.

Wells, "Additivity of Mutational Effects in Proteins", Biochemistry, vol. 29, No. 37, Sep. 18, 1990, pp. 8509-8517.

Xuan et al., "Targeted delivery of interferon-a via fusion to anti-CD20 results in potent antitumor activity against B-cell lymphoma", Blood, 2010, 115, 2864-2871.

(Continued)

*Primary Examiner* — Gary B Nickol

*Assistant Examiner* — Jegatheesan Seharaseyon

(74) *Attorney, Agent, or Firm* — BakerHostetler

(57) ABSTRACT

The present invention provides a fusion polypeptide comprising a first domain and a second domain, wherein the first domain comprises a polypeptide ligand which binds to a cell surface-associated antigen and the second domain comprises aglycosylated interferon α 2b (IFNα2b) having a sequence of SEQ ID NO: 1 or SEQ ID NO: 2. The aglycosylated IFNα2b further comprises one or more amino acid substitutions or deletions which attenuate the activity of the aglycosylated IFNα2b.

18 Claims, 29 Drawing Sheets

Specification includes a Sequence Listing.

(56) References Cited

U.S. PATENT DOCUMENTS

| | | | |
|---|---|---|---|
| 7,166,697 | B1 | 1/2007 | Galanis et al. |
| 7,202,346 | B2 | 4/2007 | Payne et al. |
| 7,217,797 | B2 | 5/2007 | Hinton et al. |
| 7,252,994 | B2 | 8/2007 | Chuntharapai et al. |
| 7,312,318 | B2 | 12/2007 | Hansen et al. |
| 7,317,089 | B2 | 1/2008 | Kikly |
| 7,326,681 | B2 | 2/2008 | Gerngross |
| 7,355,015 | B1 | 4/2008 | Dickson et al. |
| 7,371,819 | B2 | 5/2008 | Escary |
| 7,388,081 | B2 | 6/2008 | Seki et al. |
| 7,456,257 | B2 | 11/2008 | Jones et al. |
| 7,521,047 | B2 | 4/2009 | Nagy et al. |
| 7,566,771 | B1 | 7/2009 | Adair et al. |
| 7,666,422 | B2 | 2/2010 | Siegall et al. |
| 7,670,595 | B2 | 3/2010 | Gillies et al. |
| 7,700,742 | B2 | 4/2010 | Cohen et al. |
| 7,709,610 | B2 | 5/2010 | Williams et al. |
| 7,723,485 | B2 | 5/2010 | Junutula et al. |
| 7,732,572 | B2 | 6/2010 | Cox, III |
| 7,732,578 | B2 | 6/2010 | Foote |
| 7,776,330 | B2 | 8/2010 | Yazaki et al. |
| 7,790,415 | B2 | 9/2010 | Gillies et al. |
| 7,829,673 | B2 | 11/2010 | De et al. |
| 7,919,078 | B2 | 4/2011 | Schreiber et al. |
| 7,943,744 | B2 | 5/2011 | Frendeus et al. |
| 8,039,593 | B2 | 10/2011 | Kuan et al. |
| 8,088,896 | B2 | 1/2012 | Fesar et al. |
| 8,119,775 | B2 | 2/2012 | Moretta et al. |
| 8,124,738 | B2 | 2/2012 | Terret et al. |
| 8,153,765 | B2 | 4/2012 | Park et al. |
| 8,187,601 | B2 | 5/2012 | Weng et al. |
| 8,980,267 | B2 | 3/2015 | Grewal et al. |
| 9,139,634 | B2 | 9/2015 | Morrison et al. |
| 9,611,322 | B2 | 4/2017 | Wilson et al. |
| 9,636,334 | B2 * | 5/2017 | Pogue ................ A61K 47/6813 |
| 9,963,515 | B2 | 5/2018 | Clarke et al. |
| 10,232,041 | B2 * | 3/2019 | Pogue ................ C07K 16/3061 |
| 10,544,199 | B2 * | 1/2020 | Behrens .................. A61P 35/00 |
| 2002/0142358 | A1 | 10/2002 | Mikayama et al. |
| 2002/0164788 | A1 | 11/2002 | Ellis et al. |
| 2002/0193569 | A1 | 12/2002 | Hanna |
| 2003/0211100 | A1 | 11/2003 | Bedian et al. |
| 2003/0211553 | A1 | 11/2003 | Logtenberg et al. |
| 2004/0006215 | A1 | 1/2004 | Keler et al. |
| 2004/0071696 | A1 | 4/2004 | Adams et al. |
| 2006/0083736 | A1 | 4/2006 | Law et al. |
| 2006/0099205 | A1 | 5/2006 | Adams et al. |
| 2006/0269516 | A1 | 11/2006 | Presta et al. |
| 2007/0098718 | A1 | 5/2007 | Long et al. |
| 2007/0190068 | A1 | 8/2007 | Hart et al. |
| 2008/0166319 | A1 | 7/2008 | Schreiber et al. |
| 2008/0166352 | A1 | 7/2008 | Siu et al. |
| 2009/0006815 | A1 | 1/2009 | Loubier |
| 2009/0068175 | A1 | 3/2009 | Lazar et al. |
| 2009/0076249 | A1 | 3/2009 | De et al. |
| 2009/0092599 | A1 | 4/2009 | Lazar et al. |
| 2009/0123950 | A1 | 5/2009 | Tesar |
| 2009/0142340 | A1 | 6/2009 | Lazar et al. |
| 2009/0148449 | A1 | 6/2009 | De Weers et al. |
| 2009/0175863 | A1 | 7/2009 | Kraus et al. |
| 2009/0202568 | A1 | 8/2009 | Eriksson et al. |
| 2009/0304710 | A1 | 12/2009 | Park et al. |
| 2010/0092489 | A1 | 4/2010 | Van De Winkel et al. |
| 2010/0104557 | A1 | 4/2010 | Bernett et al. |
| 2010/0172868 | A1 | 7/2010 | Morrison et al. |
| 2010/0189689 | A1 | 7/2010 | Chang et al. |
| 2010/0189729 | A1 | 7/2010 | Hoerr et al. |
| 2010/0285004 | A1 | 11/2010 | Tesar et al. |
| 2010/0297076 | A1 | 11/2010 | Morrison et al. |
| 2011/0104112 | A1 | 5/2011 | Morrison et al. |
| 2012/0201827 | A1 | 8/2012 | Elias et al. |
| 2013/0230517 | A1 | 9/2013 | Grewal et al. |
| 2013/0302318 | A1 | 11/2013 | Rojkjaer et al. |
| 2014/0248238 | A1 | 9/2014 | Wilson et al. |
| 2015/0031395 | A1 | 1/2015 | Wachter et al. |
| 2015/0203560 | A1 | 7/2015 | Grewal et al. |
| 2015/0313965 | A1 | 11/2015 | Pogue et al. |
| 2015/0353485 | A1 | 12/2015 | Hagen et al. |
| 2016/0068612 | A1 | 3/2016 | Clarke et al. |
| 2016/0122410 | A1 | 5/2016 | Behrens et al. |
| 2017/0202962 | A1 | 7/2017 | Pogue et al. |
| 2017/0233449 | A1 | 8/2017 | Wilson et al. |
| 2018/0305460 | A1 | 10/2018 | Clarke et al. |
| 2020/0102364 | A1 * | 4/2020 | Behrens ................. C07K 14/56 |

FOREIGN PATENT DOCUMENTS

| | | | |
|---|---|---|---|
| EP | 0706799 | A2 | 4/1996 |
| FR | 2905375 | A1 | 3/2008 |
| JP | 2003-535908 | | 12/2003 |
| JP | 2008-533977 | | 8/2008 |
| JP | 2009-501514 | A | 1/2009 |
| JP | 2010-504363 | | 2/2010 |
| JP | 2010-540453 | | 12/2010 |
| JP | 2013-542191 | | 11/2013 |
| JP | 2015-515453 | A | 5/2015 |
| JP | 2016-511712 | A | 4/2016 |
| JP | 6184965 | B2 | 8/2017 |
| JP | 6286532 | B2 | 2/2018 |
| WO | 90/05144 | A1 | 5/1990 |
| WO | 97/00271 | A1 | 1/1997 |
| WO | 97/24137 | A1 | 7/1997 |
| WO | 00/40265 | A1 | 7/2000 |
| WO | 00/42072 | A2 | 7/2000 |
| WO | 01/97844 | A1 | 12/2001 |
| WO | 2004/022593 | A2 | 3/2004 |
| WO | 2004/022747 | A1 | 3/2004 |
| WO | 2005/103083 | A2 | 11/2005 |
| WO | 2006/099875 | A1 | 9/2006 |
| WO | 2006/125640 | A2 | 11/2006 |
| WO | 2007/000769 | A2 | 1/2007 |
| WO | 2007/042309 | A2 | 4/2007 |
| WO | 2008/006554 | A2 | 1/2008 |
| WO | 2008/037257 | A2 | 4/2008 |
| WO | 2008/047242 | A2 | 4/2008 |
| WO | 2008/124086 | A2 | 10/2008 |
| WO | 2008/145139 | A1 | 12/2008 |
| WO | 2009/017823 | A2 | 2/2009 |
| WO | 2009/073975 | A1 | 6/2009 |
| WO | 2010/105290 | A1 | 9/2010 |
| WO | 2011/154453 | A1 | 12/2011 |
| WO | 2012/041800 | A1 | 4/2012 |
| WO | 2012/083370 | A1 | 6/2012 |
| WO | 2012/092612 | A1 | 7/2012 |
| WO | 2013/059885 | A2 | 5/2013 |
| WO | 2013/107791 | A1 | 7/2013 |
| WO | 2013/134138 | A1 | 9/2013 |
| WO | 2014/028502 | A1 | 2/2014 |
| WO | 2014/178820 | A1 | 11/2014 |

OTHER PUBLICATIONS

Yokota et al., "Rapid Tumor Penetration of a Single-Chain Fv and Comparison with other Immunoglobulin Forms", Can. Res., vol. 52, Jun. 1992, pp. 3402-3408.

Yoshinaga et al., "Ig L-chain Shuffling for Affinity Maturation of Phage Lobrary-derived Human Anti-human MCP-1 Antibody Blocking its Chemotactic Activity", J Biochem, 2008, 143, 593-601.

Yu et al., "Coexpression of Difference Antigenic Markers on Moieties that Bear CA 125 Determinants", Can. Res., vol. 51, Jan. 1991, pp. 468-475.

Hilkens et al., "Cell Membrane-Associated mucins and their adhesion-modulating property", Trends in Bio. Chem. Sci., Sep. 1992, 17, 359-363.

Hinton et al., "An Engineered Human IgG1 Antibody with Longer Serum Half-Life", J. Immunol., 2006, 176, 346-356.

Hinton et al., "Engineered Human IgG Antibodies with Longer Serum Half-Lives in Primates", J. Biol. Chem., Feb. 2004, 279(8), 6213-6216.

Holliger et al., "Diabodies: Small Bivalent and Bispecific Antibody Fragments", PNAS USA, Jul. 1993, 90, 6444-6448.

(56) References Cited

OTHER PUBLICATIONS

Honegger, et al., "Yet another numbering scheme for immunoglobulin variable domains: An automatic modeling and analysis tool", J. Mol. Biol., (2001) 309, 657-670.
Hoon et al., Molecular Cloning of a Human Monoclonal Antibody Reactive to Ganlioside Gm3 Antigen on Human Cancers, Can. Res. vol. 53, Nov. 1993, pp. 5244-5250.
Huang, T.-H. et al., J. Immunol., (2007), vol. 179, pp. 6881-6888.
Huston et al., "Protein Engineering of Antibody binding sites: Recovery of specific activity in an anti-digoxin single-chain Fv analogue produced in *Escherichia coli*", PNAS USA, Aug. 1988, 85, 5879-5883.
Ibrahim, et al., "CD38 Expression as an Important Prognostic Factor in B-Cell Chronic Lymphocytic Leukemia", Blood, vol. 98, No. 1, Jul. 2001, pp. 181-186.
Idusogie et al., "Engineered Antibodies with Increased Activity to Recruit Complement", J. Immunol., 2001, 166, 2571-2575.
Igawa, et al., "Engineering the variable region of therapeutic IgG antibodies", MABS, Landes Bioscience, US, vol. 3, No. 3, May 1, 2011, p. 243-252.
International Search Report and Written Opinion from related application PCT/AU2012/001323 dated Mar. 13, 2013.
International Search Report and Written Opinion from related application PCT/US2013/038659 dated Feb. 12, 2014.
International Search Report and Written Opinion issued in related application PCT/AU2015/050654 dated Dec. 3, 2015.
International Search Report and Written Opinion issued in related application PCT/IB2015/001600 dated Nov. 23, 2015.
International Search Report dated Nov. 23, 2015.
International Search Report dated Dec. 3, 2015.
Isreli, et al. Molecular Cloning of a Complementary DNA Encoding a Prostate-specific Membrane Antigen, Can. Res. vol. 53, Jan. 15, 1993, pp. 227-230.
J. P. Laubach et al.: "CD38-Targeted Immunochemotherapy in Refractory Multiple Myeloma: A New Horizon", Clinical Cancer Research, vol. 21, No. 12, Apr. 15, 2015, pp. 2660-2662.
Jones et al., "Selective Clearance of Glycoforms of a Complex Glycoprotein pharmaceutical caused by terminal N-acetylglucosamine is similar in humans and cynomolgus monkeys", Glycobiology, 2007, 17(5), 529-540.
Jorge Cortes et al: "Immune modulation of minimal residual disease in early chronic phase chronic myelogenous leukemia : A randomized trial of frontline high-dose imatinib mesylate with or without pegylated interferon alpha-2b and granulocyte-macrophage colony-stimulating factor", 1-15, Cancer., vol. 117, No. 3, Sep. 30, 2010, pp. 572-580.
Kalie, E. et al., J. Biol. Chem., (2007), vol. 282, No. 15, p. 11602-1161L.
Kanda et al., "Comparison of Biological Activity among nonfucosylated therapeutic IgG1 antibodies with three different N-linked Fc oligosaccharides: the high-mannose, hybrid, and complex types", Glycobiology, 2006, 17(1), 104-118.
Kaneko et al., "Anti-Inflammatory Activity of Immunoglobulin G. Resulting from Fc Sialylation", Science, Aug. 2006, 313, 670-673.
Kodama, et al., "Mutated SEA-D227 A-conjgated antibodies greatly enhance antitumor activity against MUC1-expressing bile duct carcinoma", Cancer Immunology, Immnotherapy, vol. 50, No. 10, Dec. 2001, pp. 539-548.
Koguma, T., et al., "Cloning and characterization of cDNA encoding rat ADP-ribosyl cyclase/cyclic ADP-ribose hydrolase (homologue to human CD38) from islets of Langerhans", Biochim. Biophys. Acta., 1994, 160-162.
Kolkman et al., "Directed Evolution of Proteins by Exon Shuffling", Nat. Biotechnol., May 2001, 19(5), 423-428.
Kopsidas et al., "In vitro Improvement of a Shark IgNAR antibody by QB replicase mutation and ribosome display mimics in vivo affinity maturation", Immunol Lett., Nov. 15, 2006, 107(2), 163-168.
Kossman et al., "A Phase I Trial of Humanized monoclonal Antibody HuM195 (anti-DC33) with Low-Dose Interleukin 2 in Acute Myelogenous Leukemia", Clin. Can Res., vol. 5, Oct. 1999, pp. 2748-2755.
Kotchev, et al., "Synergy of Interferons and Bortezomib: Advantages of Combination Treatments in Facilitating Apoptosis in Multiple Myeloma Cells", Cytokine, 2010, 88.
Ku, et al., "Alternate protein frameworks for molecular recognition", Proc. Natl. Acad. Sci. USA, vol. 92, Jul. 1995, pp. 6552-6556.
Labrijn et al. "Therapeutic IgG4 antibodies engage in Fab-arm exchange with endogenous human IgG4 in vivo", Nature Biotechnology, 2009, 27:8; 767-771.
Laubach, et al., "CD38-Targeted Immunochemotherapy in Refractory Multiple Myeloma: A New Horizon", Clinical Cancer Research, 2015, 2660-2663.
Laubach, et al., "Daratumumab granted breakthrough drug status", Expert Opinion on Investigational Drugs, vol. 23, No. 4, Feb. 2014, pp. 445-452.
Lesinski, et al., "IFN-a Bortezomib Overcome Bcl-2 and Mcl-1 Overexpression in Melanoma Cells by Stimulating the Extrinsic Pathway of Apoptosis", Cancer Res., Oct. 2008; 68:(20), pp. 8351-8360.
Li et al., "Optimization of Humanized IgGs in Glycoengineered Pichia Pastoris", Nat. Biotechnol., 2006, 24, 210-215.
Li et al., "The Epitope Specificity and Tissue Reactivity of Four Murine Monoclonal Anti-CD22 Antibodies", Cell Immunol., 1989, 111, 85-99.
Liu et al., "Crystal Structure of Human CD38 Extracellular Domain", Structure, 2005, 13, 1331-1339.
Livingston et al., "Improved Survival in Stage III Melanoma Patients with GM2 Antibodies: A Randomized Trail of Adjuvant Vaccination With GM2 Ganglioside" J. Clin. Oncol., 1994, 12, 1036-1044.
Loignon, et al., Stable high volumetric production of glycosylated human recombinant: IFNalpha2b in HEK293 cells, me Biotechnology, 2008, 8:65 doi:10.1186/1472-6750-8-65 (16 pages).
Maier, et al., "Requirements for the Internalization of a Murine Monoclonal Antibody Directed against the HER-2/neu Gene Product c-erB-2", Can Res., vol. 51, Oct. 1, 2991, pp. 5361-5369.
Malavasi et al., "CD38: A multi-lineage cell activation molecule with a split personality", Intl. J. Clin. Lab. Res., 1992, 22, 73-80.
Malavasi, et al., Human Immunology, Characterization of a Murine Monoclonal Antibody Specific for Human Early Lymphohemopoietic Cells ,1984, 9, 9-20.
Mason, et al., "Value of Monoclonal Anti-CD22 (p135) Antibodies for the Detection of Normal and Neoplastic B Lymphoid Cells", Blood, vol. 69, No. 3, Mar. 1987, pp. 836-840.
Matsui, et al., British Journal of Haematology, Anti-tumour activity of interferon-alpha in multiple myeloma: role of interleukin 6 and tumor cell differentiation 2003, 121, pp. 251-258.
Michaelsen et al., "Enhancement of Complement Activation and Cytolysis of Human IgG3 by Deletion of Hinge Exons", Scand. J. Immunol, 1990, 32, 517-528.
Millot, F., et al., "Results of a Phase II trial testing interferon-alpha 2b and cytarabine in children and adolescents with chronic myelogenous leukemia", Pediatric Blood and Cancer, 2006, 47, 555-559.
Mittelman et al., "Active Specific Immunotherapy in Patients with Melanoma", J. Clin. Invest, vol. 86, Dec. 1990, pp. 2136-2144.
Morabito, et al.,"Peripheral blood CD38 expression predicts time to progression in B-cell chronic lymphocytic leukemia after first-line therapy with high-does chlorambucil", Haematologica, vol. 87, No. 2, Feb. 2002, pp. 217-218.
Jiao, Y., et al. CD38: targeted therapy in multiple myeloma and therapeutic potential for solid cancers. Expert Opinion on Investigational Drugs., 2020, Sep. 2020, p. 1-14, published online ahead of print.
Mihara, K., et al. Activated T-cell-mediated immunotherapy with a chimeric receptor against CD38 in B-cell Non-Hodgkin lymphoma . J. Immunotherapy, 2009, 32:737-743.
A. Aviles et al: "Randomized clinical trial of zoledronic acid in multiple myeloma patients undergoing high-dose chemotherapy and stem-cell transplantation", Current Oncology, vol. 20, No. 1, Feb. 1, 2013, * the whole document *.

(56) References Cited

OTHER PUBLICATIONS

Al-Lazikani, B. et al., "Standard Conformations for the Canonical Structures of Immunoglobulins", Journal of Molecular Biology, 1997, 273, 927-948.
Alkan et al., "Antiviral and Antiproliferative Effects of Interferons Delivered via Monoclonal Antibodies", Journal of Interferon Research, 1984, vol. 4, No. 3, p. 355-363.
Ausiello, et al., "Functional topography of discrete domains of human CD38", Tissue Antigens, 2000, 56, 539-547.
Behr et al., "Low-Versus High-Dose Radioimmunotherapy with Humanized Anti-CD22 or Chimeric Anti-CD20 Antibodies in a Broad Spectrum of B Cell-associated Malignancies", Clin. Cancer Res., Oct. 1999, 5, 3304s-3314s.
Benhar, "Design of Synthetic Antibody Libraries", Expert Opin. Biol. Ther., May 2007, 7(5), 763-779.
Bhattacharya-Chatterjee et al., "Idiotype Vaccines against human T cell leukemia. II. Generation and Characterization of a Monoclonal idiotype cascade (Ab1, Ab2, and Ab3)", J. Immunol., 1988, 141, 1398-1403.
Bird et al., "Single-Chain Antigen-Binding Proteins", Science, Oct. 1988, 242, 423-426.
Bonardi, et al. "Delivery of Saporin to Human B-Cell Lymphoma Using Bispecific Antibody: Targeting via DC22 but not CD19, CD37 or Immunoglobulin Results in Efficient Killing", Can Res., vol. 53, Jul. 1991, pp. 3015-3021.
Bork, "Powers and Pitfalls in Sequence Analysis: The 70% Hurdle", Genome Research, 2000, 10:398-400.
Bork, et al., "Go hunting in sequence databases but watch out for the traps", Trends in Genetics, 1996, 12, 425-427.
Brekke et al., "Human IgG3 Can Adopt the Disulfuide bond pattern characteristic for IgG1 without resembling it in complement mediated cell lysis", Mol. Immuol., May 1993, 30, 1419-1425.
Bumal et al., "Characterization of the Human Tumor and Normal Tissue Reactivity of the KS1/4 Monoclonal Antibody", Hybridoma, 1988, 7(4), 407-415.
Camploi et al., "Human High Molecular Weight-Melanoma-Associated Antigen (HMW-MAA): A Melanoma Cell Surface Chondroitin Sulfate Proteoglycan (MSCP) with Biological and Clinical Significance", Crit. Rev. Immunol., 2004, 24(4), 267-296.
CD38-Targeted Immunochemotherapy in Refractory Multiple Myeloma: A New Horizon, Jacob P. Laubach and Paul G. Richardson, 2660-2663.
Chothia, et al., "Canonical Structures for the Hypervariable Regions of Immunoglobulins", J. Mol. Biol., (1987), No. 196, pp. 901-917.
Chothia, et al., "Conformations of immunoglobulin hypervariable regions", Nature, vol. 342, Dec. 1989, pp. 877-883.
Cortes, J. et al., "Immune modulation of minimal residual disease in early chronic phase chronic myelogenous leukemia : A randomized trial of frontline high-dose imatinib mesylate with or without pegylated interferon alpha-2b and granulocyte-macrophage colony-stimulatin factor", Cancer., 2010, 117, 572-580.
Crowder et al., Neoplasia, PML mediates IFN-a-induced apoptosis in myeloma by regulating TRAIL induction, 2005, pp. 1280-1287.
Dall'Acqua et al., "Increasing the Affinity of a Human IgG1 for the Neonatal Fc Receptor: Biological Consequences", J. of Immunol., 2002, 169, 5171-5180.
Dall'Acqua et al., "Properties of Human IgG1s Engineered for Enhanced Binding to the Neonatal Fc Receptor (FcRn)", J. Biol. Chem., Aug. 2006, 281(33), 23514-23524.
Davies & Riechmann, "Camelising Human Antibody Fragments: NMR Studies on VH Domains", FEBS Letters, 1994, 339, 285-290.
De Weers, et al., "Daratumumab, a Novel Therapeutic Human CD38 Monoclonal Antibody, Induces Killing of Multiple Myeloma and other Hematological Tumors", J. Immunol., 2011, 186:1840-1848.
Deaglio et al., "CD38 at the Junction between prognostic marker and therapeutic target", Trends in Mol. Med., 2008, 14(5), 210-218.
Divgi et al., "Clinical Comparison of Radiolocalization of Two Monoclonal Antibodies (mAbs) Against the TAG-72 Antigen", Nucl. Med. Biol., 1994, 21(1), 9-15.
During et al., "CD438 Expression is an Important Prognostic Marker in Chronic Lymphocytic Leukaemia", Leuk. Res., 2002, 16, 30-35.
Edelman, et al., "The Covalent Structure of an Entire yG Immunoglobulin Molecule", Biochemistry, vol. 63, 1969, pp. 78-85.
Ellis, J.H. et al., J. Immunol., (1995), vol. 155, No. 2, pp. 925-937.
Estin et al., "Transfected Mouse Melanoma Lines That Express Various Levels of Human Melanoma-Associated Antigen p97", J. Natl. Cancer Instit., Mar. 1989, 81(6), 445-448.
Feizi, "Demonstration by Monoclonal Antibodies that carbohydrate structures of glycoproteins and glycolipids are onco-developmental antigens", Nature, Mar. 1985, 314(7), 53-57.
Ferrara et al., "Modulation of Therapeutic Antibody Effector Functions by Glycosylation Engineering: Influence of Golgi Enzyme Localization Domain and Co-Expression of Heterologous B1,4-N-acetylgucosaminyltransferase III and Golgi a-mannosidase II", Biotechnol. Bioeng., Apr. 2006, 93(5), 851-861.
Fishburn, "The Pharmacology of PEGylation: Balancing PD with PK to Generate Novel Therapeutics", J. Pharm. Sci., 2008, 97, 4167-4183.
Foon et al., "Murine Anti-Idiotype (Id) Monoclonal Antibody (mAb) induces specific humoral responses to carcino-embryonic antigen (CEA) in Colorectal Cancer (CRC) Patients", Proc. Am. Soc. Clin. Oncol., 1994, 13, 294.
Fomier et al., "Update on the Management of Advanced Breast Cancer", Oncology, 1999, 13, 647-658.
Francisco, et al., "Agonistic Properties and in Vivo Antitumor Activity of the Anti-CD40 Antibody SGN-14", Can. Res., vol. 60, Jun. 15, 2000, pp. 3225-3231.
Frankel et al., "Cell Surface Receptor-Targeted Therapy of Acute Myeloid Leukemia: A Review", Cancer Biother. Radiopharm, 2000, 15(5), 459-477.
Frederic Millot et al: "Results of a phase II trial testing interferon-alpha 2b and cytarabine in children and adolescents with chronic myelogenous leukemia", Pediatric Blood and Cancer, vol. 47, No. 5, Jan. 1, 2006 pp. 555-559.
Frey et al., Antibody-based Targeting of Interferon-Alpha to the Tumor Neovasculature: a Critical Evaluation; Royal Society of Chemistry, Integr. Biol., vol. 3, pp. 468-478, 2011.
Funaro et al., "CD38 Functions Are Regulated Through an Internalization Step", J. Immunol., 1998, 160, 2238-2247.
Gennaro, Ed., Remington's Pharmaceutical Sciences, 18th Edition, Mack Publishing Co., Easton, PA, 1990.
Ghasriani et al., "A Single N-Acetylgalactosamine Residue at Threonine 106 Modifies the Dynamics and Structure of Interferon a2a around the Glycosylation Site", JBC, Jan. 4, 2013, vol. 228, No. 1, pp. 247-254.
Ghetie, et al., Anti-CD19 Inhibits the Growth of Human B-Cell Tumor Lines in Vitro and of Daudi Cells in SCIO Mice by Inducing Cell Cycle Arrest, Blood, vol. 83, No. 5, Mar. 1994, pp. 1329-1336.
Giudicelli, et al., "IMGT, the international ImMunoGeneTics database", Nucleic Acids Research, 1997, vol. 25, No. 1, pp. 206-211.
H. Ludwig et al.: "Thaiidomide-dexamethasone compared with melphalan-prednisolone in elderly patients with multiple myeloma", Blood, vol. 113, No. 15, Oct. 27, 2008, pp. 3435-3442.
Hamers-Casteman, et al., Naturally Occurring Antibodies Devoid of Light Chains, Nature, vol. 363, Jun. 1993, pp. 446-448.
Harden et al., "Interieukin-6 Prevents Dexamethasone-induced myeloma cell death", Blood, 1994, 84, 3063-3070.
Hellstrom et al. "Monoclonal Mouse Antibodies Raised Against Human Lung Carcinoma" Can. Res., vol. 46, Aug. 1986, pp. 3917-3923.
Hellstrom et al., "Monoclonal Antibodies to Cell Surface Antigens Shared by Chemically Induced Mouse Bladder Carcinomas", Cancer Res., 1985, 45, 2210-2188.
Henttu et al., "cDNA Coding for the Entire Human Prostate Specific Antigen Shows High Homologies to the Human Tissue Kallikrein Genes", Biochem. Biophys. Res. Comm., 1989, 160(2), 903-910.
Herlyn et al., "Monoclonal Antibody Detection of a Circulating Tumor-Associates Antigen. I. Presence of Antigen in Sera of Patients with Colorectal, Gastric and Pancreatic Carcinoma", J. Clin. Immunol, 1982, 2(2), 135-140.

(56) References Cited

OTHER PUBLICATIONS

Natali et al., "Immunohistochemical Detection of Antigen in Human Primary and Metastatic Melanomas by the Monoclonal Antibody 140.240 and Its Possible Prognostic Significance", Cancer, 1987, 59, 55-63.
Natsume et al., "Engineered Antibodies of IgG1/IgG3 Mixed Isotype with Enhanced Cytotoxic Activities", Cancer Research, May 2008, 68(10), 3863-3872.
Ngo, et al., "Computational Complexity, Protein Structure Prediction, and the Levinthal Paradox", The Protein Folding Problem and Tertiary Structure Prediction, 1994, pp. 492-495.
Norderhaug et al., "Chimeric mouse human IgG3 antibodies with an IgG4-like hinge region induce complement-mediated lysis more efficiently than IgG3 with normal hinge", Eur. J. Immunol., 1991, 21, 2379-2384.
Ono et al., "The humanized anti-HM1.24 antibody effectively kills multiple myeloma cells by human effector cell-mediated cytotoxicity", Mol. Immuno., 1999, 36, 387-395.
Otsuki et al., "Human Myeloma Cell Apoptosis induced by interferon-a", Jul. 1998, 103, 518-529.
Ozzello, et al., "The use of natural interferon alpha conjugated to a monoclonal antibody anti mammary epithelial mucin (Mc5) for the treatment of human breast cancer xenograft", Breast Cancer Research and Treatment, 1993, 25, 265-276.
Padlan, et al., "Identification of specificity-determining residues in antibodies", FASEB Journal, vol. 9, Jan. 1995, pp. 133-139.
Pan, M. et al., Biochemistry, (2008), vol. 47, pp. 12018-12027, abstract.
Pavlinkova et al., "Radioimmunotherapy of Human Colon Cancer Xenografls Using a Dimeric Single-Chain Fv Antibody Construct", vol. 5, Sep. 1999, pp. 2613-2619.
Peled et al., "The Biochemistry of Somatic Hypermutation", Annu. Rev. Immunol., 2008, 26, 481-511.
Perez et al., "Isolation and Characterization of a cDNA encoding the KS1/4 epithelial carcinoma marker", J. Immumnol., 1990, 142, 3662-3667.
Peterson et al., Effect of Multiple, Repeated Doses of Radioimmunotherapy on Target Antigen Expression (Breast MUC-1 Mucin) in Breast Carcinomas, Can. Res. vol. 57, Mar. 1997, pp. 1103-1108.
Petkova et al., "Enhanced half-life of genetically engineered human IgG1 antibodies in a humanized FcRn Mouse model: Potential Application in Humorally mediated autoimmune disease", Immunol., 2006, 18(12), 1759-1769.
Piehler, et al., "New structural and functional aspects of the Type 1 interferon-receptor interaction revealed by comprehensive mutational analysis of the binding interface", vol. 275, No. 51, Dec. 2000, pp. 40425-40433.
Poljak, "Production and Structure of Diabodies", Structure, Dec. 1994, 2, 1121-1123.
Pollack et al., Treatment parameters Modulating Regression of Human Melanoma Xenografls by an Antibody-drug conjugate (CR011-vcMMAE) targeting GPNMB, Cancer Chemother Pharmacol, 60, pp. 423-435, 2007.
Queen et al., "A Humanized antibody that binds to the interleukin 2 receptor", PNAS, Dec. 1989, 86(24), 10029-10033.
Ragnhammar et al., "Effect of Monoclonal Antibody 17-1A and GM-CSF in patients with advanced colorectal carcinoma—long-lasting, complete remissions can be induced", Int. J. Cancer, 1993, 53, 751-758.
Randomized clinical trial of zoledronic acid in multiple myeloma patients undergoing high-dose chemotherapy and stem-cell transplantation, A. Aviles MD,* N Neri MD/, e13-20, 20/1.
Reff, et al., "Depletion of B Cells In Vivo by a Chimeric Mouse Human Monoclonal Antibody to CD20", Blood, vol. 83, No. 2, Jan. 15, 1994, pp. 435-445.
Results of a Phase II Trial Testing Interferon-Alpha 2b and Cytarabine Children and Adolescents With Chronic Myelogenous Leukemia, Frederic Millot, MD,, 555-559.
Richardson, et al., "Monoclonal Antibodies in the Treatment of Multiple Myeloma", British Journal of Haematology, 2011, 154:745-754.
Rosenblum, et al., "Recombinant Immunotoxins Directed against c-erb-3/HER2/neu Oncogene Product: In Vitro Cytotoxicity, Pharmacokinetics, and in Vivo Efficacy Studies in Xenograft Models", Clin. Can. Res., vol. 5, Apr. 1999, pp. 865-874.
Rossi et al., "CD20-Targeted Tetrameric Interferon-a, a novel and potent immunocytokine for the therapy of B-cell Tymphomas", Blood, Oct. 2009, vol. 114, No. 18, 3864-3871.
Rossi et al., "Preclinical Studies on Targeted Delivery of Multiple IFNa2b to HLA-DR in Diverse Hemotologic Cancers" Lymphoid Neoplasia, Blood Journal, vol. 118, No. 7, Aug. 18, 2011; 1877-1884.
Saleh et al., "Generation of a human anti-idiotypic antibody that mimics the GD2 antigen", J. Immunol., 1993, 151, 3390-3398.
Schier et al., "Isolation of High-Affinity Monomeric Human Anti-c-erbB-2 Single chain Fv Using Affinity-driven Selection", J. Mol. Biol., 1996, 255, 28-43.
Schier et al., "Isolation of Picomolar Affinity Anti-c-erbB-2 Single-Chain Fv by Molecular Evolution of the Complementarity Determining Regions in the Center of the Antibody Binding Site", J. Mol. Biol., 1996, 263, 551-567.
Sgouros, et al., "Modeling and Dosimetry of Monoclonal Antibody M195 (Anti-CD33) in Acute Myelogenous Leukemia", J. Nucl. Med., vol. 34, No. 3, Mar. 1993, pp. 422-430.
Shields et al., "High Resolution Mapping of the Binding Site on Human LgG1 for FcyRI, FcyRII, FcyRIII, and FcRn and Design of IgG1 Variants with Improved Binding to the FcyR", J. Biol. Chem., Mar. 2001, 276(9), 6591-6604.
Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", J. Biological Chemistry, vol. 278, No. 5, Jan. 2003, pp. 3466-3473.
Shitara et al., "A mouse/human chimeric anti-(ganglioside GD3) antibody with enhanced antitumor activities", Cancer Immunol. Immunother, 1993, 36, 373-380.
Sievers et al., "Selective Abiation of Acute Myeloid Leukemia Using Antibody-Targeted Chemotherapy: a Phase 1 Study of Anti-CD33 Calichaemicin Immunoconjugate", Blood, vol. 93, No. 11, Jun. 1999, pp. 3678-3784.
Stavenhagen et al., "Fc Optimization of Therapeutic Antibodies Enhances their ability to kill tumor cells in vitro and controls tumor expansion in vivo via low-affinity activating Fcy Receptors", Cancer Res., 2007, 67, 8882-8890.
Stewart, A.G. etal., DNA, (1987), vol. 6, No. 2, pp. 119-128, abstract; 123, Table 1.
Tailor et al., "Nucleotide Sequence of Human Prostatic Acid Phosphatase Determinded from a Full Length cDNA Clone" Nucleic Acids Research, vol. 18, No. 16, Jul. 1990, p. 4928.
Tan et al., "Influence of the hinge region on complement activation, C1q binding, and segmental flexibility in chimeric human immunoglobulins", PNAS, 1990, 87, 162-166.
Thalidomide-dexamethasone compared with melphalan-prednisolone in elderly patients with multiple myeloma, Heinz Ludwig, 1 Roman Hajek,2 Elena T6thova,3 Johannes Drach,4 Zdenek Adam,2 Boris Labar,5 Miklos Egyed,6, 3435-3442, 113/15.
Thie et al., "Affinity Maturation by Phage Display", Methods, Mol. Biol., 2009, 525, 309-322.
Thomas, C. etal., Cell, (Aug. 19, 2011), vol. 146, pp. 621-632.
Tomoyuki, et al., "Engineering the variable region of therapeutic IgG antibodies", MABS, Landes Bioscience, US, vol. 3, No. 3, May 1, 2011, p. 243-252.
Trail et al., "Cure of Xenografted Human Carcinomas by BR96-Doxorubicin Immunoconjugates", Science, 1993, 261, 212-215.
Trail et al., "Effect of Linker Variation on the Stability, Porency, and Efficacy of Carinoma-reactive BR64-Doxorubicin Immunoconjugates", Can Res., vol. 56, Nov. 1996, pp. 5179-5185.
Trail, et al., "Effect of Linker Variation on the Stability, Porency, and Efficacy of Carcinoma-reactive BR64-Doxorubicin Immunoconjugates", Can. Res., vol. 57, Jan. 1, 1997, pp. 100-105.

(56) References Cited

OTHER PUBLICATIONS

Trauth et al., "Monoclonal Antibody-Mediated Tumor Regression by Induction of Apoptosis", Science, Jul. 1989, 245, 301-304.
Trzpis, M. etal., Am. J. Pathol., (2007), vol. 171, No. 2, pp. 386-395.
Tse, et al., "CR011, a Fully Human Monoclonal Antibody-Auristatin E Conjugate, for the Treatment of Melanoma", Clin. Cancer Res., 2006, 12(4): 1373-1382.
Van Der Veer Michael S et al.: "Towards effective immunotherapy of myeloma: enhanced elimination of myeloma cells by combination of lenalidomide with the human CD38 monoclonal antibody daratumumab", Haematolo, Ferrata Storti Foundation, Italy, vol. 96, No. 2, Feb. 1, 2011 (Feb. 1, 2011), pp. 284-290.
Van Hof, et al., "Biodistribution of Indium-Labeled Engineered Human Antibody CTM01 in Ovarian Cancer Patients Influence of Protein Dose", Can. Res., vol. 56, Nov. 15, 1996, pp. 5179-5185.

* cited by examiner

A.

| | $IC_{50}$ (nM) |
|---|---|
| A10.21 IgG4 (S228P) IFN (A145D, T106T) | 0.15 |
| A10.21 IgG4 (S228P) IFN (A145D, T106A) | 0.12 |
| A10.21 IgG4 (S228P) IFN (A145D, ΔT106) | 0.06 |
| A10.21 IgG1 IFN (A145D, T106T) | 0.11 |
| A10.21 IgG1 IFN (A145D, T106A) | 0.02 |
| A10.21 IgG1 IFN (A145D, ΔT106) | 0.02 |

B.

| | $IC_{50}$ (nM) |
|---|---|
| A10.21 IgG4 (S228P) IFN (A145D, T106T) | 0.21 |
| A10.21 IgG4 (S228P) IFN (A145D, T106A) | 0.17 |
| A10.21 IgG4 (S228P) IFN (A145D, ΔT106) | 0.06 |
| A10.21 IgG1 IFN (A145D, T106T) | 0.19 |
| A10.21 IgG1 IFN (A145D, T106A) | 0.06 |
| A10.21 IgG1 IFN (A145D, ΔT106) | 0.04 |

| | $IC_{50}$ (pM) |
|---|---|
| R10A2 IgG4 (S228P) IFN (A145D, T106T) | 0.84 |
| R10A2 IgG4 (S228P) IFN (A145D, T106A) | 0.11 |
| R10A2 IgG4 (S228P) IFN (A145D, T106D) | 0.33 |
| R10A2 IgG4 (S228P) IFN (A145D, T106E) | 0.37 |

| | | $IC_{50}$ (pM) |
|---|---|---|
| -□- | R10A2 IgG4 (S228P) IFN (A145D, T106T) | 0.46 |
| -▲- | R10A2 IgG4 (S228P) IFN (A145D, T106F) | 0.06 |
| -▽- | R10A2 IgG4 (S228P) IFN (A145D, T106G) | 0.06 |
| -○· | R10A2 IgG4 (S228P) IFN (A145D, T106H) | 0.08 |
| -□- | R10A2 IgG4 (S228P) IFN (A145D, T106I) | 0.09 |

| | $IC_{50}$ (pM) |
|---|---|
| R10A2 IgG4 (S228P) IFN (A145D, T106T) | 0.57 |
| R10A2 IgG4 (S228P) IFN (A145D, T106K) | 0.07 |
| R10A2 IgG4 (S228P) IFN (A145D, T106L) | 0.05 |
| R10A2 IgG4 (S228P) IFN (A145D, T106M) | 0.08 |
| R10A2 IgG4 (S228P) IFN (A145D, T106N) | 0.09 |
| Intron A | 0.22 |

| | $IC_{50}$ (pM) |
|---|---|
| -□- R10A2 IgG4 (S228P) IFN (A145D, T106T) | 0.45 |
| -▲- R10A2 IgG4 (S228P) IFN (A145D, T106P) | 0.07 |
| -▽- R10A2 IgG4 (S228P) IFN (A145D, T106Q) | 0.06 |
| ·◆· R10A2 IgG4 (S228P) IFN (A145D, T106R) | 0.08 |
| -□- R10A2 IgG4 (S228P) IFN (A145D, T106S) | 0.10 |

A.

B.

A.

B.

| | $EC_{50}$ (nM) |
|---|---|
| A10.21 IgG4 (S228P) IFN (A145D, T106T) | >1000 |
| A10.21 IgG4 (S228P) IFN (A145D, T106A) | 160.6 |
| A10.21 IgG4 (S228P) IFN (A145D, ΔT106) | 202.8 |
| A10.21 IgG1 IFN (A145D, T106T) | >1000 |
| A10.21 IgG1 IFN (A145D, T106A) | 274.1 |
| A10.21 IgG1 IFN (A145D, ΔT106) | 200.2 |
| Intron A | $1.3e^{-3}$ |

| | $EC_{50}$ (nM) |
|---|---|
| Intron A | 0.01 |
| A10.43 IgG4 (S228P) IFN (A145D, T106T) | 230.7 |
| A10.43 IgG4 (S228P) IFN (A145D, T106A) | 145.2 |

INTERFERON ALPHA 2B VARIANTS

CROSS REFERENCE TO RELATED APPLICATIONS

This application is a divisional application of U.S. application Ser. No. 14/921,420, filed Oct. 23, 2015, which claims priority to Australian Patent Application No. 2014904326 filed on Oct. 29, 2014, the contents of each of which are incorporated by reference herein, in their entirety and for all purposes.

REFERENCE TO A SEQUENCE LISTING

This application includes a Sequence Listing submitted electronically as a text file named 101017.000014.txt, created on Feb. 1, 2022, with a size of 298 KB. The Sequence Listing is incorporated by reference herein.

FIELD OF INVENTION

The present invention relates to polypeptides comprising ligands targeted against cell surface antigens and aglycosylated interferon α 2b (IFNα2b) and the use of these polypeptides in the treatment of cancer.

BACKGROUND OF INVENTION

Numerous peptide and polypeptide molecules have been described to function by interacting with a receptor on a cell surface, and thereby stimulating, inhibiting, or otherwise modulating a biological response, usually involving signal transduction pathways inside the cell that bears the said receptor. Examples of such molecules include peptide and polypeptide hormones, cytokines, chemokines, growth factors, apoptosis-inducing factors and the like. These molecules can be either soluble or can be attached to the surface of another cell.

Due to the biological activity of such molecules, some have potential use as therapeutics. Several peptide or polypeptide molecules have been approved by regulatory agencies as therapeutic products, including, for example, human growth hormone, insulin, interferon IFNα2b, IFNα2a, IFNβ, erythropoietin, G-CSF and GM-CSF. Many of these and other peptides have demonstrated potential in therapeutic applications, but have also exhibited toxicity when administered to human patients. One reason for toxicity is that most of these molecules trigger receptors on a variety of cells, including cells other than those that mediate the therapeutic effect. For example, when IFNα2b is used to treat multiple myeloma its utility resides, at least in part, in its binding to type I interferon receptors on the myeloma cells, which in turn triggers reduced proliferation and hence limits disease progression. Unfortunately, however, this IFN also binds to numerous other, normal cells within the body, triggering a variety of other cellular responses, some of which are harmful (e.g. flu-like symptoms, neutropenia, depression). A consequence of such "off target" activity of peptides is that many peptides are not suitable as drug candidates. In this context, "off target activity" refers to activity on the peptide's natural receptor, but on the surface of cells other than those that mediate therapeutically beneficial effects.

Even though some peptides, such as IFNα2b, are approved for the treatment of medical conditions, they are poorly tolerated due to their "off target" biological activity. The off-target activity and associated poor tolerability also mean that some of these peptide based drugs cannot be administered at sufficiently high dosages to produce optimal therapeutic effects on the target cells which mediate the therapeutic effect.

Similarly, it has been known since the mid-1980's that interferons, in particular IFNα, are able to increase apoptosis and decrease proliferation of certain cancer cells. These biological activities are mediated by type I interferon receptors on the surface of the cancer cells which, when stimulated, initiate various signal transduction pathways leading to reduced proliferation and/or the induction of terminal differentiation or apoptosis. IFNα has been approved by the FDA for the treatment of several cancers including melanoma, renal cell carcinoma, B cell lymphoma, multiple myeloma, chronic myelogenous leukemia (CML) and hairy cell leukemia. A "direct" effect of IFNα on the tumour cells is mediated by the IFNα binding directly to the type I IFN receptor on those cells and stimulating apoptosis, terminal differentiation or reduced proliferation. One "indirect" effect of IFNα on non-cancer cells is to stimulate the immune system, which may produce an additional anti-cancer effect by causing the immune system to reject the tumour.

Unfortunately, the type I interferon receptor is also present on most non-cancerous cells. Activation of this receptor on such cells by IFNα causes the expression of numerous pro-inflammatory cytokines and chemokines, leading to toxicity. Such toxicity prevents the dosing of IFNα to a subject at levels that exert the maximum anti-proliferative and pro-apoptotic activity on the cancer cells.

Ozzello et al. (Breast Cancer Research and Treatment 25:265-76, 1993) described covalently attaching human IFNα to a tumour-targeting antibody, thereby localizing the direct inhibitory activity of IFNα to the tumour as a way of reducing tumour growth rates, and demonstrated that such conjugates have anti-tumour activity in a xenograft model of a human cancer. The mechanism of the observed anti-cancer activity was attributed to a direct effect of IFNα on the cancer cells, since the human IFNα used in the experiments did not interact appreciably with the murine type I IFN receptor, which could have lead to an indirect anti-cancer effect. Because of this lack of binding of the human IFNα to the murine cells, however, the authors could not evaluate the toxicity of the antibody-IFNα conjugate relative to free INFα. These authors used a chemical method to attach the IFNα to the antibody.

Alkan et al., (Journal of Interferon Research, volume 4, number 3, p. 355-63, 1984) demonstrated that attaching human IFNα to an antibody that binds to the Epstein-Barr virus (EBV) membrane antigen (MA) increased its antiproliferative activities towards cells that express the EBV-MA antigen. This increased potency was dependent on both antigen expression by the target cells and the binding specificity of the antibody. The cell line tested was the cancer cell line QIMR-WIL, a myeloblastic leukemia. The authors suggested that the attachment of IFNα to an antibody could be used as a treatment for cancer since it would reduce tumour growth. Alkan et al did not address the potential toxicity of these antibody-IFNα conjugates arising from their interactions with normal, antigen-negative cells.

It is also known that the linkage between an antibody and IFNα may be accomplished by making a fusion protein construct. For example, IDEC (WO01/97844) disclose a direct fusion of human IFNα to the C terminus of the heavy chain of an IgG targeting the tumour antigen CD20. Other groups have disclosed the use of various linkers between the C-terminus of an IgG heavy chain and the IFNα. For example, U.S. Pat. No. 7,456,257 discloses that the C-terminus of an antibody heavy chain constant region may be connected to IFNα via an intervening serine-glycine rich (S/G) linker of the sequence $(GGGGS)_n$ (SEQ ID NO: 113), where n may be 1, 2 or 3, and that there are no significant differences in the IFNα activity of the fusion protein construct regardless of linker length.

Morrison et al. (US2011/0104112 A1; and Xuan C, Steward K K, Timmerman J M, Morrison S L. Targeted delivery of interferon-α via fusion to anti-CD20 results in potent antitumor activity against B-cell lymphoma. Blood 2010; 115:2864-71) also disclose IFNα linked to the C-terminus of the heavy chain of a cancer-targeting IgG antibody, with an intervening S/G linker, and observed that the fusion of the IgG and linker to the IFNα reduced the activity of IFNα on cells that did not express the corresponding antigen on the cell surface. The decreased IFN activity of these fusion protein constructs was modest when compared to human non-fusion protein IFNα (free IFNα) acting on human cells, but appeared to be more significant for murine IFNα on murine cells. The decrease in the activity of human IFNα that results from fusing it to the C-terminus of an antibody, as observed by Morrison et al, and in U.S. Pat. No. 7,456,257 is modest and is generally considered to be a disadvantage since it reduces potency of the IFN. This disadvantage was pointed out, for example, by Rossi et al (Blood vol. 114, No. 18, pp3864-71), who used an alternative strategy of attaching the IFNα to a tumor targeting antibody in such a way that no loss in IFNα activity was observed.

In general the prior art teaches to use a potent IFN and to target this IFN to cancer cells. While this approach results in an increase in activity of the IFN against cancer cells, it does not address the issue of activity of the IFN on normal "off-target" cells. In prior art examples referred to above, the human IFNα portion of the antibody-IFNα fusion protein maintained a high proportion of native IFNα activity when exposed to human cells that do not express the corresponding antigen on their cell surfaces. This activity may lead to toxicity arising from the activation of non-cancerous, normal ("off target") cells by the IFNα portion of the fusion protein. Accordingly, there exists a need to decrease the "off-target" activity of IFN-based drugs, while retaining the "on-target", therapeutic effect of such drugs. The maintenance of target-specific activity and at the same time a reduction in non-target toxicity of these types of therapeutic agents would create a greater therapeutic concentration window for therapeutically useful peptides. It would for example be desirable to use human IFNα in a form such that its activity can be directed to the cancer cells while minimizing its effects on normal human cells. Ideally the type I interferon receptor on the cancer cells would be maximally stimulated, while the same receptor on non-cancerous cells would experience minimal stimulation. There is a need to target human IFNα to the cancer cells in such a way that it has dramatically more activity on the cancer cells, which display the antigen, than on the normal cells, which do not display the antigen. The same logic applies to other potentially therapeutic molecules, e.g. other cytokines, peptide and polypeptide hormones, chemokines, growth factors, apoptosis-inducing factors and the like.

The logic of this approach has been demonstrated in WO 2013/059885, and WO 2014/178820, the disclosure of each of which is incorporated herein by cross reference.

SUMMARY OF INVENTION

In a first aspect the present invention provides a fusion polypeptide comprising a first domain and a second domain, wherein the first domain comprises a polypeptide ligand which binds to a cell surface-associated antigen and the second domain comprises human aglycosylated interferon α 2b (IFNα2b) having a sequence of SEQ ID NO: 1 or SEQ ID NO: 2 and wherein the aglycosylated IFNα2b further comprises one or more amino acid substitutions or deletions which attenuate the activity of the aglycosylated IFNα2b.

In another aspect the present invention provides a fusion polypeptide comprising a sequence selected from the group consisting of SEQ ID NOs: 31, 61 to 77, 83 and 87, and a sequence selected from the group consisting of SEQ ID NOs: 81, 82 and 84.

In another aspect the present invention provides a fusion polypeptide comprising SEQ ID NO: 87 and SEQ ID NO: 81.

In another aspect the present invention provides a fusion polypeptide comprising SEQ ID NO: 79 and SEQ ID NO: 85.

In another aspect the present invention provides a fusion polypeptide comprising SEQ ID NO: 80 and SEQ ID NO: 86.

In another aspect the present invention provides a fusion polypeptide comprising SEQ ID NO: 78.

In another aspect the present invention provides a composition comprising the fusion polypeptide of the present invention and a pharmaceutically acceptable carrier or diluent.

In another aspect the present invention provides a method of treating a tumour in a subject comprising administering to the subject the fusion polypeptide of the present invention or the composition of the present invention wherein the first domain of the fusion polypeptide binds to cells of the tumour.

In another aspect the present invention provides the use of the fusion polypeptide of the present invention in the treatment of a tumour wherein first domain of the fusion polypeptide binds to the tumour.

In another aspect the present invention provides an isolated polynucleotide(s) encoding the fusion polypeptide(s) of the present invention.

In another aspect the present invention provides a vector comprising the one or more polynucleotides of the present invention.

In another aspect the present invention provides a transformed cell comprising the vector of the present invention.

In another aspect the present invention provides a method of generating a polypeptide ligand-attenuated IFNα2b fusion polypeptide in mammalian cells, wherein the polypeptide ligand-attenuated IFNα2b fusion polypeptide has reduced heterogeneity and/or enhanced FcRn binding and/or improved target selectivity, the method comprising culturing a recombinant mammalian cell comprising a polynucleotide encoding the polypeptide ligand-attenuated IFNα2b fusion polypeptide wherein T106 of the IFNα2b sequence is replaced with another amino acid or is deleted such that on expression in mammalian cells the IFNα2b component of the fusion protein is aglycosylated.

DETAILED DESCRIPTION OF THE INVENTION

Figure 1:
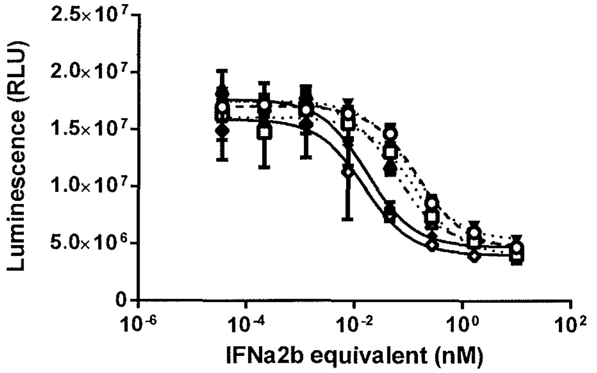
FIG. 1, parts A and B: Anti-proliferative activity upon treatment of (A) ARP1 and (B) NCI-H929 cells with anti-CD38-attenuated IFNα2b fusion proteins in IgG1 or IgG4 format with and without O-linked glycosylation of the IFNα2b.
Figure 1:
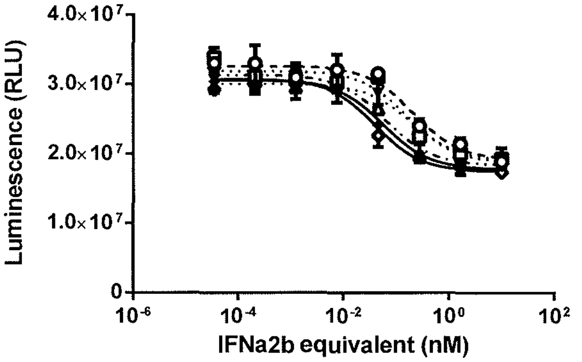
Figure 2A:
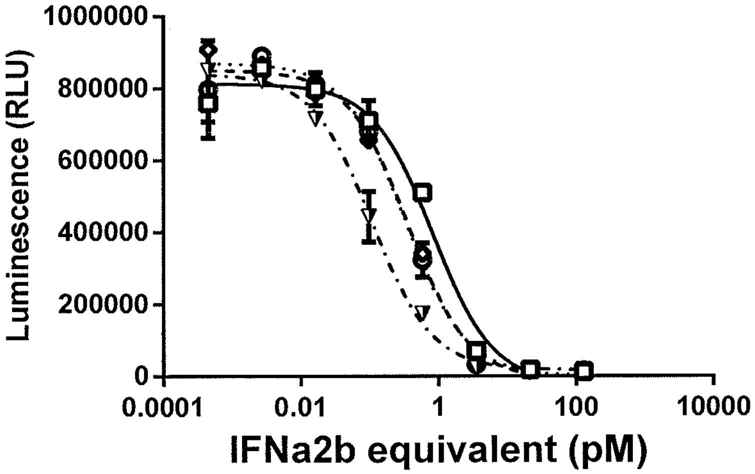
FIG. 2A, FIG. 2B, FIG. 2C, FIG. 2D and FIG. 2E. Anti-proliferative activity of anti-CD38-attenuated IFNα2b fusion proteins with different amino acid substitutions removing the O-linked glycosylation site from the attenuated IFNα2b.
Figure 2B:
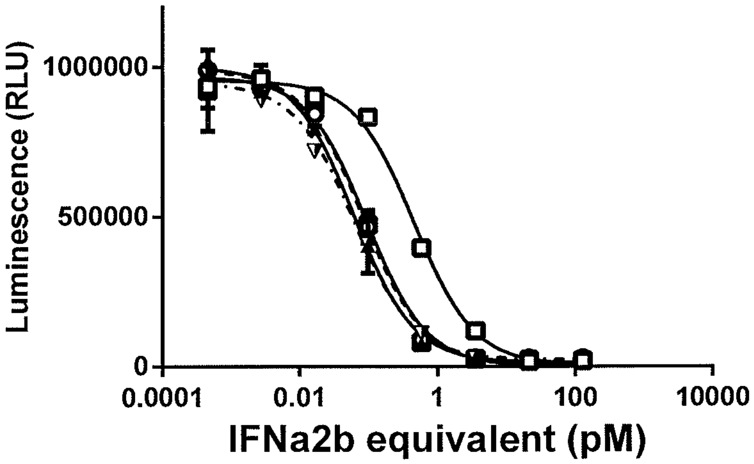
Figure 2C:
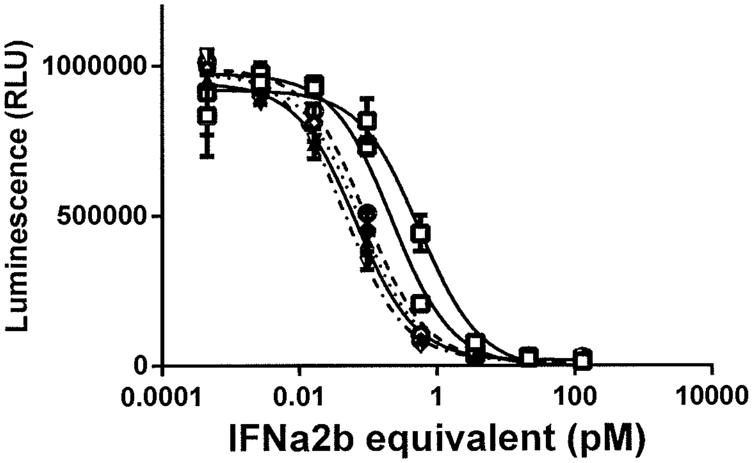
Figure 2D:
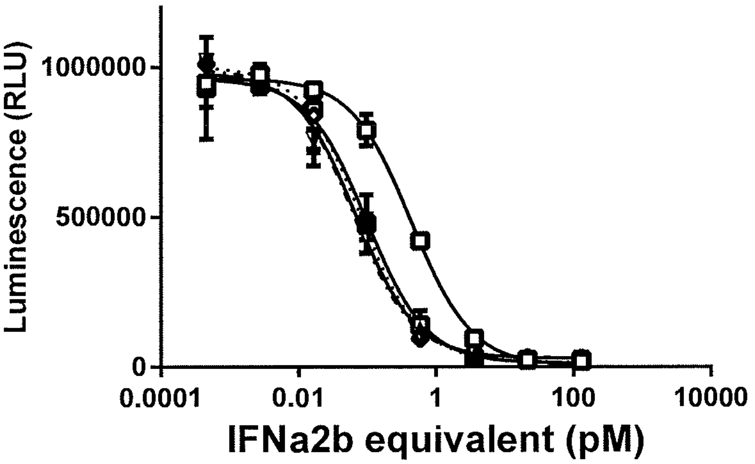
Figure 2E:
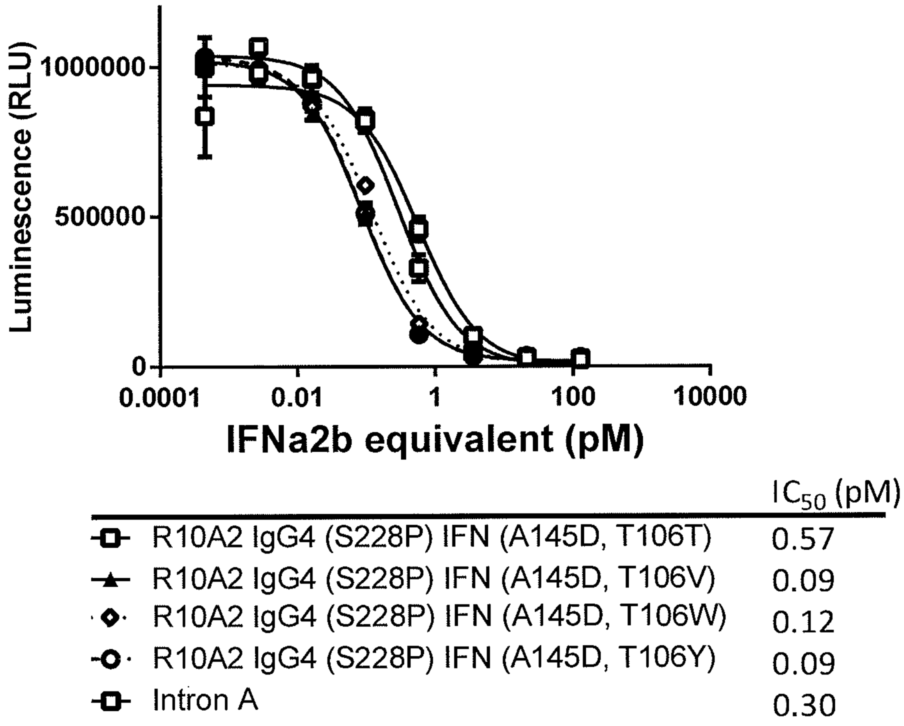

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "an agent" includes a single agent, as well as two or more agents; reference to "a molecule" includes a single molecule, as well as two or more molecules; and so forth.

The constructs of the present invention are polypeptide ligand-attenuated aglycosylated IFNα2b fusion constructs, which show an elevated antigen-selectivity index with respect to activating signaling pathways due to the action of both the ligand targeting to a cell surface receptor on a cell of interest and the attenuated IFNα2b having reduced affinity to a cell surface IFN receptor. These constructs are based on the discovery outlined in WO 2013/059885 that, in the context of an antibody-IFN fusion construct, the IFN portion can be mutated in such a way that the IFN activity on antigen-negative cells is dramatically attenuated, while the IFN activity on antigen-positive cells is only modestly, if at all, attenuated. Such constructs display one, two, three, four or five orders of magnitude greater potency on antigen-positive cells compared to antigen negative cells than does the free IFN. In one embodiment, the antibody-attenuated IFN construct retains at least 1%, at least 10%, at least 20%, at least 30%, at least 40% or at least 50% of the potency on antigen-positive cells as the non-attenuated free (i.e. not attached to an antibody) IFN. In addition, in one embodiment the antibody-attenuated IFN construct retains at least 30%, at least 50%, at least 75% or at least 90% of the maximal activity of the non-attenuated free (i.e. not attached to an antibody) IFN; in this context, "maximal activity" should be understood as meaning the amount of signaling activity (or downstream effect thereof) at the high, plateau portion of a dose-response curve, where further increases in the agent does not further increase the amount of response).

The present inventors have now found that an unexpected advantage is obtained by using constructs comprising aglycosylated IFNα2b as compared to the constructs comprising O-glycosylated IFNα2b. In some embodiments these advantages include one or more of an increase in ON-target activity, increased target selectivity and enhanced affinity to FcRn, whilst providing a less heterogeneous product than the O-glycosylated IFNα2b when produced in a mammalian cell expression system. Enhanced FcRn binding is desirable to improve the pK of a biological therapeutic agent which comprises an Fc region. Increased target selectivity is desirable as it potentially reduces OFF-target toxicity whilst substantially maintaining ON-target activity. A reduction in heterogeneity allows increases in yields of purified product from a mammalian cell culture system.

Accordingly, in a first aspect, the present invention provides a fusion polypeptide comprising a first and a second domain, wherein the first domain comprises a polypeptide ligand which binds to a cell surface-associated antigen and the second domain comprises aglycosylated interferon α 2b (IFNα2b) having a sequence of SEQ ID NO: 1 or SEQ ID NO: 2, and wherein the aglycosylated IFNα2b further comprises one or more amino acid substitutions or deletions which attenuate the activity of the aglycosylated IFNα2b.

In an embodiment of the present invention the sequence of the aglycosylated IFNα2b is SEQ ID NO: 1 in which the residue at position 106 is A, C, D, E, F, G, H, I, K, L, M, N, P, Q, R, S, V, W or Y. This represents a substitution of the T106 normally present in human IFNα2b with a naturally occurring amino acid which does not permit O-linked glycosylation at this position when produced in mammalian cell culture. In another embodiment of the present invention the sequence of the aglycosylated IFNα2b is SEQ ID NO: 2. This represents a deletion of residue T106 found in normal human IFNα2b, which also removes the O-linked glycosylation site found in this molecule. As demonstrated herein, each of the substitutions or deletion removes the O-glycosylation site from human attenuated IFNα2b and reduces the heterogeneity of the molecule as measured in IEF gels, when expressed by CHO cells, and whilst at least substantially maintaining the activity of the attenuated IFNα2b to bind cell surface IFN receptors and to initiate downstream signaling.

In additional embodiments the sequence of the aglycosylated IFNα2b is SEQ ID NO: 1 modified by an attenuating mutation selected from the group consisting of L15A, R22A, R23A, S25A, L26A, F27A, L30A, L30V, K31A, D32A, R33A, R33K, R33Q, H34A, Q40A, D114R, L117A, R120A, R120E, R125A, R125E, K131A, E132A, K133A, K134A, M148A, R149A, S152A, L153A, N156A, (L30A, H57Y, E58N and Q61S), (M148A, H57Y, E58N and Q61S), (L153A, H57Y, E58N and Q61S), (R144A, H57Y, E58N and Q61S), (N65A, L80A, Y85A and Y89A,) (N65A, L80A, Y85A, Y89A and D114A), (N65A, L80A, Y85A, Y89A and L117A), (N65A, L80A, Y85A, Y89A and R120A), (Y85A, Y89A and D114A), (D114A and R120A), (L117A and R120A), (L117A, R120A and K121A), (R120A and K121A), (R120E and K121E), replacement of R at position 144 with A, D, E, G, H, I, K, L, N, Q, S, T, V or Y, replacement of A at position 145 with D, E, G, H, I, K, L, M, N, Q, S, T, V or Y, and deletion of residues L161 to E165.

In additional embodiments the sequence of the aglycosylated IFNα2b is SEQ ID NO: 2 modified by an attenuating mutation selected from the group consisting of L15A, R22A, R23A, S25A, L26A, F27A, L30A, L30V, K31A, D32A, R33A, R33K, R33Q, H34A, Q40A, D113R, L116A, R119A, R119E, R124A, R124E, K130A, E131A, K132A, K133A, M147A, R148A, S149A, L152A, N155A, (L30A, H57Y, E58N and Q61S), (M147A, H57Y, E58N and Q61S), (L152A, H57Y, E58N and Q61S), (R143A, H57Y, E58N and Q61S), (N65A, L80A, Y85A and Y89A,) (N65A, L80A, Y85A, Y89A and D113A), (N65A, L80A, Y85A, Y89A and L116A), (N65A, L80A, Y85A, Y89A and R1190A), (Y85A, Y89A and D113A), (D113A and R119A), (L116A and R119A), (L116A, R119A and K120A), (R119A and K120A), (R119E and K120E), replacement of R at position 143 with A, D, E, G, H, I, K, L, N, Q, S, T, V or Y, replacement of A at position 144 with D, E, G, H, I, K, L, M, N, Q, S, T, V or Y, and deletion of residues L160 to E164.

In another embodiment the sequence of the aglycosylated IFNα2b modified by an attenuating mutation is selected from the group consisting of SEQ ID NOs: 3 to 30 and SEQ ID NOs: 32 to 47.

In another embodiment the cell surface-associated antigen is selected from the group consisting of CD38, CD138, RANK-Ligand, HM1.24, CD56, CS1, CD20, CD74, IL-6R, Blys (BAFF), BCMA, HLA-SR, HLA-DR, Kininogen, beta2 microglobulin, FGFR3, ICAM-1, matriptase, CD52, EGFR, GM2, alpha4-integrin, IFG-1R, KIR, CD3, CD4, CD8, CD24, CD44, CD69, CD71, CD79, CD83, CD86, CD96, HLA, PD-1, ICOS, CD33, CD115, CD11c, CD19, CD52, CD14, FSP1, FAP, PDGFR alpha, PDGFR beta, ASGR1, ASGR2, FSP1, RTI140/Ti-alpha, HTI56, VEGF receptor, CD241 the product of the RCHE gene, CD117 (c-kit), CD71 (transferrin receptor), CD36 (thrombospondin receptor), CD34, CD45RO, CD45RA, CD115, CD168, CD235, CD236, CD237, CD238, CD239 and CD240.

In certain embodiments the polypeptide ligand is an antibody or antigen binding portion thereof.

In another embodiment the polypeptide ligand is an antibody which binds CD38. It is preferred that the $V_H$ sequence of the antibody is selected from the group consisting of SEQ ID Nos: 48 to 56 and 58 and that the $V_L$ sequence of the antibody is selected from the group consisting of SEQ ID Nos: 81, 82 and 84.

In another embodiment the polypeptide ligand is an antibody which binds CD138. It is preferred that the $V_H$ sequence of the antibody is SEQ ID NO: 59 and that the $V_L$ sequence of the antibody is SEQ ID NO: 85.

In another embodiment the polypeptide ligand binds RANK-Ligand. It is preferred that the sequence of the polypeptide ligand is SEQ ID NO: 57.

In another embodiment the first domain is linked to the second domain via a peptide bond. The first domain may be linked to the second domain directly by a peptide bond (a "zero-length linker") or via a peptide linker of from 1 to 20 amino acids in length. The linker may be $(SGGGGS)_n$ (SEQ ID NO: 114) where n is 1 to 3. Examples of linkers include SGGGGS (SEQ ID NO: 114) and SGGGGSGGGGSGGGGS (SEQ ID NO: 115).

In another embodiment the C-terminus of the first domain is linked to N-terminus of the second domain.

In another embodiment the amino acid sequence of the first domain is glycosylated.

In another aspect the present invention provides a fusion polypeptide comprising a sequence selected from the group consisting of SEQ ID NOs: 31, 61 to 77, 83 and 87, and a sequence selected from the group consisting of SEQ ID NOs: 81, 82 and 84.

In another aspect the present invention provides a fusion polypeptide comprising SEQ ID NO: 87 and SEQ ID NO: 81.

In another aspect the present invention provides a fusion polypeptide comprising SEQ ID NO: 79 and SEQ ID NO: 85.

In another aspect the present invention provides a fusion polypeptide comprising SEQ ID NO: 80 and SEQ ID NO: 86.

In another aspect the present invention provides a fusion polypeptide comprising SEQ ID NO: 78.

As will be understood from the discussion above particular forms of the fusion polypeptide of the current invention are as follows:

a. The fusion polypeptide in which the sequence of the aglycosylated IFNα2b is SEQ ID NO: 1 in which the residue at position 106 is A.
b. The fusion polypeptide in which the sequence of the aglycosylated IFNα2b is SEQ ID NO: 1 in which the residue at position 106 is C.
c. The fusion polypeptide in which the sequence of the aglycosylated IFNα2b is SEQ ID NO: 1 in which the residue at position 106 is D.
d. The fusion polypeptide in which the sequence of the aglycosylated IFNα2b is SEQ ID NO: 1 in which the residue at position 106 is E.
e. The fusion polypeptide in which the sequence of the aglycosylated IFNα2b is SEQ ID NO: 1 in which the residue at position 106 is F.
f. The fusion polypeptide in which the sequence of the aglycosylated IFNα2b is SEQ ID NO: 1 in which the residue at position 106 is G.
g. The fusion polypeptide in which the sequence of the aglycosylated IFNα2b is SEQ ID NO: 1 in which the residue at position 106 is H.
h. The fusion polypeptide in which the sequence of the aglycosylated IFNα2b is SEQ ID NO: 1 in which the residue at position 106 is I.
i. The fusion polypeptide in which the sequence of the aglycosylated IFNα2b is SEQ ID NO: 1 in which the residue at position 106 is K.
j. The fusion polypeptide in which the sequence of the aglycosylated IFNα2b is SEQ ID NO: 1 in which the residue at position 106 is L.
k. The fusion polypeptide in which the sequence of the aglycosylated IFNα2b is SEQ ID NO: 1 in which the residue at position 106 is M.
l. The fusion polypeptide in which the sequence of the aglycosylated IFNα2b is SEQ ID NO: 1 in which the residue at position 106 is N.
m. The fusion polypeptide in which the sequence of the aglycosylated IFNα2b is SEQ ID NO: 1 in which the residue at position 106 is P.
n. The fusion polypeptide in which the sequence of the aglycosylated IFNα2b is SEQ ID NO: 1 in which the residue at position 106 is Q.
o. The fusion polypeptide in which the sequence of the aglycosylated IFNα2b is SEQ ID NO: 1 in which the residue at position 106 is R.
p. The fusion polypeptide in which the sequence of the aglycosylated IFNα2b is SEQ ID NO: 1 in which the residue at position 106 is V.
q. The fusion polypeptide in which the sequence of the aglycosylated IFNα2b is SEQ ID NO: 1 in which the residue at position 106 is W.
r. The fusion polypeptide in which the sequence of the aglycosylated IFNα2b is SEQ ID NO: 1 in which the residue at position 106 is Y.
s. The fusion polypeptide in which the sequence of the aglycosylated IFNα2b is SEQ ID NO: 1 or SEQ ID NO: 2 modified by the attenuating mutation L15A.
t. The fusion polypeptide in which the sequence of the aglycosylated IFNα2b is SEQ ID NO: 1 or SEQ ID NO: 2 modified by the attenuating mutation A19W.
u. The fusion polypeptide in which the sequence of the aglycosylated IFNα2b is SEQ ID NO: 1 or SEQ ID NO: 2 modified by the attenuating mutation R22A.
v. The fusion polypeptide in which the sequence of the aglycosylated IFNα2b is SEQ ID NO: 1 or SEQ ID NO: 2 modified by the attenuating mutation R23A.
w. The fusion polypeptide in which the sequence of the aglycosylated IFNα2b is SEQ ID NO: 1 or SEQ ID NO: 2 modified by the attenuating mutation S25A.
x. The fusion polypeptide in which the sequence of the aglycosylated IFNα2b is SEQ ID NO: 1 or SEQ ID NO: 2 modified by the attenuating mutation L26A.
y. The fusion polypeptide in which the sequence of the aglycosylated IFNα2b is SEQ ID NO: 1 or SEQ ID NO: 2 modified by the attenuating mutation F27A.
z. The fusion polypeptide in which the sequence of the aglycosylated IFNα2b is SEQ ID NO: 1 or SEQ ID NO: 2 modified by the attenuating mutation L30A or L30V.
aa. The fusion polypeptide in which the sequence of the aglycosylated IFNα2b is SEQ ID NO: 1 or SEQ ID NO: 2 modified by the attenuating mutation K31A.
bb. The fusion polypeptide in which the sequence of the aglycosylated IFNα2b is SEQ ID NO: 1 or SEQ ID NO: 2 modified by the attenuating mutation D32A.
cc. The fusion polypeptide in which the sequence of the aglycosylated IFNα2b is SEQ ID NO: 1 or SEQ ID NO: 2 modified by the attenuating mutation R33A, R33K or R33Q.
dd. The fusion polypeptide in which the sequence of the aglycosylated IFNα2b is SEQ ID NO: 1 or SEQ ID NO: 2 modified by the attenuating mutation H34A.
ee. The fusion polypeptide in which the sequence of the aglycosylated IFNα2b is SEQ ID NO: 1 or SEQ ID NO: 2 modified by the attenuating mutation Q40A.
ff. The fusion polypeptide in which the sequence of the aglycosylated IFNα2b is SEQ ID NO: 1 modified by the attenuating mutation D114R or SEQ ID NO: 2 modified by the attenuating mutation D113R.
gg. The fusion polypeptide in which the sequence of the aglycosylated IFNα2b is SEQ ID NO: 1 modified by the attenuating mutation L117A or SEQ ID NO: 2 modified by the attenuating mutation L116A.
hh. The fusion polypeptide in which the sequence of the aglycosylated IFNα2b is SEQ ID NO: 1 modified by the attenuating mutation R120A or R120E or SEQ ID NO: 2 modified by the attenuating mutation R119A or R119E.
ii. The fusion polypeptide in which the sequence of the aglycosylated IFNα2b is SEQ ID NO: 1 modified by the attenuating mutation R125A or R125E or SEQ ID NO: 2 modified by the attenuating mutation R124A or R124E.
jj. The fusion polypeptide in which the sequence of the aglycosylated IFNα2b is SEQ ID NO: 1 modified by the attenuating mutation K131A or SEQ ID NO: 2 modified by the attenuating mutation K130A.

kk. The fusion polypeptide in which the sequence of the aglycosylated IFNα2b is SEQ ID NO: 1 modified by the attenuating mutation E132A or SEQ ID NO: 2 modified by the attenuating mutation E131A.

ll. The fusion polypeptide in which the sequence of the aglycosylated IFNα2b is SEQ ID NO: 1 modified by the attenuating mutation K133A or SEQ ID NO: 2 modified by the attenuating mutation K132A.

mm. The fusion polypeptide in which the sequence of the aglycosylated IFNα2b is SEQ ID NO: 1 modified by the attenuating mutation K134A or SEQ ID NO: 2 modified by the attenuating mutation K133A.

nn. The fusion polypeptide in which the sequence of the aglycosylated IFNα2b is SEQ ID NO: 1 modified by the attenuating mutation M148A or SEQ ID NO: 2 modified by the attenuating mutation M147A.

oo. The fusion polypeptide in which the sequence of the aglycosylated IFNα2b is SEQ ID NO: 1 modified by the attenuating mutation R149A or SEQ ID NO: 2 modified by the attenuating mutation R148A.

pp. The fusion polypeptide in which the sequence of the aglycosylated IFNα2b is SEQ ID NO: 1 modified by the attenuating mutation S152A or SEQ ID NO: 2 modified by the attenuating mutation S151A.

qq. The fusion polypeptide in which the sequence of the aglycosylated IFNα2b is SEQ ID NO: 1 modified by the attenuating mutation L153A or SEQ ID NO: 2 modified by the attenuating mutation L152A.

rr. The fusion polypeptide in which the sequence of the aglycosylated IFNα2b is SEQ ID NO: 1 modified by the attenuating mutation N156A or SEQ ID NO: 2 modified by the attenuating mutation N155A.

ss. The fusion polypeptide in which the sequence of the aglycosylated IFNα2b is SEQ ID NO: 1 or SEQ ID NO: 2 modified by the attenuating mutations L30A, H57Y, E58N and Q61S.

tt. The fusion polypeptide in which the sequence of the aglycosylated IFNα2b is SEQ ID NO: 1 modified by the attenuating mutations M148A, H57Y, E58N and Q61S or SEQ ID NO: 2 modified by the attenuating mutations M147A, H57Y, E58N and Q61S.

uu. The fusion polypeptide in which the sequence of the aglycosylated IFNα2b is SEQ ID NO: 1 modified by the attenuating mutations L153A, H57Y, E58N and Q61S or SEQ ID NO: 2 modified by the attenuating mutations L152A, H57Y, E58N and Q61S.

vv. The fusion polypeptide in which the sequence of the aglycosylated IFNα2b is SEQ ID NO: 1 modified by the attenuating mutations R144A, H57Y, E58N and Q61S or SEQ ID NO: 2 modified by the attenuating mutations R143A, H57Y, E58N and Q61S.

ww. The fusion polypeptide in which the sequence of the aglycosylated IFNα2b is SEQ ID NO: 1 or SEQ ID NO: 2 modified by the attenuating mutations N65A, L80A, Y85A and Y89A.

xx. The fusion polypeptide in which the sequence of the aglycosylated IFNα2b is SEQ ID NO: 1 modified by the attenuating mutations N65A, L80A, Y85A, Y89A and D114A or SEQ ID NO: 2 modified by the attenuating mutations N65A, L80A, Y85A, Y89A and D113A.

yy. The fusion polypeptide in which the sequence of the aglycosylated INFα2b is SEQ ID NO: 1 modified by the attenuating mutations N65A, L80A, Y85A, Y89A and L117A or SEQ ID NO: 2 modified by the attenuating mutations N65A, L80A, Y85A, Y89A and L116A.

zz. The fusion polypeptide in which the sequence of the aglycosylated IFNα2b is SEQ ID NO: 1 modified by the attenuating mutations N65A, L80A, Y85A, Y89A and R120A or SEQ ID NO: 2 modified by the attenuating mutations N65A, L80A, Y85A, Y89A and R119A.

aaa. The fusion polypeptide in which the sequence of the aglycosylated IFNα2b is SEQ ID NO: 1 modified by the attenuating mutations Y85A, Y89A and D114A or SEQ ID NO: 2 modified by the attenuating mutations Y85A, Y89A and D113A.

bbb. The fusion polypeptide in which the sequence of the aglycosylated IFNα2b is SEQ ID NO: 1 modified by the attenuating mutations D114A and R120A or SEQ ID NO: 2 modified by the attenuating mutations D113A and R119A.

ccc. The fusion polypeptide in which the sequence of the aglycosylated IFNα2b is SEQ ID NO: 1 modified by the attenuating mutations L117A and R120A or SEQ ID NO: 2 modified by the attenuating mutations L116A and R119A.

ddd. The fusion polypeptide in which the sequence of the aglycosylated IFNα2b is SEQ ID NO: 1 modified by the mutations L117A, R120A and K121A or SEQ ID NO: 2 modified by the mutations L116A, R119A and K120A.

eee. The fusion polypeptide in which the sequence of the aglycosylated IFNα2b is SEQ ID NO: 1 modified by the mutations R120A and K121A or SEQ ID NO: 2 modified by the mutations R119A and K120A.

fff. The fusion polypeptide in which the sequence of the aglycosylated IFNα2b is SEQ ID NO: 1 modified by the mutations R120E and K121E or SEQ ID NO: 2 modified by the mutations R119E and K120E.

ggg. The fusion polypeptide in which the sequence of the aglycosylated IFNα2b SEQ ID NO: 1 is modified by replacement of R at position 144 with A, D, E, G, H, I, K, L, N, Q, S, T, V or Y or SEQ ID NO: 2 is modified by replacement of R at position 143 with A, D, E, G, H, I, K, L, N, Q, S, T, V or Y.

hhh. The fusion polypeptide in which the sequence of the aglycosylated IFNα2b is SEQ ID NO: 1 modified by replacement of A at position 145 with D, E, G, H, I, K, L, M, N, Q, S, T, V or Y or SEQ ID NO: 2 modified by replacement of A at position 144 with D, E, G, H, I, K, L, M, N, Q, S, T, V or Y.

iii. The fusion polypeptide in which the sequence of the aglycosylated IFNα2b is SEQ ID NO: 1 modified by deletion of residues L161 to E165 or SEQ ID NO: 2 modified by deletion of residues L161 to E165.

jjj. The fusion polypeptide as claimed in claim 1 in which the sequence of the aglycosylated IFNα2b is selected from the group consisting of SEQ ID NOs: 3 to 30 and SEQ ID NOs: 32 to 47.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art, non-limiting embodiments of which are discussed below.

In a full-length antibody, each heavy chain is comprised of a heavy chain variable region (abbreviated herein as HCVR or $V_H$) and a heavy chain constant region. The heavy chain constant region is comprised of three domains, CH1, CH2 and CH3. Each light chain is comprised of a light chain variable region (abbreviated herein as LCVR or $V_L$) and a light chain constant region. The light chain constant region is comprised of one domain, CL, which in humans may be of either the κ or λ class. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen binding domain" or "antigen binding portion" of an antibody, as used herein, refers to one or more fragments of an antibody or protein that retain the ability to specifically bind to an antigen (e.g., CD38). It has been shown that the antigen-binding function of an antibody can be performed by fragments of a full-length antibody. Such antibody embodiments may also be bispecific, dual specific, or multi-specific formats, specifically binding to two or more different antigens. Examples of binding fragments encompassed within the term "antigen-binding portion" of an antibody include (i) a Fab fragment, a monovalent fragment consisting of the $V_L$, $V_H$, $C_L$ and CH1 domains; (ii) a F(ab')2 fragment, a bivalent fragment comprising two Fab fragments in addition to a portion of the hinge region, linked by a disulfide bridge at the hinge region; (iii) an Fd fragment consisting of the $V_H$ and CH1 domains; (iv) an Fv fragment consisting of the $V_L$ and $V_H$ domains of a single arm of an antibody, (v) a domain antibody (dAb) (Ward et al. 1989 Nature 341 544-6, Winter et al., PCT publication WO 90/05144 A1 herein incorporated by reference), which comprises a single variable domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. 1988 Science 242 423-6; Huston et al. 1988 Proc Natl Acad Sci USA 85 5879-83). Such single chain antibodies are also intended to be encompassed within the term "antigen-binding portion" of an antibody. Other forms of single chain antibodies, such as diabodies, are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123). Such antibody binding portions are known in the art (Kontermann and Dubel eds., Antibody Engineering 2001 Springer-Verlag. New York. 790 pp., ISBN 3-540-41354-5). In an embodiment the antibody binding portion is a Fab fragment.

The antibody described herein may be a humanized antibody. The term "humanized antibody" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized antibodies also include proteins in which one or more residues of the human protein are modified by one or more amino acid substitutions and/or one or more FR residues of the human protein are replaced by corresponding non-human residues. Humanized antibodies may also comprise residues which are found in neither the human antibody or in the non-human antibody. Any additional regions of the protein (e.g., Fc region) are generally human. Humanization can be performed using a method known in the art, e.g., U.S. Pat. No. 5,225,539, 6,054,297, 7,566,771 or 5,585,089. The term "humanized antibody" also encompasses a super-humanized antibody, e.g., as described in U.S. Pat. No. 7,732,578.

The antibody described herein may be human. The term "human antibody" as used herein refers to proteins having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. Nos. 6,300,064 and/or 6,248,516.

The antibody portions of polypeptides of the present invention may be full length antibodies of any class, preferably IgG1, IgG2 or IgG4. The constant domains of such antibodies are preferably human. The variable regions of such antibodies may be of non-human origin or, preferably, be of human origin or be humanized. Antibody fragments may also be used in place of the full length antibodies.

The term "antibody" also includes engineered antibodies. As will be appreciated there are many variations of engineered antibodies (e.g. mouse monoclonal, chimeric, humanized and human monoclonal antibodies, single chain variable antibody fragments (scFv's), minibodies, aptamers, as well as bispecific antibodies and diabodies as described above).

Single variable region domains (termed dAbs) are, for example, disclosed in (Ward et al., 1989, Nature 341: 544-546; Hamers-Casterman et al., 1993, Nature 363: 446-448; Davies & Riechmann, 1994, FEBS Lett. 339: 285-290).

Minibodies are small versions of whole antibodies, which encode in a single chain the essential elements of a whole antibody. Suitably, the minibody is comprised of the VH and VL domains of a native antibody fused to the hinge region and CH3 domain of the immunoglobulin molecule as, for example, disclosed in U.S. Pat. No. 5,837,821.

In an alternate embodiment, the engineered antibody may comprise non-immunoglobulin derived, protein frameworks. For example, reference may be made to (Ku & Schutz, 1995, Proc. Natl. Acad. Sci. USA 92: 6552-6556)

which discloses a four-helix bundle protein cytochrome b562 having two loops randomized to create CDRs, which have been selected for antigen binding.

There is a plethora of non-antibody recognition protein or protein domain scaffolds that may be utilised as the antigen binding domains in the constructs of this invention. These include scaffolds based on cytotoxic T lymphocyte-associated antigen 4 (CTLA-4) (Evibody; U.S. Pat. No. 7,166,697); human transferrin (Trans-body); a three-helix bundle from the Z-domain of Protein A (Affibody); a monomeric or trimeric human C-type lectin domain (Tetranectin); the tenth human fibronectin type III domain (AdNectin); the Kunitz-type domain of human or bovine trypsin inhibitor; insect Defensin A (IICA29), APPI (Kuntiz domains); lipocalins, FABP, Bilin-binding protein, Apoloproptein D (Anticalins); human α-crystallin or ubiquitin molecule (Affilin); trypsin inhibitor II (Microbody); α2p8 or Ankyrin repeat (repeat-motif proteins), Charybdotoxin (Scorpion toxins), Min-23, Cellulose binding domain (Knottins); Neocarzinostatin, CBM4-2 and Tendamistat.

Further, in addition to scaffolds provided for by antibody-derived domains or non-antibody folds as described above, there are naturally occurring ligand binding proteins or protein domains that may be utilised as the ligand binding domains in this invention. For example, protein domains that possess ligand binding properties include extracellular domains of receptors, PDZ modules of signaling proteins, such as Ras-binding protein AF-6, adhesion molecules, and enzymes.

Using methods well known in the art to increase binding, by for example, affinity maturation, or to decrease immunogenicity by removing predicted MHC class II-binding motifs. The therapeutic utility of the antibodies described herein can be further enhanced by modulating their functional characteristics, such as antibody-dependent cell-mediated cytotoxicity (ADCC), complement-dependent cytotoxicity (CDC), serum half-life, biodistribution and binding to Fc receptors or the combination of any of these. This modulation can be achieved by protein-engineering, glyco-engineering or chemical methods. Depending on the therapeutic application required, it could be advantageous to either increase or decrease any of these activities.

An example of glyco-engineering used the Potelligent® method as described in Shinkawa T. et al., 2003 (J Biol Chem 278: 3466-73).

Numerous methods for affinity maturation of antibodies are known in the art. Many of these are based on the general strategy of generating panels or libraries of variant proteins by mutagenesis followed by selection and/or screening for improved affinity. Mutagenesis is often performed at the DNA level, for example by error prone PCR (Thie, Voedisch et al. 2009, Methods Mol Biol 525: 309-322), by gene shuffling (Kolkman and Stemmer 2001, Nat Biotechnol. May; 19(5):423-8), by use of mutagenic chemicals or irradiation, by use of 'mutato' strains with error prone replication machinery (Greener 1996, In Vitro Mutagenesis Protocols. Humana press, NJ) or by somatic hypermutation approaches that harness natural affinity maturation machinery (Peled, Kuang et al. 2008, Annu Rev Immunol. 26:481-511). Mutagenesis can also be performed at the RNA level, for example by use of Qβ replicase (Kopsidas, Roberts et al. 2006, Immunol Lett. 2006 Nov. 15; 107(2):163-8). Library-based methods allowing screening for improved variant proteins can be based on various display technologies such as phage, yeast, ribosome, bacterial or mammalian cells, and are well known in the art (Benhar 2007, Expert Opin Biol Ther. May; 7(5): 763-79). Affinity maturation can be achieved by more directed/predictive methods for example by site-directed mutagenesis or gene synthesis guided by findings from 3D protein modeling (see for example Queen, Schneider et al. 1989, PNAS, 86(24): 10029-33 or U.S. Pat. No. 6,180,370 or 5,225,539).

Methods of increasing ADCC have been described by Ferrara, Brunker et al. 2006, Biotechnol Bioeng; 93:851-61; Li, Sethuraman et al. 2006, Nat Biotechnol; 24:210-5; Stavenhagen, Gorlatov et al. 2007, Cancer Res; 67:8882-90; Shields, Namenuk et al. 2001, J Biol Chem; 276:6591-604; Shinkawa, Nakamura et al. 2003, J Biol Chem; 278:3466-73; and WO 2008/006554.

Methods of increasing CDC have been described by Idusogie, Wong et al. 2001, J Immunol; 176:346-56; Dall'Acqua, Cook et al. 2006, J Biol Chem; 281:23514-24; Michaelsen, Aase et al. 1990, Scand J Immunol; 32:517-28; Brekke, Bremnes et al. 1993, Mol Immunol; 30:1419-25; Tan, Shopes et al. 1990, PNAS; 87:162-6; and Norderhaug, Brekke et al. 1991, Eur J Immunol; 21:2379-84.

References describing methods of increasing ADCC and CDC include Natsume, In et al. 2008, Cancer Res; 68:3863-72. The disclosure of each of these references is included herein by cross reference. In certain embodiments it may be advantageous to reduce or eliminate ADCC and CDC activities of the antibody component of the polypeptide of the invention, so that the IFNα2b activity is the principal activity of the polypeptide which modulates target cell survival.

A number of methods for modulating antibody serum half-life and biodistribution are based on modifying the interaction between antibody and the neonatal Fc receptor (FcRn), a receptor with a key role in protecting IgG from catabolism, and maintaining high serum antibody concentration. Dall'Acqua et al describe substitutions in the Fc region of IgG1 that enhance binding affinity to FcRn, thereby increasing serum half-life (Dall'Acqua, Woods et al. 2002, J Immunol; 169:5171-80) and further demonstrate enhanced bioavailability and modulation of ADCC activity with triple substitution of M252Y/S254T/T256E (with residue numbering according to the EU Index) or M265Y/S267T/T269 (with residue numbering according to the Kabat numbering system) (Dall'Acqua, Kiener et al. 2006, J Biol Chem; 279:6213-6). See also U.S. Pat. Nos. 6,277,375; 6,821,505; and 7,083,784. Hinton et al have described constant domain amino acid substitutions at positions 250 and 428 that confer increased in vivo half-life (Hinton, Johlfs et al. 2004, J Biol Chem; 279:6213-6; Hinton, Xiong et al. 2006, J Immunol; 176:346-56). See also U.S. Pat. No. 7,217,797. Petkova et al have described constant domain amino acid substitutions at positions 307, 380 and 434 that confer increased in vivo half-life (Petkova, Akilesh et al. 2006, Int Immunol; 18:1759-69). See also Shields et al 2001, J Biol Chem; 276:6591-604 and WO 2000/42072. Other examples of constant domain amino acid substitutions which modulate binding to Fc receptors and subsequent function mediated by these receptors, including FcRn binding and serum half-life, are described in U.S. Pat. Application Nos 20090142340; 20090068175 and 20090092599. The substitution referred to herein as "S228P" which is numbered according to the EU index as in Kabat has also been referred to as "S241P" according to Kabat et al. (1987 Sequences of proteins of immunological interest. United States Department of Health and Human Services, Washington D.C.). This substitution stabilizes the hinge region of IgG4 molecules, having the effect of making the sequence of the core of the hinge region the same as that of an IgG1 or IgG2 isotype antibody. This results in a reduction in the spontaneous dissociation and reassociation of the heavy chains which often leads to the production of heterodimeric IgG4 antibodies.

The glycans linked to antibody molecules are known to influence interactions of antibody with Fc receptors and glycan receptors and thereby influence antibody activity, including serum half-life (Kaneko, Nimmerjahn et al. 2006, Science; 313:670-3; Jones, Papac et al. 2007, Glcobiology; 17:529-40; and Kanda, Yamada et al. 2007, Glycobiology; 17:104-18). Hence, certain glycoforms that modulate desired antibody activities can confer therapeutic advantage. Methods for generating engineered glycoforms are known in the art and include but are not limited to those described in U.S. Pat. Nos. 6,602,684; 7,326,681; 7,388,081 and in WO 2008/006554.

Extension of half-life by addition of polyethylene glycol (PEG) has been widely used to extend the serum half-life of proteins, as reviewed, for example, by Fishburn 2008, J Pharm Sci; 97:4167-83.

As will be recognised it is possible to make conservative amino acid substitutions within the sequences of the current invention. By "conservative substitution" is meant amino acids having similar properties. As used in this specification the following groups of amino acids are to be seen as conservative substitutions: H, R and K; D, E, N and Q; V, I and L; C and M; S, T, P, A and G; and F, Y and W. It is not intended, however, that substitutions other than those specifically recited are made at the sites of attenuation and/or glycosylation.

The term "cell surface-associated antigen", as used herein, broadly refers to any antigen expressed on surfaces of cells, including without limitation malignant cells or infectious or foreign cells.

In certain aspects of the present invention, the fusion polypeptide constructs or compositions of the present invention may be used to treat patients with cancer. Cancers contemplated herein include: a group of diseases and disorders that are characterized by uncontrolled cellular growth (e.g. formation of tumor) without any differentiation of those cells into specialized and different cells. Such diseases and disorders include ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, multiple myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor. In an embodiment the tumor is selected from a group of multiple myeloma or non-hodgkin's lymphoma.

As contemplated for the treatment of cancer, the antibody portions of the fusion constructs of the present invention may bind to tumour-associated antigens, i.e., cell surface antigens that are selectively expressed by cancer cells or over-expressed in cancer cells relative to most normal cells. There are many tumour-associated antigens (TAAs) known in the art. Non-limiting examples of TAAs include enzyme tyrosinase; melanoma antigen GM2; alphafetoprotein (AFP); carcinoembryonic antigen (CEA); Mucin 1 (MUC1); Human epidermal growth factor receptor (Her2/Neu); T-cell leukemia/lymphoma 1 (TCL1) oncoprotein. Exemplary TAAs associated with a number of different cancers are telomerase (hTERT); prostate-specific membrane antigen (PSMA); urokinase plasminogen activator and its receptor (uPA/uPAR); vascular endothelial growth factor and its receptor (VEGF/VEGFR); extracellular matrix metalloproteinase inducer (EMMPRIN/CD147); epidermal growth factor (EGFR); platelet-derived growth factor and its receptor (PDGF/PDGFR) and c-kit (CD117).

A list of other TAAs is provided in US 2010/0297076, the disclosure of which is included herein by reference. Of particular interest are cell surface antigens associated with multiple myeloma leukemia or lymphoma cells, including but not limited to CD38, CD138, CD79, CS1, and HM1.24. In one embodiment an antigen for ligand-attenuated IFN constructs, for example, an antibody-attenuated interferon construct, is CD38.

CD38 is a 46 kDa type II transmembrane glycoprotein. It has a short N-terminal cytoplasmic tail of 20 amino acids, a single transmembrane helix and a long extracellular domain of 256 amino acids (Bergsagel, P., Blood; 85:436, 1995 and Liu, Q., Structure, 13:1331, 2005). It is expressed on the surface of many immune cells including CD4 and CD8 positive T cells, B cells, NK cells, monocytes, plasma cells and on a significant proportion of normal bone marrow precursor cells (Malavasi, F., Hum. Immunol. 9:9, 1984). In lymphocytes, however, the expression appears to be dependent on the differentiation and activation state of the cell. Resting T and B cells are negative while immature and activated lymphocytes are predominantly positive for CD38 expression (Funaro, A., J. Immunol. 145:2390, 1990). Additional studies indicate mRNA expression in non-hemopoeitic organs such as pancreas, brain, spleen and liver (Koguma, T., Biochim. Biophys. Acta 1223:160, 1994.)

CD38 is a multifunctional ectoenzyme that is involved in transmembrane signaling and cell adhesion. It is also known as cyclic ADP ribose hydrolase because it can transform $NAD^+$ and $NADP^+$ into cADPR, ADPR and NAADP, depending on extracellular pH. These products induce $Ca^{2+}$-mobilization inside the cell which can lead to tyrosine phosphorylation and activation of the cell. CD38 is also a receptor that can interact with a ligand, CD31. Activation of receptor via CD31 leads to intracellular events including $Ca^{2+}$ mobilization, cell activation, proliferation, differentiation and migration (reviewed in Deaglio, S., Trends in Mol. Med. 14:210, 2008.)

CD38 is expressed at high levels on multiple myeloma cells, in most cases of T- and B-lineage acute lymphoblastic leukemias, some acute myelocytic leukemias, follicular center cell lymphomas and T lymphoblastic lymphomas. (Malavasi, F., J. Clin Lab Res. 22:73, 1992). More recently, CD38 expression has become a reliable prognostic marker in B-lineage chronic lymphoblastic leukemia (B-CLL) (Ibrahim, S., Blood. 98:181, 2001 and Durig, J., Leuk. Res. 25:927, 2002). Independent groups have demonstrated that B-CLL patients presenting with a $CD38^+$ clone are characterized by an unfavorable clinical course with a more advance stage of disease, poor responsiveness to chemotherapy and shorter survival time (Morabito, F., Haematologica. 87:217, 2002). The consistent and enhanced expression of CD38 on lymphoid tumors makes this an attractive target for therapeutic antibody technologies.

Preferred antigens for the development of antibody-attenuated aglycosylated IFNα2b fusion protein constructs which target cancer are antigens which show selective or greater expression on the cancer cells than on most other, non-transformed cells within the body. Non-protein examples of such antigens include, sphingolipids, ganglioside GD2 (Saleh et al., 1993, J. Immunol., 151, 3390-3398), ganglioside GD3 (shitara et al., 1993, Cancer Immunol. Immunother. 36:373-380), ganglioside GM2 (Livingston et al., 1994, J. Clin. Oncol. 12:1036-1044), ganglioside GM3 (Hoon et al., 1993, Cancer Res. 53:5244-5250) and $Lewis^x$, $lewis^y$ and $lewis^{xy}$ carbohydrate antigens that can be displayed on proteins or glycolipids. Examples of protein antigens are HER-2/neu, human papillomavirus-E6 or -E7, MUC-1; KS 1/4 pan-carcinoma antigen (Perez and Walker, 1990, J. Immunol. 142:3662-3667; Bumal, 1988, Hybridoma 7(4):407-415); ovarian carcinoma antigen CA125 (Yu et al., 1991, Cancer Res. 51(2):468-475); prostatic acid phosphate (Tailor et al., 1990, Nucl. Acids Res. 18(16):4928); prostate specific antigen (Henttu and Vihko, 1989, Biochem. Biophys. Res. Comm. 160(2):903-910; Israeli et al., 1993, Cancer Res. 53:227-230); melanoma-associated antigen p97 (Estin et al., 1989, J. Natl. Cancer Instit. 81(6):445-446); melanoma antigen gp75 (Vijayasardahl et al., 1990, J. Exp. Med. 171(4):1375-1380); prostate specific membrane antigen; carcinoembryonic antigen (CEA) (Foon et al., 1994, Proc. Am. Soc. Clin. Oncol. 13:294), MUC16 (antibodies include MJ-170, MJ-171, MJ-172 and MJ-173 [U.S. Pat. No. 7,202,346], 3A5 [U.S. Pat. No. 7,723,485]).NMB (U.S. Pat. No. 8,039,593), malignant human lymphocyte antigen-APO-1 (Bernhard et al., 1989, Science 245:301-304); high molecular weight melanoma antigen (HMW-MAA) (Natali et al., 1987, Cancer 59:55-63; Mittelman et al., 1990, J. Clin. Invest. 86:2136-2144); Burkitt's lymphoma antigen-38.13; CD19 (Ghetie et al., 1994, Blood 83:1329-1336); human B-lymphoma antigen-CD20 (Reff et al., 1994, Blood 83:435-445); GICA 19-9 (Herlyn et al., 1982, J. Clin. Immunol. 2:135), CTA-1 and LEA; CD33 (Sgouros et al., 1993, J. Nucl. Med. 34:422-430); oncofetal antigens such as alpha-fetoprotein for liver cancer or bladder tumor oncofetal antigen (Hellstrom et al., 1985, Cancer. Res. 45:2210-2188); differentiation antigens such as human lung carcinoma antigen L6 or L20 (Hellstrom et al., 1986, Cancer Res. 46:3917-3923); antigens of fibrosarcoma; human leukemia T cell antigen-Gp37 (Bhattacharya-Chatterjee et al., 1988, J. Immunol. 141:1398-1403); tumor-specific transplantation type of cell-surface antigen (TSTA) such as virally-induced tumor antigens including T-antigen, DNA tumor virus and envelope antigens of RNA tumor viruses; neoglycoproteins, breast cancer antigens such as EGFR (Epidermal growth factor receptor), polymorphic epithelial mucin (PEM) (Hilkens et al., 1992, Trends in Bio. Chem. Sci. 17:359); polymorphic epithelial mucin antigen; human milk fat globule antigen; colorectal tumor-associated antigens such as TAG-72 (Yokata et al., 1992, Cancer Res. 52:3402-3408), CO 17-1A (Ragnhammar et al., 1993, Int. J. Cancer 53:751-758); differentiation antigens (Feizi, 1985, Nature 314:53-57) such as I(Ma) found in gastric adenocarcinomas, SSEA-1 found in myeloid cells, VEP8, VEP9, Myl, VIM-D5, M18 and M39 found in breast epithelial cancers, $D_{156-22}$ found in colorectal cancer, TRA-1-85 (blood group H), C14 found in colonic adenocarcinoma, F3 found in lung adenocarcinoma, AH6 found in gastric cancer, Y hapten found in embryonal carcinoma cells, TL5 (blood group A), E1 series (blood group B) antigens found in pancreatic cancer, FC10.2 found in embryonal carcinoma cells, gastric adenocarcinoma antigen, CO-514 (blood group Lea) found in adenocarcinoma, NS-10 found in adenocarcinomas, CO-43 (blood group Leb), G49 found in A431 cells, 19.9 found in colon cancer; gastric cancer mucins; $R_{24}$ found in melanoma, MH2 (blood group $ALe^b/Le^y$) found in colonic adenocarcinoma, 4.2, D1.1, OFA-1, $G_{M2}$, OFA-2 and M1:22:25:8 found in embryonal carcinoma cells and SSEA-3 and SSEA-4. HMW-MAA (SEQ ID NO:433), also known as melanoma chondroitin sulfate proteoglycan, is a membrane-bound protein of 2322 residues which is overexpressed on over 90% of the surgically removed benign nevi and melanoma lesions (Camploi, et. al, Crit Rev Immunol.; 24:267, 2004). Accordingly it may be a potential target cell surface associated antigen.

Other example cancer antigens for targeting with fusion protein constructs of the present invention include (exemplary cancers are shown in parentheses): CD5 (T-cell leukemia/lymphoma), CA15-3 (carcinomas), CA19-9 (carcinomas), L6 (carcinomas), CA 242 (colorectal), placental alkaline phosphatase (carcinomas), prostatic acid phosphatase (prostate), MAGE-1 (carcinomas), MAGE-2 (carcinomas), MAGE-3 (carcinomas), MAGE-4 (carcinomas), transferrin receptor (carcinomas), p97 (melanoma), MUC1 (breast cancer), MART1 (melanoma), CD20 (non Hodgkin's lymphoma), CD52 (leukemia), CD33 (leukemia), human chorionic gonadotropin (carcinoma), CD38 (multiple myeloma), CD21 (B-cell lymphoma), CD22 (lymphoma), CD25 (B-cell Lymphoma), CD37 (B-cell lymphoma), CD45 (acute myeloblastic leukemia), HLA-DR (B-cell lymphoma), IL-2 receptor (T-cell leukemia and lymphomas), CD40 (lymphoma), CD79 (B cell leukemia or lymphoma, Hodgkin lymphoma), various mucins (carcinomas), P21

(carcinomas), MPG (melanoma), Ep-CAM (Epithelial Tumors), Folate-receptor alpha (Ovarian), A33 (Colorectal), G250 (renal), Ferritin (Hodgkin lymphoma), de2-7 EGFR (glioblastoma, breast, and lung), Fibroblast activation protein (epithelial) and tenascin metalloproteinases (glioblastoma). Some specific, useful antibodies include, but are not limited to, BR64 (Trail et al., 1997, Cancer Research 57:100 105), BR96 mAb (Trail et al., 1993, Science 261:212-215), mAbs against the CD40 antigen, such as S2C6 mAb (Francisco et al., 2000, Cancer Res. 60:3225-3231) or other anti-CD40 antibodies, such as those disclosed in U.S. Patent Publication Nos. 2003-0211100 and 2002-0142358; mAbs against the CD30 antigen, such as AC10 (Bowen et al., 1993, J. Immunol. 151:5896-5906; Wahl et al., 2002 Cancer Res. 62(13):3736-42) or MDX-0060 (U.S. Patent Publication No. 2004-0006215) and mAbs against the CD70 antigen, such as 1F6 mAb and 2F2 mAb (see, e.g., U.S. Patent Publication No. 2006-0083736) or antibodies 2H5, 10B4, 8B5, 18E7, 69A7 (U.S. Pat. No. 8,124,738). Other antibodies have been reviewed elsewhere (Franke et al., 2000, Cancer Biother. Radiopharm. 15:459 76; Murray, 2000, Semin. Oncol. 27:64 70; Breitling, F., and Dubel, S., Recombinant Antibodies, John Wiley, and Sons, New York, 1998).

In certain embodiments, useful antibodies can bind to a receptor or a complex of receptors expressed on a target cell. The receptor or receptor complex can comprise an immunoglobulin gene superfamily member, a major histocompatibility protein, a cytokine receptor, a TNF receptor superfamily member, a chemokine receptor, an integrin, a lectin, a complement control protein, a growth factor receptor, a hormone receptor or a neuro-transmitter receptor. Non-limiting examples of appropriate immunoglobulin superfamily members are CD2, CD3, CD4, CD8, CD19, CD22, CD79, CD90, CD152/CTLA-4, PD-1, B7-H4, B7-H3, and ICOS. Non-limiting examples of suitable TNF receptor superfamily members are TACI, BCMA, CD27, CD40, CD95/Fas, CD134/OX40, CD137/4-1BB, TNFR1, TNFR2, RANK, osteoprotegerin, APO 3, Apo2/TRAIL R1, TRAIL R2, TRAIL R3, and TRAIL R4. Non-limiting examples of suitable integrins are CD11a, CD11b, CD11c, CD18, CD29, CD41, CD49a, CD49b, CD49c, CD49d, CD49e, CD49f, CD103 and CD104. Non-limiting examples of suitable lectins are S type, C type, and I type lectin. Examples of antibodies to CEA are shown in Table 1.

TABLE 1

| CEA Antibodies | | | |
|---|---|---|---|
| Ab Clones | Patent | Assignee | Comments |
| COL-1 | U.S. Pat. No. 6,417,337 | The Dow Chemical Company | Humanized |
| 806.077 | U.S. Pat. No. 6,903,203 | AstraZeneca UK Ltd. | Humanized |
| T84.66 | U.S. Pat. No. 7,776,330 | City of Hope | Humanized |

antibodies that bind the CD22 antigen expressed on human B cells include, for example, HD6, RFB4, UV22-2, To15, 4KB128 and a humanized anti-CD22 antibody (hLL2) (see, e.g., Li et al. (1989) Cell. Immunol. 111: 85-99; Mason et al. (1987) Blood 69: 836-40; Behr et al. (1999) Clin. Cancer Res. 5: 3304s-3314s; Bonardi et al. (1993) Cancer Res. 53: 3015-3021).

Antibodies to CD33 include, for example, HuM195 (see, e.g., Kossman et al. (1999) Clin. Cancer Res. 5: 2748-2755; U.S. Pat. No. 5,693,761) and CMA-676 (see, e.g., Sievers et al., (1999) Blood 93: 3678-3684).

Illustrative anti-MUC-1 antibodies include, but are not limited to Mc5 (see, e.g., Peterson et al. (1997) Cancer Res. 57: 1103-1108; Ozzello et al. (1993) Breast Cancer Res. Treat. 25: 265-276), and hCTMO1 (see, e.g., Van Hof et al. (1996) Cancer Res. 56: 5179-5185).

Illustrative anti-TAG-72 antibodies include, but are not limited to CC49 (see, e.g., Pavlinkova et al. (1999) Clin. Cancer Res. 5: 2613-2619), B72.3 (see, e.g., Divgi et al. (1994) Nucl. Med. Biol. 21: 9-15), and those disclosed in U.S. Pat. No. 5,976,531.

Illustrative anti-HM1.24 antibodies include, but are not limited to a mouse monoclonal anti-HM1.24 and a humanized anti-HM1.24 IgGlkappa antibody (see, e.g., Ono et al. (1999) Mol. Immuno. 36: 387-395).

In certain embodiments the targeting moiety comprises an anti-Her2 antibody. The erBB 2 gene, more commonly known as (Her-2/neu), is an oncogene encoding a transmembrane receptor. Several antibodies have been developed against Her-2/neu, and some of these are in clinical use. These include trastuzumab (e.g., HERCEPTIN™; Fornir et al. (1999) Oncology (Huntingt) 13: 647-58), TAB-250 (Rosenblum et al. (1999) Clin. Cancer Res. 5: 865-874), BACH-250 (Id.), TA1 (Maier et al. (1991) Cancer Res. 51: 5361-5369), and the mAbs described in U.S. Pat. Nos. 5,772,997; 5,770,195 (mAb 4D5; ATCC CRL 10463); and U.S. Pat. No. 5,677,171.

Other fully human anti-Her2/neu antibodies are well known to those of skill in the art. Such antibodies include, but are not limited to the C6 antibodies such as C6.5, DPL5, G98A, C6MH3-B1, B1D2, C6VLB, C6VLD, C6VLE, C6VLF, C6MH3-D7, C6MH3-D6, C6MH3-D5, C6MH3-D3, C6MH3-D2, C6MH3-D1, C6MH3-C4, C6MH3-C3, C6MH3-B9, C6MH3-B5, C6MH3-B48, C6MH3-B47, C6MH3-B46, C6MH3-B43, C6MH3-B41, C6MH3-B39, C6MH3-B34, C6MH3-B33, C6MH3-B31, C6MH3-B27, C6MH3-B25, C6MH3-B21, C6MH3-B20, C6MH3-B2, C6MH3-B16, C6MH3-B15, C6MH3-B11, C6MH3-B1, C6MH3-A3, C6MH3-A2, and C6ML3-9. These and other anti-HER2/neu antibodies are described in U.S. Pat. Nos. 6,512,097 and 5,977,322, in PCT Publication WO 97/00271, in Schier et al. (1996) J Mol Biol 255: 28-43, Schier et al. (1996) J Mol Biol 263: 551-567, and the like.

More generally, antibodies directed to various members of the epidermal growth factor receptor family are well suited for use as targeting antibodies or antigen binding portions thereof in the constructs of the present invention. Such antibodies include, but are not limited to anti-EGFR antibodies as described in U.S. Pat. Nos. 5,844,093 and 5,558,864, and in European Patent No. 706,799A. Other illustrative anti-EGFR family antibodies include, but are not limited to antibodies such as C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7 and the like (see, e.g., U.S. Patent publications US 2006/0099205 A1 and US 2004/0071696 A1 which are incorporated herein by reference).

CD38 is of particular interest as an antibody target for fusion protein constructs of the present invention. Antibodies to CD38 include for example, AT13/5 (see, e.g., Ellis et al. (1995) J. Immunol. 155: 925-937), HB7, and the like.

The present invention also provides compositions comprising the fusion polypeptides of the present invention.

These compositions can further comprise at least one of any suitable auxiliary, such as, but not limited to, diluent, binder, stabiliser, buffers, salts, lipophilic solvents, preservative, adjuvant or the like. Pharmaceutically acceptable auxiliaries are preferred. Non-limiting examples of, and methods of preparing such sterile solutions are well known in the art, such as, but not limited to, Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of the antibody composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatised sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acids which can also function in a buffering capacity include alanine, glycine, arginine, betaine, histidine, glutamic acid, aspartic acid, cysteine, lysine, leucine, isoleucine, valine, methionine, phenylalanine, aspartame, and the like. One preferred amino acid is histidine. A second preferred amino acid is arginine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, phosphate buffers or amino acid buffers. Preferred buffers for use in the present compositions are organic acid salts, such as citrate or amino acids.

Additionally, the compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN® 20" and "TWEEN® 80"), lipids (e.g., phospholipids, fatty acids), steroids (e.g., cholesterol), and chelating agents (e.g., EDTA).

These and additional known pharmaceutical excipients and/or additives suitable for use in the antibody compositions according to the invention are known in the art, e.g., as listed in "Remington: The Science & Practice of Pharmacy", 19th ed., Williams & Williams, (1995), and in the "Physician's Desk Reference", 52 nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

EXAMPLES

General Methods

Production of Antibody-Fusion Constructs in HEK-293E Cells.

The DNA sequences of a number of the domains in the fusion polypeptides of the present are provided in the attached Sequence listing incorporated herein. DNA plasmids encoding protein constructs (antibody-attenuated IFNα2b fusion constructs) were prepared using HiSpeed Plasmid Maxi Kit (Qiagen, Valencia, Calf.) and then transfected into HEK293E cells (CNRC, Montreal, Canada), grown in F17 synthetic medium supplemented with 0.45% (w/v) D-(+)-Glucose (Sigma, Castle Hill, NSW), 25 μg/mL Geneticin (Invitrogen, Carlsbad, Calif.), and 1×GlutaMAX (Invitrogen, Carlsbad, Calif.) using a commercially available transfection reagent and OptiMEM medium (Invitrogen, Carlsbad, Calif.). After allowing for expression for 6 days in an incubator supplied with 5% $CO_2$ and 120 rpm shaking, the culture media was isolated and subjected to affinity purification using Protein A MABSELECT SURE® agarose beads (GE Healthcare, Piscataway, N.J.). Purified protein constructs were buffer-exchanged into 0.2M arginine HCl, 25 mM citric acid, 71.5 mM sodium hydroxide at pH 6.0 using a PD Midi-Trap G-25 column (GE Healthcare, Piscataway, N.J.) or a HiPrep 26/10 Desalting column (HiTrap Desalting HiPrep 26/10 Desalting). Purified protein constructs were then concentrated using 50 kDa Amicon Ultra centrifugal filter devices (Millipore, Billerica, Mass.), followed by protein concentration determination by reading absorbance at 280 nm.

Production of Antibody-Fusion Constructs in EXPI293 Cells.

DNA plasmids encoding protein constructs (antibody-IFNα2b related constructs) were prepared using HiSpeed Plasmid Maxi Kit (Qiagen, Valencia, Calif.) and then transfected into EXPI293 cells (Life Technologies, Carlsbad, Calif.), grown in EXPI Expression medium (Life Technologies, Carlsbad, Calif.) using transfection reagent provided in the EXPI293 transfection kit and OptiMEM medium (Invitrogen, Carlsbad, Calif.). After allowing for expression for 3 days in an incubator supplied with 5% $CO_2$ and 125 rpm shaking, the culture media was isolated and subjected to affinity purification using Protein A MABSELECT SURE® agarose beads (GE Healthcare, Piscataway, N.J.). Purified protein constructs were buffer-exchanged into 0.2M arginine HCl, at pH 6.0 using a PD Midi-Trap G-25 column (GE Healthcare, Piscataway, N.J.) or a HiPrep 26/10 Desalting column (HiTrap Desalting HiPrep 26/10 Desalting). Purified protein constructs were then concentrated using 50 kDa Amicon Ultra centrifugal filter devices (Millipore, Billerica, Mass.), followed by protein concentration determination by reading absorbance at 280 nm.

Production of Antibody-Fusion Constructs in CHO Sells.

DNA plasmids encoding protein constructs (antibody-IFNα2b related constructs) were prepared using HiSpeed Plasmid Maxi Kit (Qiagen, Valencia, Calif.) and then transfected into CHO cells (Lonza) grown in FREESTYLE™ CHO Expression Medium (Invitrogen, Carlsbad, Calif.) using a commercially available transfection reagent and OptiPro SFM™ medium (Invitrogen, Carlsbad, Calif.). After allowing for expression for 6 days in an incubator supplied with 10% $CO_2$ and 120 rpm shaking, the culture media was isolated and subjected to affinity purification using Protein A MABSELECT SURE® agarose beads (GE Healthcare, Piscataway, N.J.). Purified protein constructs were buffer-exchanged into 0.2M arginine.HCl, 25 mM citric acid, 71.5 mM sodium hydroxide at pH 6.0 using a PD Midi-Trap G-25 column (GE Healthcare, Piscataway, N.J.) or a HiPrep 26/10 Desalting column (HiTrap Desalting HiPrep 26/10 Desalting). Purified protein constructs were then concentrated using 50 kDa Amicon Ultra centrifugal filter devices (Millipore, Billerica, Mass.), followed by protein concentration determination by reading absorbance at 280 nm.

Method for Measuring Antigen-Targeted Activity of Antibody-IFNα2b Fusion Protein Cconstructs "On target (Daudi) assay": This assay was used to quantify the anti-proliferative activity of IFNα2b and antibody-IFNα2b fusion protein constructs on cells that display both IFN receptor and the antigen targeted by the antibody to which the IFNα2b is fused. Daudi cells express both CD20 and CD38 as cell surface associated antigens, as well as cell surface IFN receptors. The viability of the Daudi cells was measured using the reagent CELLTITER-GLO®, Cat # G7570, from Promega (Madison, Wis.). This is a luminescence-based assay that determines the viability of cells in culture based on quantitation of ATP. The signal strength is proportional to the number of viable cells in a microtiter plate well. The details of the assay are as follows:

Daudi cells (obtained from ATCC, Manassas, Va.) were cultured in a T75 flask (TPP, Trasadingen, Switzerland, cat #90076) to a preferred density of between $0.5\times10^5$ and $0.8\times10^5$ viable cells/ml in RPMI 1640 (Mediatech, Inc., Manassas, Va., cat #10-040-CV) with 10% Fetal Bovine Serum (FBS; Hyclone, Logan, UT cat # SH30070.03). Cells were harvested by centrifuging at 400 g for five minutes, decanting the supernatant, and resuspending the cell pellet in RPMI 1640+10% FBS. Cells were then counted and the density was adjusted to $3.0\times10^5$ cells/ml in RPMI 1640+10% FBS. Then, 50 μl of the cell suspension was aliquoted into each well of a 96 well round bottom tissue culture plate (hereafter, "experimental plate") (TPP, cat #92067). On a separate, sterile 96 well plate (hereafter, "dilution plate"; Costar, Corning, N.Y. cat #3879), test articles were serially diluted in duplicate in RPMI 1640+10% FBS. Then, 50 μl/well was transferred from the dilution plate to the experimental plate. The experimental plate was then incubated for four days at 37° C. with 5% $CO_2$.

A mixture of the manufacturer-supplied assay buffer and assay substrate (hereafter, "CELLTITER-GLO® reagent", mixed according to the manufacturer's instructions) was added to the experimental plate at 100 μl/well. The plate was shaken for two minutes. Then, 100 μl/well was transferred from the experimental plate to a 96 well flat bottom white opaque plate (hereafter, "assay plate"; BD Biosciences, Franklin Lakes, N.J. cat #35 3296). The content of the assay plate was then allowed to stabilize in the dark for 15 minutes at room temperature. The plate was read on a Victor 3V Multilabel Counter (Perkin Elmer, Waltham, Mass., model #1420-041) on the luminometry channel and the luminescence was measured. Results are presented as "relative luminescence units (RLU)".

Data was analyzed using Prism 5 (Graphpad, San Diego, Calif.) using non-linear regression and three parameter curve fit to determine the midpoint of the curve (EC50). For each test article, potency relative to free IFNα2b (or some other form of IFN with a known potency relative to IFNα2b) was calculated as a ratio of EC50s.

One of ordinary skill in the art will appreciate that there are many other commonly used assays for measuring cell viability that could also be used.

"On target (ARP) assay" (also sometimes referred to herein as a "targeted assay"): The multiple myeloma cell line ARP-1 was a gift from Bart Barlogie M D, PhD, Director of the Myeloma Institute at the University of Arkansas Medical Center (Little Rock, Ak.). It is described in Hardin J. et al. (Interleukin-6 prevents dexamethasone-induced myeloma cell death. Blood; 84:3063, 1994). ARP-1 cells ($CD38^+$) were used to test CD38 targeting antibody-IFN fusion protein constructs. Culture and assay conditions were the same as for Daudi-based assay outlined above, with the following exceptions: ARP-1 was cultured to a density of $4.0\times10^5$ to $6.0\times10^5$ cells/ml. ARP-1 concentration was adjusted to $1.0\times10^4$ cells/ml prior to assay.

Example 1

Isoelectric Points of Anti-CD38 Antibody Attenuated IFNα2B Fusion Proteins

Various transiently transfected cells expressing an anti-CD38 antibody-attenuated IFNα2b fusion constructs (Table 2) were harvested and purified using a MABSELECT SURE® Protein A column. Samples were desalted into 200 mM Arginine, 25 mM Histidine pH 6.5 using a HiLoad Superdex 200 column.

TABLE 2

Table of Constructs

| | SEQ ID No. | | | |
|---|---|---|---|---|
| Antibody Constructs | Heavy Chain | Light Chain | IFN | VH + IFN |
| A10.21 IgG4 (S228P) IFN (A145D, T106T) | 48 | 81 | 107 | |
| A10.21 IgG4 (S228P) IFN (A145D, T106A) | 48 | 81 | 25 | 87, 31 |
| A10.21 IgG4 (S228P) IFN (A145D, ΔT106) | 48 | 81 | 110 | 61 |
| A10.21 IgG1 IFN (A145D, T106T) | 50 | 81 | 107 | |
| A10.21 IgG1 IFN (A145D, T106A) | 50 | 81 | 25 | 68 |
| A10.21 IgG1 IFN (A145D, ΔT106) | 50 | 81 | 83 | |
| A10.43 IgG4 (S228P) IFN (A145D, T106T) | 55 | 81 | 107 | |
| A10.43 IgG4 (S228P) IFN (A145D, T106A) | 55 | 81 | 25 | 74 |
| A10.21 IgG4 (S228P) IFN (A145D, T106S) | 48 | 81 | 25 | 31 |
| A10.21 IgG4 (S228P) IFN (A145D, T106V) | 48 | 81 | 25 | 31 |
| A10.21 IgG4 (S228P) IFN (A145D, T106G) | 48 | 81 | 25 | 31 |
| A10.21 IgG4 (S228P) IFN (A145D, T106E) | 48 | 81 | 25 | 31 |

TABLE 2-continued

Table of Constructs

| Antibody Constructs | SEQ ID No. Heavy Chain | Light Chain | IFN | VH + IFN |
|---|---|---|---|---|
| A10.21 IgG4 (S228P, M252Y, S254T, T256E) IFN (A145D, T106T) | 49 | 81 | 107 | |
| A10.21 IgG4 (S228P, M252Y, S254T, T256E) IFN (A145D, T106A) | 49 | 81 | 25 | 62 |
| A10.21 IgG4 (S228P) IFN (R144I T106T) | 48 | 81 | 108 | |
| A10.21 IgG4 (S228P) IFN (R144I, T106A) | 48 | 81 | 24 | 63 |
| A10.21 IgG4 (S228P) IFN (A145K, T106T) | 48 | 81 | 107 | |
| A10.21 IgG4 (S228P) IFN (A145K, T106A) | 48 | 81 | 25 | 64 |
| A10.21 IgG4 (S228P) IFN (A145G, T106T) | 48 | 81 | 107 | |
| A10.21 IgG4 (S228P) IFN (A145G, T106A) | 48 | 81 | 25 | 64 |
| A10.21 IgG4 (S228P) IFN (R33A, T106T) | 48 | 81 | 109 | |
| A10.21 IgG4 (S228P) IFN (R33A, T106A) | 48 | 81 | 13 | 65 |
| A10.21 IgG4 (S228P) IFN (A145Q, T106T) | 48 | 81 | 107 | |
| A10.21 IgG4 (S228P) IFN (A145Q, T106A) | 48 | 81 | 25 | 66 |
| A10.21 IgG1 (L235A, G237A) IFN (A145D, T106T) | 51 | 81 | 107 | |
| A10.21 IgG1 (L235A, G237A) IFN (A145D, T106A) | 51 | 81 | 25 | 69 |
| A10.21 IgG2 IFN (A145D, T106T) | 53 | 81 | 107 | |
| A10.21 IgG2 IFN (A145D, T106A) | 53 | 81 | 25 | 72 |
| A10.21 IgG2 (A330S, P331S) IFN (A145D, T106T) | | 81 | 107 | |
| A10.21 IgG2 (A330S, P331S) IFN (A145D, T106A) | | 81 | 25 | |
| A02.12 IgG4 (S228P) IFN (A145D, T106T) | 58 | 84 | 107 | |
| A02.12 IgG4 (S228P) IFN (A145D, T106A) | 58 | 84 | 25 | 77 |
| Anti-CD138 IgG4 (S228P) IFN (A145D, T106T) | 59 | 85 | 107 | |
| Anti-CD138 IgG4 (S228P) IFN (A145D, T106A) | 59 | 85 | 25 | |
| Anti-HLA IgG4 (S228P) IFN (A145D, T106T) | 60 | 86 | 107 | |
| Anti-HLA IgG4 (S228P) IFN (A145D, T106A) | 60 | 86 | 25 | |

Isoelectric focusing gels were used to determine the isoelectric point (pI) of the fusion polypeptide and to detect minor changes in the protein due to post-translational modifications such as phosphorylation and glycosylation.

Pre-cast IEF gel was setup in gel tanks ensuring a tight seal between gel and buffer. Then 200 mL of 1× Cathode buffer was poured into inner chamber ensuring no buffer enters the outer chamber. 500 mL of 1× Anode buffer was then poured into the outer chamber and filled ¾ of the tank. After the samples and ladder were loaded onto the gel, it was then run for 1 hour at 100 volt, 1 hour at 200 volt and ½ hour at 500 volt. As soon as gel run was finished, the gel was taken out and fixed in TCA solution in a glass container for 30 min. The gel was then immediately washed with deionised water 3 times. The gel was stained in SimplyBlue SafeStain (Invitrogen Life Technologies) for a full hour, and left overnight in water to destain. The final image scanned using a scanner.

The O-linked glycosylation site of the IFNα2b portion of the antibody-attenuated interferon fusion constructs was removed by either substituting the interferon's threonine 106 (T106) to alanine (shown as T106A), serine (T106S), valine (T106V), glycine (T106G) or glutamic acid (T106E) or by deleting T106 (shown as ΔT106). The effect of these changes on pI and the heterogeneity of the fusion constructs was investigated by comparing constructs with and without O-linked glycosylation by separation on IEF gels.

Figure 9:
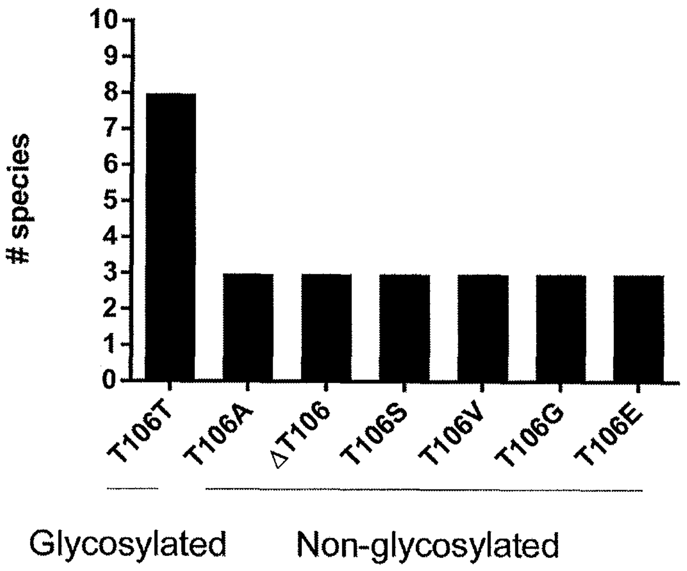
FIG. 9: Number of charged species of A10.21 anti-CD38-attenuated IFNα2b fusion proteins with (T106T) or without (T106A, ΔT106, T106S, T106V, T106G, T106E) O-linked glycosylation of the IFNα2b, as assessed by the number of bands on IEF gel.

In each case, deleting T106 or substituting T106 with alanine, serine, valine, glycine or glutamic acid decreased the number of observed charged species on an IEF gel, as evidenced by a reduced number of bands when directly compared to unmodified T106, and hence the heterogeneity of the fusion construct was reduced (FIG. 9). The reduced number of charged species on the IEF gel and therefore the reduced heterogeneity of the molecule incorporating T106S is consistent with removal of the O-linked glycosylation at residue 106 of IFNα2b.

Figure 10:
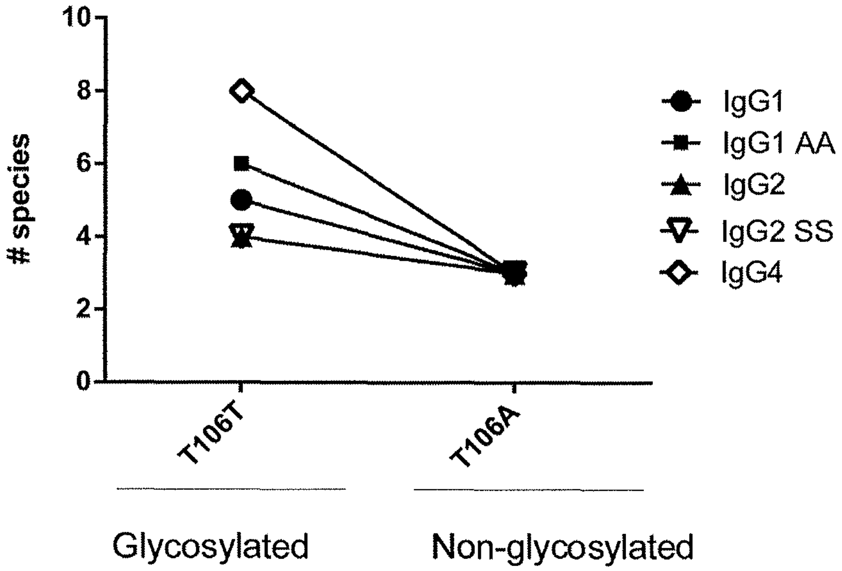
FIG. 10: Number of charged species of A10.21 anti-CD38-attenuated IFNα2b fusion proteins with (T106T) or without (T106A) O-linked glycosylation of the IFNα2b and with varying Fc isotypes, as assessed by the number of bands on IEF gel.

Removal of the O-linked glycosylation site in the attenuated IFN portion of the antibody fusion constructs resulted in an increased pI relative to O-link glycosylated proteins. Using the same antibody front-end of A10.21, this trend was consistent regardless of whether the isotype of the antibody was IgG4, IgG1, IgG1 AA (IgG1 L235A, G237A, an effector function reduced form of IgG1), IgG2 or IgG2 SS (IgG2 (A330S, P331S)) in the constructs (FIG. 10).

Figure 11:
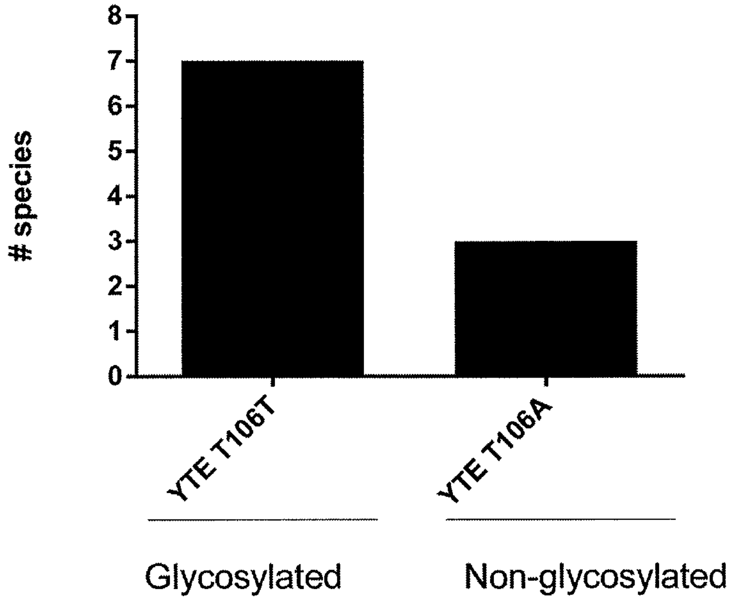
FIG. 11: Number of charged species of A10.21 (IgG4 with S228P) anti-CD38-attenuated IFNα2b fusion proteins with (T106T) or without (T106A) O-linked glycosylation of the IFNα2b in the presence of YTE substitutions in the antibody constant region, as assessed by the number of bands on IEF gel.

YTE substitutions (M252Y, S254T, T256E) have been shown to confer increased affinity to FcRn, presumably increasing the half-life of antibodies. Further experiments examined whether substitutions in other parts of the antibody IFN fused constructs will affect the reduced heterogeneity which resulted from a T106 deletion or substitution. The heterogeneity of glycosylated A10.21 anti-CD38-attenuated IFNα2b fusion construct (YTE, T106T) and the non-glycosylated IFN fusion construct with the YTE substitutions (YTE, T106A) was assessed on IEF gels. Removal of glycosylation of the IFNα2b component of fusion constructs bearing the YTE mutations decreased heterogeneity (FIG. 11).

Figure 12:
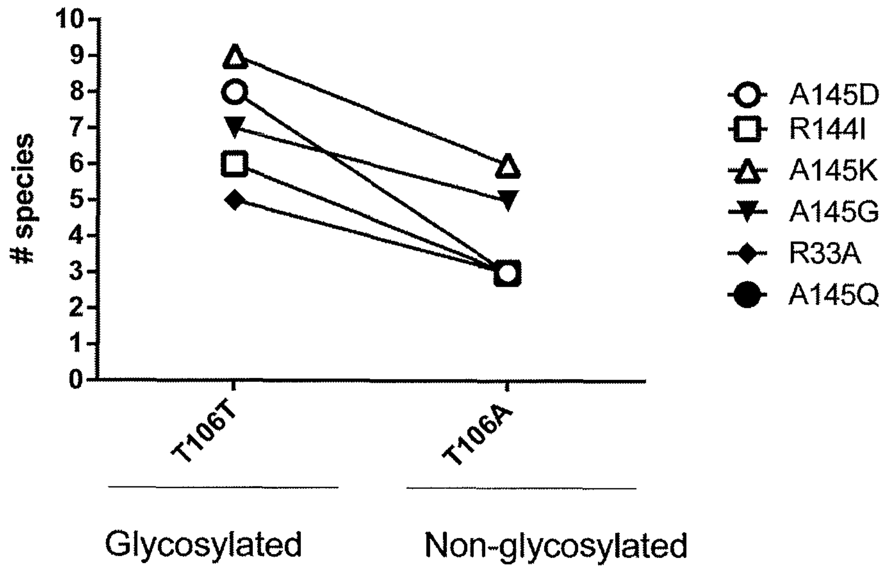
FIG. 12: Number of charged species of A10.21 (IgG4 with S228P) anti-CD38-attenuated IFNα2b fusion proteins with (T106T) or without (T106A) O-linked glycosylation of the IFNα2b in the presence of a variety of IFN attenuating substitutions, as assessed by the number of bands on IEF gel.

Attenuation of IFNα2b is attained by substitutions of key amino acid residues which are responsible for binding to IFN receptors. The number of charged species of A10.21 IgG4 (S228P) IFN constructs with various attenuating amino acid substitutions in the IFNα2b, together with (T106T) or without O-linked glycosylation (T106A) of the IFNα2b component was evaluated. Individual amino acid residues Arginine-33, Arginine-144 and Alanine-145 of IFNα2b were substituted one at a time with Alanine for residue 33 (R33A), Isoleucine for residue 144 (R144I) or Lysine, Glycine or Glutamine for residue 145 (A145K, A145G, A145Q). When directly compared the aglycosylated IFN fusion constructs were consistently less heterogeneous than their glycosylated counterparts (FIG. 12).

Figure 13:
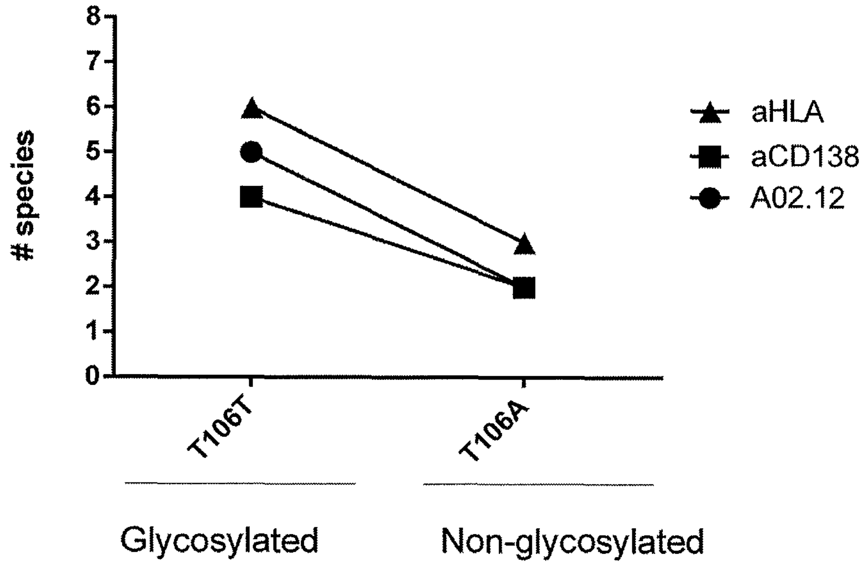
FIG. 13: Number of charged species of antibodies with differing target specificities; anti-CD138 antibody, anti-HLA antibody and anti-CD38 antibody (A02.12) (all IgG4 with S228P) fused to attenuated IFNα2b with (T106T) or without (T106A) O-linked glycosylation of the IFNα2b, as assessed by the number of bands on IEF gel.

The reduction in heterogeneity exhibited was independent of the antibody portion of the construct. Removal of the O-linked glycosylation site in the attenuated IFNα2b portion of the antibody (IgG4 (S228P))-attenuated IFN fusion constructs with specificity against HLA, CD138 and CD38 (a different epitope on CD38 to antibody A10.21-antibody A02.12) also resulted in a decrease in heterogeneity (FIG. 13) as detected by IEF.

Example 2

Anti-Proliferative Activity of Antibody Attenuated Interferonα2b Fusion Proteins The anti-proliferative effects of IFNα2b consist of direct and indirect activities. Direct activity occurs through cancer cell growth inhibition by cell cycle arrest (Matsui et al. 2003), apoptosis by death receptor-dependent (Crowder et al. 2005) and -independent (Otsuki et al. 1998) pathways, or differentiation (Matsui et al. 2003). Target-specific direct cytotoxicity of antibody attenuated interferon fusion proteins were measured against target positive cell lines using a luminescent cell viability assay.

Anti CD38-IFN Lead Sequence Samples

The constructs (Table 3) were either stably cloned or transiently transfected and were harvested and purified using a MABSELECT SURE® Protein A column. Samples were desalted into 200 mM Arginine, 25 mM Histidine pH 6.5 using a HiLoad Superdex 200 column.

TABLE 3

Table of Constructs

| | Seq Id No. | | | |
|---|---|---|---|---|
| Antibody Constructs | Heavy Chain | Light Chain | IFN | VH + IFN |
| A10.21 IgG4 (S228P) IFN (A145D, T106T) | 48 | 81 | 107 | |
| A10.21 IgG4 (S228P) IFN (A145D, T106A) | 48 | 81 | 25 | 87, 31 |
| A10.21 IgG4 (S228P) IFN (A145D, ΔT106) | 48 | 81 | 110 | 61 |
| A10.21 IgG4 (S228P) IFN (A145D, T106S) | 48 | 81 | 25 | 31 |
| A10.21 IgG4 (S228P) IFN (A145D, T106V) | 48 | 81 | 25 | 31 |
| A10.21 IgG4 (S228P) IFN (A145D, T106G) | 48 | 81 | 25 | 31 |
| A10.21 IgG4 (S228P) IFN (A145D, T106E) | 48 | 81 | 25 | 31 |
| A10.21 IgG4 (S228P, M252Y, S254T, T256E) IFN (A145D, T106T) | 49 | 81 | 107 | |
| A10.21 IgG4 (S228P, M252Y, S254T, T256E) IFN (A145D, T106A) | 49 | 81 | 25 | 62 |
| A10.21 IgG4 (S228P) IFN (R144I T106T) | 48 | 81 | 108 | |
| A10.21 IgG4 (S228P) IFN (R144I, T106A) | 48 | 81 | 24 | 63 |
| A10.21 IgG4 (S228P) IFN (A145K, T106T) | 48 | 81 | 107 | |
| A10.21 IgG4 (S228P) IFN (A145K, T106A) | 48 | 81 | 25 | 64 |
| A10.21 IgG4 (S228P) IFN (A145G, T106T) | 48 | 81 | 107 | |
| A10.21 IgG4 (S228P) IFN (A145G, T106A) | 48 | 81 | 25 | 64 |
| A10.21 IgG4 (S228P) IFN (R33A, T106T) | 48 | 81 | 109 | |
| A10.21 IgG4 (S228P) IFN (R33A, T106A) | 48 | 81 | 13 | 65 |
| A10.21 IgG4 (S228P) IFN (A145Q, T106T) | 48 | 81 | 107 | |
| A10.21 IgG4 (S228P) IFN (A145Q, T106A) | 48 | 81 | 25 | 66 |
| A10.21 IgG4 (S228P) IFN (A145N, T106T) | 48 | 81 | 107 | |
| A10.21 IgG4 (S228P) IFN (A145N, T106A) | 48 | 81 | 25 | 66 |
| A10.21 IgG4 (S228P) IFN (R144N, T106T) | 48 | 81 | 108 | |
| A10.21 IgG4 (S228P) IFN (R144N, T106A) | 48 | 81 | 24 | 67 |
| A10.21 IgG4 (S228P) IFN (R144H, T106T) | 48 | 81 | 108 | |
| A10.21 IgG4 (S228P) IFN (R144H, T106A) | 48 | 81 | 24 | 67 |
| A10.21 IgG1 IFN (A145D, T106T) | 50 | 81 | 107 | |
| A10.21 IgG1 IFN (A145D, T106A) | 50 | 81 | 25 | 68 |
| A10.21 IgG1 IFN (A145D, ΔT106) | 50 | 81 | 110 | 83 |
| A10.21 IgG1 (L235A, G237A) IFN (A145D, T106T) | 51 | 81 | 107 | |
| A10.21 IgG1 (L235A, G237A) IFN (A145D, T106A) | 51 | 81 | 25 | 69 |
| A10.21 IgG1 (L235A, G237A, M252Y, S254T, T256E) IFN (A145D, T106T) | 52 | 81 | 107 | |
| A10.21 IgG1 (L235A, G237A, M252Y, S254T, T256E) IFN (A145D, T106A) | 52 | 81 | 25 | |
| A10.21 IgG1 (M252Y, S254T, T256E) IFN (A145D, T106T) | 52 | 81 | 107 | |
| A10.21 IgG1 (M252Y, S254T, T256E) IFN (A145D, T106A) | | 81 | 25 | 70 |
| A10.21 IgG2 IFN (A145D, T106T) | 53 | 81 | 107 | |
| A10.21 IgG2 IFN (A145D, T106A) | 53 | 81 | 25 | 72 |
| A10.21 IgG2 (A330S, P331S) IFN (A145D, T106T) | | 81 | 107 | |
| A10.21 IgG2 (A330S, P331S) IFN (A145D, T106A) | | 81 | 25 | |
| A10.21 IgG2 (M252Y, S254T, T256E) IFN (A145D, T106T) | 54 | 81 | 107 | |
| A10.21 IgG2 (M252Y, S254T, T256E) IFN (A145D, T106A) | 54 | 81 | 25 | 73 |
| A10.43 IgG4 (S228P) IFN (A145D, T106T) | 55 | 81 | 107 | |
| A10.43 IgG4 (S228P) IFN (A145D, T106A) | 55 | 81 | 25 | 74 |
| R10A2 IgG4 (S228P) IFN (A145D, T106T) | 75 | 82 | 107 | |
| R10A2 IgG4 (S228P) IFN (A145D, T106A) | 75 | 82 | 25 | |
| R10A2 IgG4 (S228P) IFN (A145D, T106R) | 75 | 82 | 25 | |
| R10A2 IgG4 (S228P) IFN (A145D, T106N) | 75 | 82 | 25 | |
| R10A2 IgG4 (S228P) IFN (A145D, T106D) | 75 | 82 | 25 | |
| R10A2 IgG4 (S228P) IFN (A145D, T106C) | 75 | 82 | 25 | |
| R10A2 IgG4 (S228P) IFN (A145D, T106E) | 75 | 82 | 25 | |
| R10A2 IgG4 (S228P) IFN (A145D, T106Q) | 75 | 82 | 25 | |
| R10A2 IgG4 (S228P) IFN (A145D, T106G) | 75 | 82 | 25 | |
| R10A2 IgG4 (S228P) IFN (A145D, T106H) | 75 | 82 | 25 | |
| R10A2 IgG4 (S228P) IFN (A145D, T106I) | 75 | 82 | 25 | |
| R10A2 IgG4 (S228P) IFN (A145D, T106L) | 75 | 82 | 25 | |
| R10A2 IgG4 (S228P) IFN (A145D, T106K) | 75 | 82 | 25 | |
| R10A2 IgG4 (S228P) IFN (A145D, T106M) | 75 | 82 | 25 | |
| R10A2 IgG4 (S228P) IFN (A145D, T106F) | 75 | 82 | 25 | |
| R10A2 IgG4 (S228P) IFN (A145D, T106P) | 75 | 82 | 25 | |
| R10A2 IgG4 (S228P) IFN (A145D, T106S) | 75 | 82 | 25 | |
| R10A2 IgG4 (S228P) IFN (A145D, T106W) | 75 | 82 | 25 | |
| R10A2 IgG4 (S228P) IFN (A145D, T106Y) | 75 | 82 | 25 | |
| R10A2 IgG4 (S228P) IFN (A145D, T106V) | 75 | 82 | 25 | |
| A02.12 IgG4 (S228P) IFN (A145D, T106T) | 58 | 84 | 107 | |
| A02.12 IgG4 (S228P) IFN (A145D, T106A) | 58 | 84 | 25 | 77 |
| OPG-Fc (IgG2) IFN (A145D, T106T) | 57 | | 107 | |
| OPG-Fc (IgG2) IFN (A145D, T106A) | 57 | | 25 | 78 |
| Anti-CD138 IgG4 (S228P) IFN (A145D, T106T) | 59 | 85 | 107 | |
| Anti-CD138 IgG4 (S228P) IFN (A145D, T106A) | 59 | 85 | 25 | |
| Anti-HLA IgG4 (S228P) IFN (A145D, T106T) | 60 | 86 | 107 | |

TABLE 3-continued

| Table of Constructs | | | | |
|---|---|---|---|---|
| | Seq Id No. | | | |
| Antibody Constructs | Heavy Chain | Light Chain | IFN | VH + IFN |
| Anti-HLA IgG4 (S228P) IFN (A145D, T106A) | 60 | 86 | 25 | |

Commercial IFNα2b

INTRON® A, a commercial bacterially produced IFNα2b from Schering-Plough, was used as a positive control.

Anti-Proliferative Activity Measurement

Anti-proliferative activity was measured using the methods described above "Daudi cell proliferation assay" and "ARP-1 Cell proliferation assay". The ARP-1 cell proliferation assay method was used with an additional cell line NCI-H929 for the measurement of the anti-proliferative activity of antibody-attenuated IFNα2b fusion protein. In some experiments the plates were read on a dedicated GLOMAX® 96 Microplate Luminometer and CELLTITER-GLO® 2.0 reagents were used instead of the original CELLTITER-GLO®, neither of which impacted the results. The ARP-1/NCI-H929 or Daudi cell proliferation assay was used to quantify the anti-proliferative activity of IFNs and antibody-attentuated IFNα2b fusion protein constructs on cells that display CD38. Daudi, ARP1 and NCI-H929 cells express CD38 as a cell surface associated antigen. The details of the assays are as follows.

In the ARP-1/NCI-H929 cell proliferation assay viability of cells was measured using the reagent CELLTITER-GLO® 2.0, Cat # G9242, from Promega (Madison, Wis.). This is a luminescence-based assay that determines the viability of cells in culture based on quantitation of ATP. The signal strength is proportional to the number of viable cells in a microtiter plate well. Cells (NCI-H929 from ATCC, Manassas, Va. and ARP-1, a gift from Bart Barlogie M D, PhD, Director of the Myeloma Institute at the University of Arkansas Medical Center; Little Rock, Ak.) were cultured in a T75 flask (TPP, Trasadingen, Switzerland, cat #90076) to a preferred density of between $0.5\times10^5$ and $0.8\times10^5$ viable cells/mL in RPMI 1640 (Mediatech, Inc., Manassas, Va., cat #10-040-CV) with 10% Fetal Bovine Serum (FBS; Hyclone, Logan, Utah cat # SH30070.03). Cells were harvested by centrifuging at 400×g for five minutes, decanting the supernatant, and resuspending the cell pellet in RPMI 1640+10% FBS. Cells were then counted and the density was adjusted to $3.0\times10^5$ cells/mL in RPMI 1640+10% FBS. 504 of cell suspension was seeded into each well of a 96 well round bottom tissue culture plate (hereafter, "experimental plate") (TPP, cat #92067). Cells were incubated at 4° C. for 1 hour prior to the addition of test compounds. On a separate, sterile 96 well plate (hereafter, "dilution plate"; Costar, Corning, N.Y. cat #3879), test articles were serially diluted in duplicate in RPMI 1640+10% FBS. 50 μL/well was transferred from the dilution plate to the experimental plate. The experimental plate was then incubated for four days at 37° C. with 5% $CO_2$. A "CELLTITER-GLO® reagent 2.0", was added to the experimental plate at 100 μL/well. The plate was shaken for two minutes. 100 μL/well was transferred from the experimental plate to a 96 well flat bottom white opaque plate (hereafter, "assay plate"; BD Biosciences, Franklin 5 Lakes, N.J. cat #35 3296). The content of the assay plate was then allowed to stabilize in the dark for 15 minutes at room temperature. The plate was read on GLOMAX® 96 Microplate Luminometer. Results are presented as "relative luminescence units" (RLU).

Data was analyzed using Prism 5 (Graphpad, San Diego, Calif.) using non-linear regression and four parameter curve fit to determine the IC50.

The O-linked glycosylation site of anti-CD38 antibody attenuated interferon fusion constructs were removed by either substituting threonine 106 (T106) to alanine (T106A), serine (T106S), valine (T106V), glycine (T106G) or glutamic acid (T106E) or deleting T106 (shown as ΔT106). The effect on cell proliferation was investigated by comparing A10.21 anti-CD38 antibody fused to attenuated IFNα2b with and without O-linked glycosylation. Removal of the O-linked glycosylation site in the attenuated IFN portion of the antibody fusion constructs resulted in increased anti-proliferative activity as shown by lower IC50 (nM) relative to the corresponding O-linked glycosylated fusion proteins i.e. A10.21 IgG4 (S228P) IFN (A145D, T106T) and A10.21 IgG1 IFN (A145D, T106T) in both ARP1 (FIG. 1A) and NCI-H929 cells (FIG. 1B). This trend was consistent regardless of whether the antibody isotype was IgG4 and IgG1.

Figure 14:
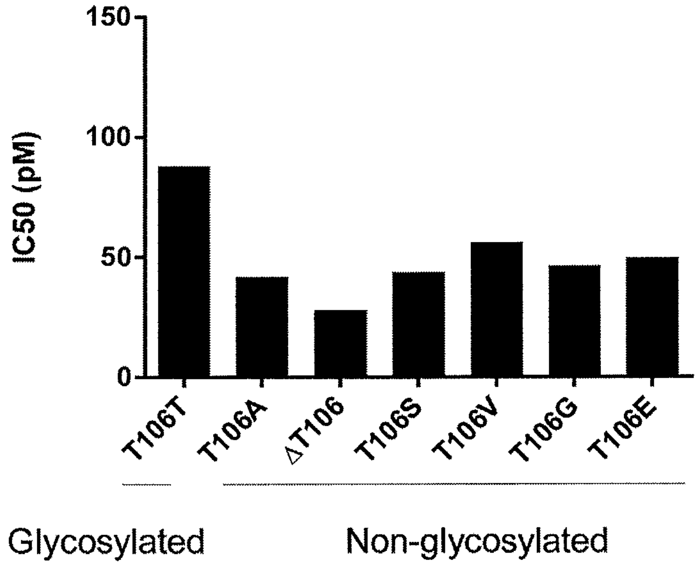
FIG. 14: "On-target" activities of anti-CD38-attenuated IFNα2b fusion proteins (A10.21 IgG4 (S228P) IFN (A145D)) with (T106T) and without (T106A, ΔT106, T106S, T106V, T106G, T106E) O-linked glycosylation of the IFNα2b.

Substitution of threonine 106 (T106) to alanine (T106A), serine (T106S), valine (T106V), glycine (T106G) or glutamic acid (T106E) resulted in increased anti-proliferative activity as shown by lower IC50 (nM) relative to O-linked glycosylated fusion proteins. All non-glycosylated constructs showed higher "on-target" potency relative to their glycosylated counterpart in NCI-H929 cells (FIG. 14).

The impact on anti-proliferative activity of the removal of the O-linked glycosylation site from the attenuated IFNα2b component was examined in a range of anti-CD38 antibody-attenuated IFNα2b fusion proteins. Variants of the anti-CD38 antibody-attenuated IFNα2b fusion protein R10A2 IgG4 (S228P) IFN (A145D) possessing different amino acid substitutions at T106 to remove the O-linked glycosylation site on the IFN component (T106A, T106G, T106N, T106F, T106R, T106D, T106E, T106Q, T106H, T1061, T106L, T106K, T106M, T106F, T106P, T106S, T106V, T106Y and T106W, (Table 4) were examined and the results shown in FIG. 2.

While the level of potency varied between different substitutions at the T106 site, all substitutions that are predicted to result in the removal of O-linked glycosylation increased potency relative to the corresponding O-linked glycosylated protein (FIG. 2).

TABLE 4

R10A2 Anti-CD38 antibody-attenuated IFN fusion construct variants with various amino acid substitutions at T106 for removal of O-linked glycosylation.

| | Seq Id No. | | |
|---|---|---|---|
| Construct Name | Heavy Chain | Light Chain | IFN |
| R10A2 IgG4 (S228P) IFN (A145D, T106T) | 75 | 82 | 107 |
| R10A2 IgG4 (S228P) IFN (A145D, T106A) | 75 | 82 | 25 |
| R10A2 IgG4 (S228P) IFN (A145D, T106R) | 75 | 82 | 25 |
| R10A2 IgG4 (S228P) IFN (A145D, T106N) | 75 | 82 | 25 |
| R10A2 IgG4 (S228P) IFN (A145D, T106D) | 75 | 82 | 25 |
| R10A2 IgG4 (S228P) IFN (A145D, T106C) | 75 | 82 | 25 |
| R10A2 IgG4 (S228P) IFN (A145D, T106E) | 75 | 82 | 25 |
| R10A2 IgG4 (S228P) IFN (A145D, T106Q) | 75 | 82 | 25 |
| R10A2 IgG4 (S228P) IFN (A145D, T106G) | 75 | 82 | 25 |
| R10A2 IgG4 (S228P) IFN (A145D, T106H) | 75 | 82 | 25 |
| R10A2 IgG4 (S228P) IFN (A145D, T106I) | 75 | 82 | 25 |
| R10A2 IgG4 (S228P) IFN (A145D, T106L) | 75 | 82 | 25 |

TABLE 4-continued

R10A2 Anti-CD38 antibody-attenuated IFN fusion construct variants with various amino acid substitutions at T106 for removal of O-linked glycosylation.

| Construct Name | Seq Id No. Heavy Chain | Light Chain | IFN |
|---|---|---|---|
| R10A2 IgG4 (S228P) IFN (A145D, T106K) | 75 | 82 | 25 |
| R10A2 IgG4 (S228P) IFN (A145D, T106M) | 75 | 82 | 25 |
| R10A2 IgG4 (S228P) IFN (A145D, T106F) | 75 | 82 | 25 |
| R10A2 IgG4 (S228P) IFN (A145D, T106P) | 75 | 82 | 25 |
| R10A2 IgG4 (S228P) IFN (A145D, T106S) | 75 | 82 | 25 |
| R10A2 IgG4 (S228P) IFN (A145D, T106W) | 75 | 82 | 25 |
| R10A2 IgG4 (S228P) IFN (A145D, T106Y) | 75 | 82 | 25 |
| R10A2 IgG4 (S228P) IFN (A145D, T106V) | 75 | 82 | 25 |

Figure 15:
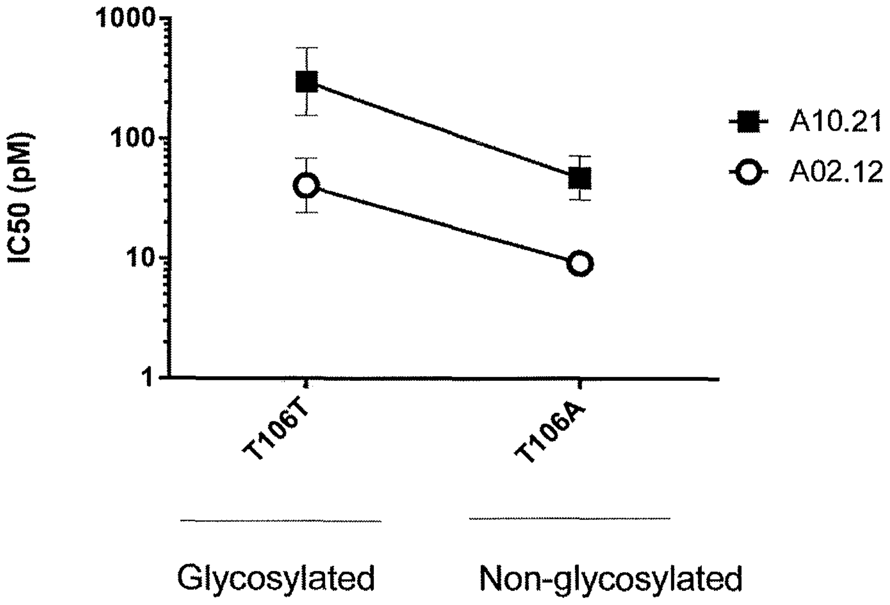
FIG. 15: "On-target" activities of two different anti-CD38 antibody-attenuated IFNα2b fusion proteins (A02.12 and A10.21, both IgG4 with S228P) which bind different epitopes on CD38 with (T106T) or without (T106A) O-linked glycosylation of the IFNα2b.

The relative changes in the potency between two different anti-CD38 antibody interferon fusion proteins (A02.12 and A10.21) which bind different epitopes on CD38, with or without the O-linked glycosylation (A02.12 IgG4 (S228P) IFN (A145D, T106T), A02.12 IgG4 (S228P) IFN (A145D, T106A), A10.21 IgG4 (S228P) IFN (A145D, T106T) and A10.21 IgG4 (S228P) IFN (A145D, T106A) was assessed in a similar manner. Removal of the O-linked glycosylation site in the attenuated IFN portion of the antibody (IgG4 (S228P)) fusion constructs with differing specificity against CD38 resulted in an increase in anti-proliferative activity regardless of the target of the antibody portion of the construct (FIG. 15).

Figure 16:
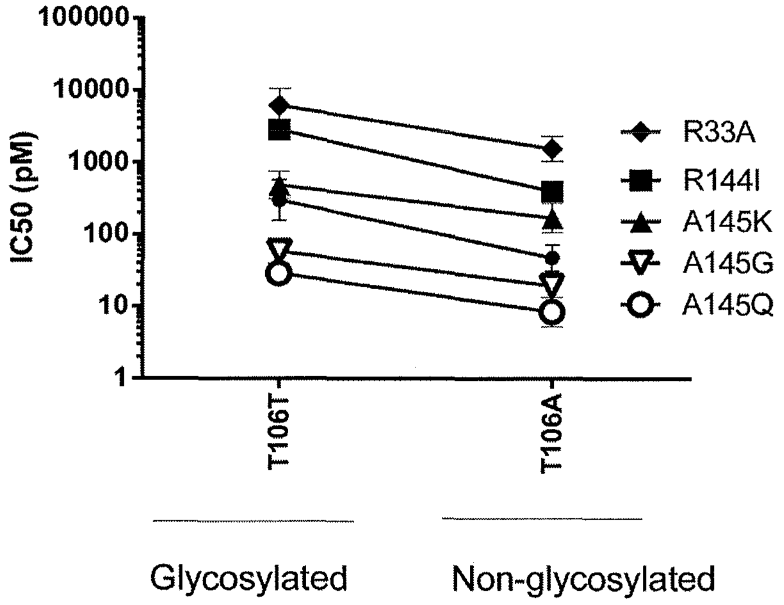
FIG. 16: "On-target" activities of A10.21 anti-CD38-attenuated IFNα2b fusion proteins (A10.21 IgG4 (S228P) IFN) with (T106T) and without (T106A) O-linked glycosylation of the IFNα2b, with a variety of IFN attenuating substitutions (R33A, R144I, R145Q, A145K or A145G).

Attenuation of IFNα2b is achieved by various attenuating substitutions. The anti-proliferative activity of A10.21 IgG4 (S228P) IFN constructs with various attenuating substitutions in the IFNα2b with (T106T) and without O-linked glycosylation (T106A) (Table 5) was also evaluated. The removal of the O-linked glycosylation site in the IFNα2b component of constructs with various attenuating substitutions all had higher potency than their glycosylated counterpart (FIG. 16).

TABLE 5

A10.21 IgG4 (S228P) IFN constructs with various attenuating substitutions in the IFNα2b with (T106T) and without O-linked glycosylation (T106A).

| Construct Name | Seq Id No. Heavy Chain | Light Chain | IFN | VH + IFN |
|---|---|---|---|---|
| A10.21 IgG4 (S228P) IFN (R144I T106T) | 48 | 81 | 108 | |
| A10.21 IgG4 (S228P) IFN (R144I, T106A) | 48 | 81 | 24 | 63 |
| A10.21 IgG4 (S228P) IFN (A145K, T106T) | 48 | 81 | 107 | |
| A10.21 IgG4 (S228P) IFN (A145K, T106A) | 48 | 81 | 25 | 64 |
| A10.21 IgG4 (S228P) IFN (A145G, T106T) | 48 | 81 | 107 | |
| A10.21 IgG4 (S228P) IFN (A145G, T106A) | 48 | 81 | 25 | 64 |
| A10.21 IgG4 (S228P) IFN (R33A, T106T) | 48 | 81 | 109 | |
| A10.21 IgG4 (S228P) IFN (R33A, T106A) | 48 | 81 | 13 | 65 |
| A10.21 IgG4 (S228P) IFN (A145Q, T106T) | 48 | 81 | 107 | |
| A10.21 IgG4 (S228P) IFN (A145Q, T106A) | 48 | 81 | 25 | 66 |

TABLE 5-continued

A10.21 IgG4 (S228P) IFN constructs with various attenuating substitutions in the IFNα2b with (T106T) and without O-linked glycosylation (T106A).

| Construct Name | Seq Id No. Heavy Chain | Light Chain | IFN | VH + IFN |
|---|---|---|---|---|
| A10.21 IgG4 (S228P) IFN (A145N, T106T) | 48 | 81 | 107 | |
| A10.21 IgG4 (S228P) IFN (A145N, T106A) | 48 | 81 | 25 | 66 |
| A10.21 IgG4 (S228P) IFN (R144N, T106T) | 48 | 81 | 108 | |
| A10.21 IgG4 (S228P) IFN (R144N, T106A) | 48 | 81 | 24 | 67 |
| A10.21 IgG4 (S228P) IFN (R144H, T106T) | 48 | 81 | 108 | |
| A10.21 IgG4 (S228P) IFN (R144H, T106A) | 48 | 81 | 24 | 67 |

To investigate whether other attenuated IFNα2b fused antibodies/proteins which have different binding targets have modulated anti-proliferative activity as a result of removal of O-linked glycosylation, 2 constructs were created (an anti-CD138 antibody and an anti-HLA antibody and fused to IFN (A145D) with or without O-linked glycosylation (Table 6) and were tested for anti-proliferative activity.

Figure 17:
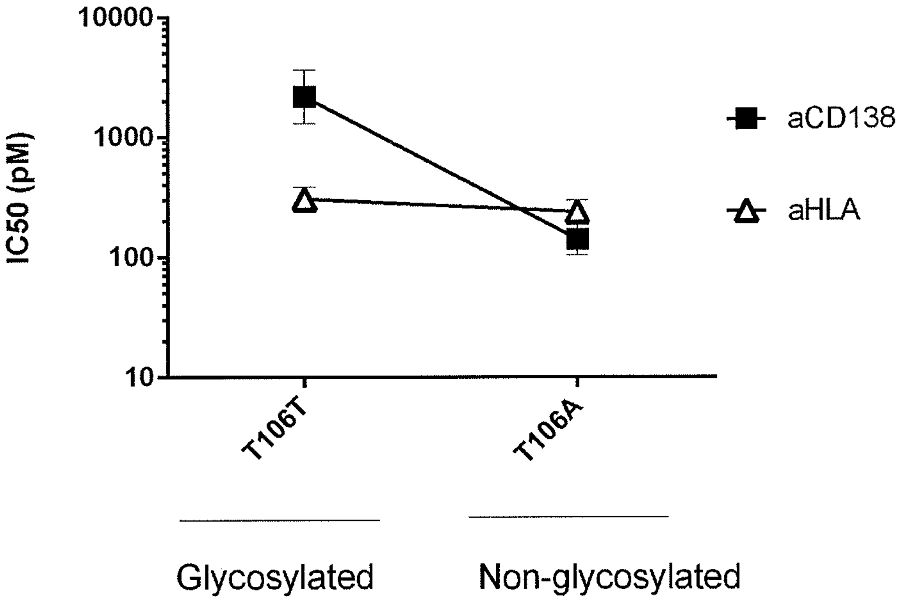
FIG. 17: "On-target" activities of antibodies with differing target specificities; anti-CD138 antibody and anti-HLA antibody (both IgG4 with S228P) fused to attenuated IFNα2b with (T106T) or without (T106A) O-linked glycosylation of the IFNα2b.

Removal of the O-linked glycosylation site in the attenuated IFN portion of the antibody (IgG4 (S228P)) fusion constructs with specificity against HLA and CD138 resulted in an increase in anti-proliferative activity regardless of the target of the antibody portion of the construct. This was demonstrated in antibody fusion constructs against HLA and CD138 (FIG. 17).

TABLE 6

Constructs of various IFN fusion proteins-anti-CD138 antibody and anti-HLA antibody fused to IFN (A145D) with or without O-linked glycosylation

| Antibody Constructs | Seq Id No. Heavy Chain | Light Chain | IFN | VH + IFN |
|---|---|---|---|---|
| Anti-CD138 IgG4 (S228P) IFN (A145D, T106T) | 59 | 85 | 107 | 59 |
| Anti-CD138 IgG4 (S228P) IFN (A145D, T106A) | 59 | 85 | 25 | 59 |
| Anti-HLA IgG4 (S228P) IFN (A145D, T106T) | 60 | 86 | 107 | |
| Anti-HLA IgG4 (S228P) IFN (A145D, T106A) | 60 | 86 | 25 | |

Effect on Anti Proliferative Activity of the Removal of O-linked Glycosylation From Fusion Proteins Comprising Substitutions in the Fc Regions for Half-Life Extension or Reduced Effector Function YTE substitutions have been shown to confer increased affinity to FcRn, presumably increasing the half-life of antibodies. IFN fused antibodies containing the YTE substitutions were tested for anti-proliferative activity in the presence and absence of O-linked glycosylation. The following variants were made of the A10.21 anti-CD38 antibody attenuated IFN fusion protein (Table 7).

Figure 18:
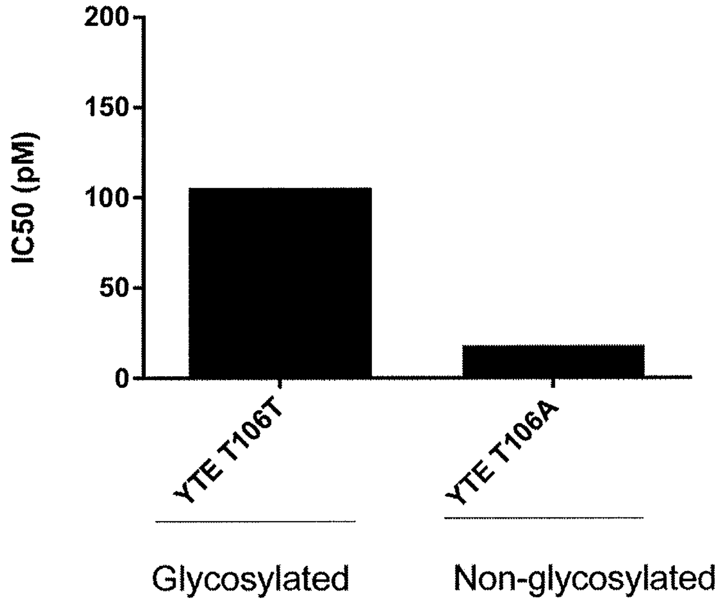
FIG. 18: "On-target" activities of A10.21 anti-CD38-attenuated IFNα2b fusion proteins (A10.21 IgG4 (S228P) IFN (A145D)) with (T106T) and without (T106A) O-linked glycosylation of the IFNα2b, in the presence of YTE substitution in the antibody heavy chain.

The introduction of the YTE substitution to A10.21 IgG4 (S228P) (A145D, T106A) did not impact the increase in potency caused by removal of the O-linked glycosylation from the attenuated IFN (FIG. 18).

Figure 19:
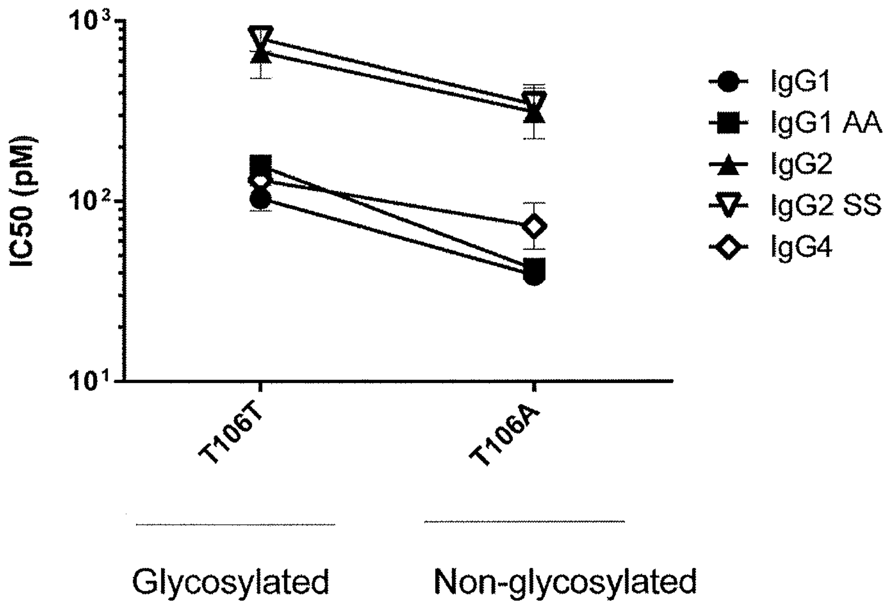
FIG. 19: "On-target" activities of A10.21 anti-CD38-attenuated IFNα2b (A145D) fusion proteins with (T106T) and without (T106A) O-linked glycosylation of the IFNα2b, with with a variety of immunoglobulin Fc isotypes.

L235A and G237A substitutions in the Fc portion of IgG1 variants and A330S and P331S substitutions in the Fc portion of IgG2 variants results in reduced effector function. Attenuated IFN fused IgG1 antibodies containing L235A and G237A substitutions and attenuated IFN fused IgG2 antibodies containing A330S and P331S substitutions were tested for anti-proliferative activity in the presence and absence of O-linked glycosylation. These variants were made of the A10.21 anti-CD38 antibody attenuated IFN fusion protein (Table 7). Removal of the O-linked glycosylation site in the attenuated IFN portion of the antibody fusion constructs resulted in an increase in potency regardless of whether the isotype of the antibody in the antibody constructs was IgG1 or IgG1 AA (IgG1 (L235A, G237A)), IgG2 or IgG2 SS (IgG2 (A330S, P331S)) (FIG. 19).

TABLE 7

A10.21 fusion proteins composed of substitutions in the Fc regions for half-life extension or reduced effector function

| | Seq Id No. | | | |
|---|---|---|---|---|
| Antibody Constructs | Heavy Chain | Light Chain | IFN | VH + IFN |
| A10.21 IgG4 (S228P, M252Y, S254T, T256E) IFN (A145D, T106T) | 49 | 81 | 107 | |
| A10.21 IgG4 (S228P, M252Y, S254T, T256E) IFN (A145D, T106A) | 49 | 81 | 25 | 62 |
| A10.21 IgG1 (L235A, G237A) IFN (A145D, T106T) | 51 | 81 | 107 | |
| A10.21 IgG1 (L235A, G237A) IFN (A145D, T106A) | 51 | 81 | 25 | 69 |
| A10.21 IgG1 (L235A, G237A, M252Y, S254T, T256E) IFN (A145D, T106T) | 52 | 81 | 107 | |
| A10.21 IgG1 (L235A, G237A, M252Y, S254T, T256E) IFN (A145D, T106A) | 52 | 81 | 25 | |
| A10.21 IgG1 (M252Y, S254T, T256E) IFN (A145D, T106T) | 52 | 81 | 107 | |
| A10.21 IgG1 (M252Y, S254T, T256E) IFN (A145D, T106A) | 111 | 81 | 25 | 70 |
| A10.21 IgG2 IFN (A145D, T106T) | 53 | 81 | 107 | |
| A10.21 IgG2 IFN (A145D, T106A) | 53 | 81 | 25 | 72 |
| A10.21 IgG2 (A330S, P331S) IFN (A145D, T106T) | 81 | 112 | 107 | |
| A10.21 IgG2 (A330S, P331S) IFN (A145D, T106A) | 112 | 81 | 25 | |
| A10.21 IgG2 (M252Y, S254T, T256E) IFN (A145D, T106T) | 54 | 81 | 107 | |
| A10.21 IgG2 (M252Y, S254T, T256E) IFN (A145D, T106A) | 54 | 81 | 25 | 73 |

Removal of the O-linked glycosylation site from the attenuated interferon portion of the anti-CD38 antibody interferon fusion proteins by amino acid substitution or deletion of T106 resulted in an increase in anti-proliferative activity on target CD38, CD138 or HLA positive cells (1.3-12 fold).

Example 3

On/Off Target Activity of Antibody-Attenuated IFNα2b Fusion Proteins

The iLite™ reporter gene assay was performed for the quantitative determination of Human Interferon Alpha (IFNα2b) bioactivity (IU/ml) using luciferase generated-bioluminescence. The cells used in this assay express CD38 and were used to measure the 'ON-target' activity of anti-CD38-attenuated IFNα2b fusion proteins. These cells can also be used to measure 'OFF-target' activity when CD38 is blocked with an anti-CD38 antibody recognizing the same epitope. These assays can be used to determine the Selectivity Index (SI) which is a measure of how selectively active anti-CD38 IFN fusion proteins are against CD38+ target cells and non-active on cells where CD38 is blocked (mimicking $CD38^-$ cells). The larger the SI the more selective the agents are against the target, while a number close to 1 indicates that there is no selectivity against the target or non-target. Intron A was used as a positive control as it is active against cells that express interferon alpha receptors, IFNAR1/2 but not selective against other cell surface expressed antigens (i.e. CD38) having an SI of approximately 1.

Antibody-Attenuated IFN Constructs

The sequences for the constructs used are set out in Sequence Listing and are listed in the following Table 8.

TABLE 8

| | Seq Id No. | | | |
|---|---|---|---|---|
| Antibody Constructs | Heavy Chain | Light Chain | IFN | VH + IFN |
| A10.21 IgG4 (S228P) IFN (A145D, T106T) | 48 | 81 | 107 | |
| A10.21 IgG4 (S228P) IFN (A145D, T106A) | 48 | 81 | 25 | 87, 31 |
| A10.21 IgG4 (S228P) IFN (A145D, ΔT106) | 48 | 81 | 110 | 61 |
| A10.21 IgG4 (S228P) IFN (A145D, T106S) | 48 | 81 | 25 | 31 |
| A10.21 IgG4 (S228P) IFN (A145D, T106V) | 48 | 81 | 25 | 31 |
| A10.21 IgG4 (S228P) IFN (A145D, T106G) | 48 | 81 | 25 | 31 |
| A10.21 IgG4 (S228P) IFN (A145D, T106E) | 48 | 81 | 25 | 31 |
| A10.21 IgG4 (S228P, M252Y, S254T, T256E) IFN (A145D, T106T) | 49 | 81 | 107 | |
| A10.21 IgG4 (S228P, M252Y, S254T, T256E) IFN (A145D, T106A) | 49 | 81 | 25 | 62 |
| A10.21 IgG4 (S228P) IFN (R144I T106T) | 48 | 81 | 108 | |
| A10.21 IgG4 (S228P) IFN (R144I, T106A) | 48 | 81 | 24 | 63 |
| A10.21 IgG4 (S228P) IFN (A145K, T106T) | 48 | 81 | 107 | |
| A10.21 IgG4 (S228P) IFN (A145K, T106A) | 48 | 81 | 25 | 64 |
| A10.21 IgG4 (S228P) IFN (A145G, T106T) | 48 | 81 | 107 | |
| A10.21 IgG4 (S228P) IFN (A145G, T106A) | 48 | 81 | 25 | 64 |
| A10.21 IgG4 (S228P) IFN (R33A, T106T) | 48 | 81 | 109 | |
| A10.21 IgG4 (S228P) IFN (R33A, T106A) | 48 | 81 | 13 | 65 |
| A10.21 IgG4 (S228P) IFN (A145Q, T106T) | 48 | 81 | 107 | |
| A10.21 IgG4 (S228P) IFN (A145Q, T106A) | 48 | 81 | 25 | 66 |
| A10.21 IgG4 (S228P) IFN (A145N, T106T) | 48 | 81 | 107 | |
| A10.21 IgG4 (S228P) IFN (A145N, T106A) | 48 | 81 | 25 | 66 |
| A10.21 IgG4 (S228P) IFN (R144N, T106T) | 48 | 81 | 108 | |
| A10.21 IgG4 (S228P) IFN (R144N, T106A) | 48 | 81 | 24 | 67 |
| A10.21 IgG4 (S228P) IFN (R144H, T106T) | 48 | 81 | 108 | |
| A10.21 IgG4 (S228P) IFN (R144H, T106A) | 48 | 81 | 24 | 67 |
| A10.21 IgG1 IFN (A145D, T106T) | 50 | 81 | 107 | |
| A10.21 IgG1 IFN (A145D, T106A) | 50 | 81 | 25 | 68 |
| A10.21 IgG1 IFN (A145D, AT106) | 50 | 81 | 110 | 83 |

TABLE 8-continued

| Antibody Constructs | Seq Id No. Heavy Chain | Light Chain | IFN | VH + IFN |
|---|---|---|---|---|
| A10.21 IgG1 (L235A, G237A) IFN (A145D, T106T) | 51 | 81 | 107 | |
| A10.21 IgG1 (L235A, G237A) IFN (A145D, T106A) | 51 | 81 | 25 | 69 |
| A10.21 IgG1 (L235A, G237A, M252Y, S254T, T256E) IFN (A145D, T106T) | 52 | 81 | 107 | |
| A10.21 IgG1 (L235A, G237A, M252Y, S254T, T256E) IFN (A145D, T106A) | 52 | 81 | 25 | |
| A10.21 IgG1 (M252Y, S254T, T256E) IFN (A145D, T106T) | 52 | 81 | 107 | |
| A10.21 IgG1 (M252Y, S254T, T256E) IFN (A145D, T106A) | 111 | 81 | 25 | 70 |
| A10.21 IgG2 IFN (A145D, T106T) | 53 | 81 | 107 | |
| A10.21 IgG2 IFN (A145D, T106A) | 53 | 81 | 25 | 72 |
| A10.21 IgG2 (M252Y, S254T, T256E) IFN (A145D, T106T) | 54 | 81 | 107 | |
| A10.21 IgG2 (M252Y, S254T, T256E) IFN (A145D, T106A) | 54 | 81 | 25 | 73 |
| A10.43 IgG4 (S228P) IFN (A145D, T106T) | 55 | 81 | 107 | |
| A10.43 IgG4 (S228P) IFN (A145D, T106A) | 55 | 81 | 25 | 74 |
| R10A2 IgG4 (S228P) IFN (A145D, T106T) | 75 | 82 | 107 | |
| R10A2 IgG4 (S228P) IFN (A145D, T106A) | 75 | 82 | 25 | |
| R10A2 IgG4 (S228P) IFN (A145D, T106R) | 75 | 82 | 25 | |
| R10A2 IgG4 (S228P) IFN (A145D, T106N) | 75 | 82 | 25 | |
| R10A2 IgG4 (S228P) IFN (A145D, T106D) | 75 | 82 | 25 | |
| R10A2 IgG4 (S228P) IFN (A145D, T106C) | 75 | 82 | 25 | |
| R10A2 IgG4 (S228P) IFN (A145D, T106E) | 75 | 82 | 25 | |
| R10A2 IgG4 (S228P) IFN (A145D, T106Q) | 75 | 82 | 25 | |
| R10A2 IgG4 (S228P) IFN (A145D, T106G) | 75 | 82 | 25 | |
| R10A2 IgG4 (S228P) IFN (A145D, T106H) | 75 | 82 | 25 | |
| R10A2 IgG4 (S228P) IFN (A145D, T106I) | 75 | 82 | 25 | |
| R10A2 IgG4 (S228P) IFN (A145D, T106L) | 75 | 82 | 25 | |
| R10A2 IgG4 (S228P) IFN (A145D, T106K) | 75 | 82 | 25 | |
| R10A2 IgG4 (S228P) IFN (A145D, T106M) | 75 | 82 | 25 | |
| R10A2 IgG4 (S228P) IFN (A145D, T106F) | 75 | 82 | 25 | |
| R10A2 IgG4 (S228P) IFN (A145D, T106P) | 75 | 82 | 25 | |
| R10A2 IgG4 (S228P) IFN (A145D, T106S) | 75 | 82 | 25 | |
| R10A2 IgG4 (S228P) IFN (A145D, T106W) | 75 | 82 | 25 | |
| R10A2 IgG4 (S228P) IFN (A145D, T106Y) | 75 | 82 | 25 | |
| R10A2 IgG4 (S228P) IFN (A145D, T106V) | 75 | 82 | 25 | |
| A02.12 IgG4 (S228P) IFN (A145D, T106T) | 58 | 84 | 107 | |
| A02.12 IgG4 (S228P) IFN (A145D, T106A) | 58 | 84 | 25 | 77 |
| OPG-Fc (IgG2) IFN (A145D, T106T) | 57 | | 107 | |
| OPG-Fc (IgG2) IFN (A145D, T106A) | 57 | | 25 | 78 |
| Anti-CD138 IgG4 (S228P) IFN (A145D, T106T) | 59 | 85 | 107 | |

TABLE 8-continued

| Antibody Constructs | Seq Id No. Heavy Chain | Light Chain | IFN | VH + IFN |
|---|---|---|---|---|
| Anti-CD138 IgG4 (S228P) IFN (A145D,T106A) | 59 | 85 | 25 | |
| Anti-HLA IgG4 (S228P) IFN (A145D, T106T) | 60 | 86 | 107 | |
| Anti-HLA IgG4 (S228P) IFN (A145D, T106A) | 60 | 86 | 25 | |

INTRON® A was used as a positive control.

ON/OFF-Target Activity Measurement

The ON/OFF-target activity was measured using the same method described above as "iLite gene reporter assay"

iLite reporter gene assay (PBL Interferon Source, Piscataway, N.J., Cat #51100) was performed largely as described by the manufacturer, with the addition of a human IgG blocking step. The iLite cell line is described by the manufacturer as "a stable transfected cell line derived from a commercially available pro-monocytic human cell line characterized by the expression of MHC Class II antigens, in particular the human lymphocyte antigen (HLADR), on the cell surface." The cell line expresses CD38 and contains a stably transfected luciferase gene, the expression of which is driven by an interferon-response element (IRE), which allows for interferon activity to be quantified based on luminescence output.

The manufacturer supplied iLite plate (hereafter, assay plate) and diluent were removed from the −80° C. freezer and allowed to equilibrate to room temperature. 50 µL of the diluent was added per well to the assay plate. The vial of manufacturer-supplied reporter cells was removed from the −80° C. freezer and thawed in a 37° C. water bath. 25 µL aliquots of cells were dispensed into each well of the assay plate. Next, 12.5 µL of 8 mg/mL human IgG diluted in RPMI 1640+10% FBS (Sigma Chemicals, St. Louis, Mo.; cat #14506) was added per well. The contents were mixed and incubated at 37° C. for 15 minutes. On a separate "dilution plate," test articles were serially diluted in duplicate in RPMI 1640+10% FBS. Then, 12.5 µL of the test articles were transferred from the dilution plate to the assay plate. The assay plate was then incubated at 37° C. with 5% $CO_2$ for 17 hours. The manufacturer-supplied assay buffer and substrate were removed from the −80° C. freezer and allowed to equilibrate to room temperature for two hours. The manufacturer-supplied assay buffer was added to the manufacturer-supplied substrate vial and mixed well according to the manufacturer's instructions to create the "luminescence solution." Then, 100 µL of the luminescence solution was added to each well of the assay plate. The plate was shaken for 2 minutes. The plate was then incubated at room temperature for 5 minutes in the dark and read on a Victor 3V Multilabel Counter on a luminometry channel and the luminescence measured and presented as RLU.

To test the off-target activity of anti-CD38 antibody-IFN fusion protein constructs in the iLite assay, manufacturer-supplied diluent was supplemented with 0.25 mg/mL anti-CD38 antibody (an antibody recognizing the same epitope on CD38 as the antibody-IFN fusion protein construct being tested, to block any binding of the anti-CD38 antibody-IFN fusion protein constructs to the CD38 expressed on the iLite cells). This blocking stage was followed by treatment with anti-CD38 antibody-IFN fusion protein or IFNα2b.

Data was analyzed using Prism 5 (Graphpad, San Diego, Calif.) using non-linear regression and three parameter curve fit to determine the midpoint of the curve (EC50). Selectivity Index (SI) was calculated by EC50 (OFF-target activity)/EC50 (ON-target activity). Selectivity Index (SI) is a measure of how selectively active anti-CD38 IFN constructs are against CD38-expressing cells and non-active in cells with no CD38. The larger the number the more selective it is against the target, while a number close to 1 indicates that there is no selectivity against the target. Intron A was used as a positive control, has an SI of approximately 1.

The O-linked glycosylation site of anti-CD38 antibody attenuated interferon fusion constructs were removed by substituting threonine 106 (T106) to alanine (shown as T106A). The activity was investigated by comparing A10.21 and A10.43 anti-CD38 antibodies fused to IFNα2b with and without O-linked glycosylation.

Figure 3:
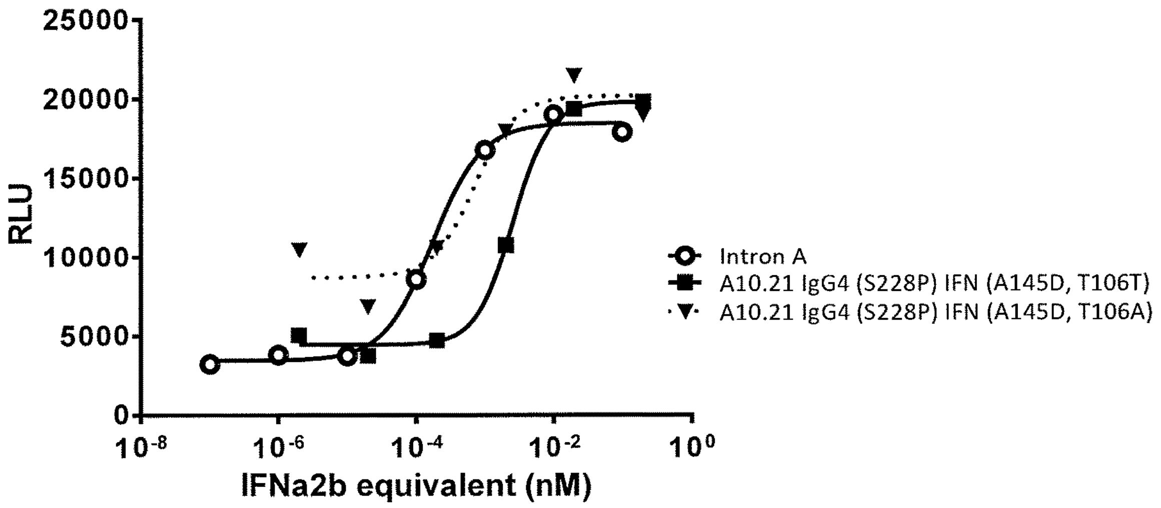
FIG. 3, parts A and B: On-target activities of (A) A10.21 and (B) A10.43 anti-CD38-attenuated IFNα2b fusion proteins with (T106T) and without (T106A) O-linked glycosylation of the IFNα2b.
Figure 3:
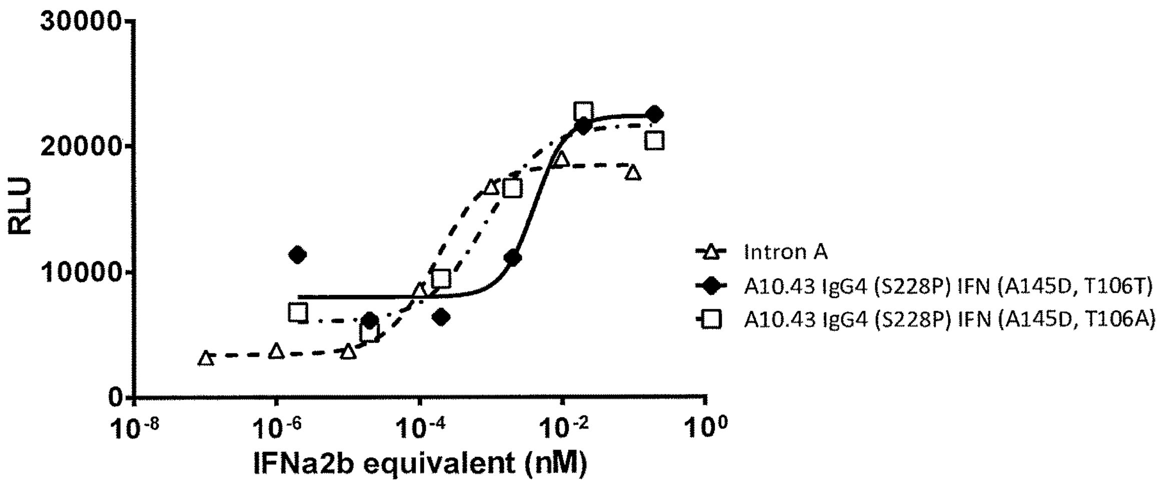
Figure 4:
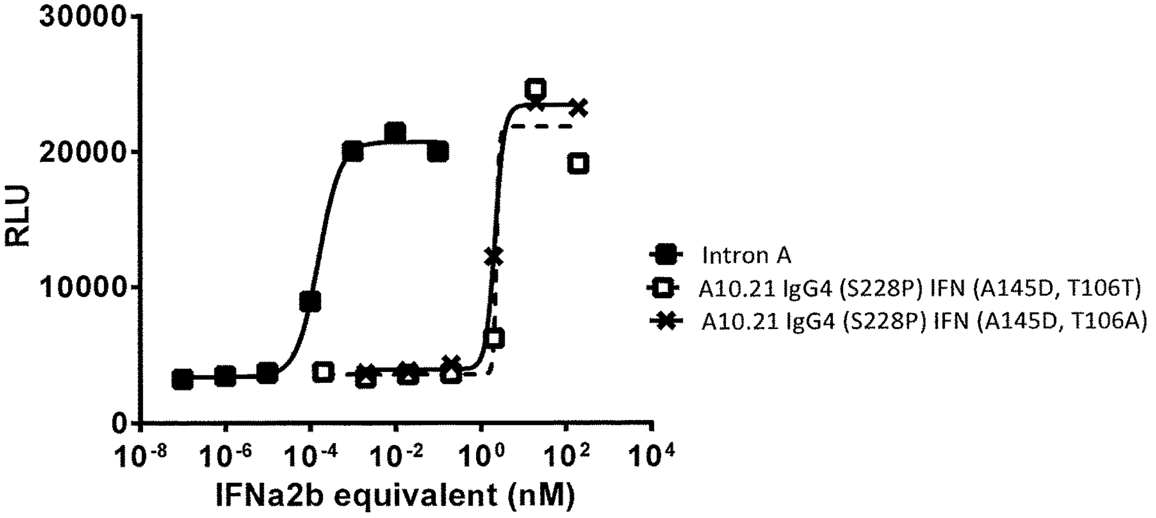
FIG. 4, parts A and B: Off-target activities of (A) A10.21 and (B) A10.43 anti-CD38-attenuated IFNα2b fusion proteins with (T106T) and without (T106A) O-linked glycosylation of the IFNα2b.
Figure 4:
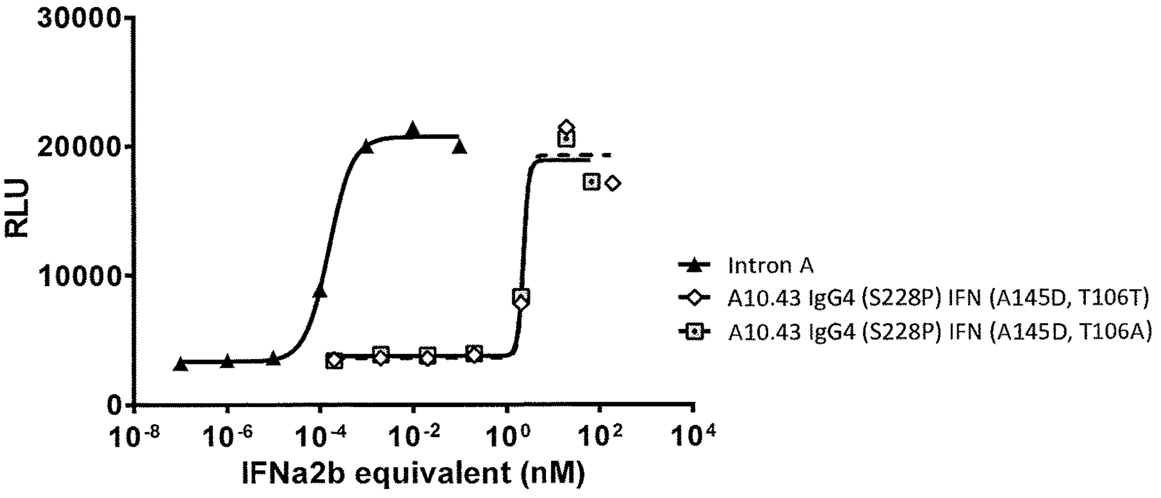

Removal of the O-linked glycosylation site in the attenuated IFN portion of the antibody fusion constructs (shown as T106A) resulted in slight increase in ON-target activity (FIG. 3 and Table 9) as well as slight to no increase in the OFF-target activity relative to O-linked glycosylated proteins. Both O-linked glycosylated and non-glycosylated proteins showed high selectivity towards CD38+ cells, while Intron A did not show selectivity.

TABLE 9

EC50 and SI of anti-CD38 antibody attenuated IFNα2b fusion proteins A10.21 and A10.43 with and without O-linked glycosylation

| Test Article | EC50 (nM) ON Target | EC50 (nM) OFF Target | SI |
|---|---|---|---|
| Intron A | 0.00017 | 0.00016 | 0.90 |
| A10.21 IgG4 (S228P) IFN(A145D, T106T) | 0.00240 | 2.33 | 972 |
| A10.21 IgG4 (S228P) IFN (A145D, T106A) | 0.00182 | 2.23 | 1223 |
| A10.43 IgG4 (S228P) IFN (A145D, T106T) | 0.00560 | 2.31 | 412 |
| A10.43 IgG4 (S228P) IFN (A145D, T106A) | 0.00124 | 2.25 | 1822 |

The impact on ON/OFF target activity of the removal of the O-linked glycosylation site from the attenuated IFN of fusion proteins may also be examined in a similar manner.

The iLite™ reporter gene ON-OFF target activity assays were conducted to demonstrate the selective activity of anti-CD38 attenuated IFN fusion proteins on target CD38+ cells and the limited activity on cells when CD38 is blocked with an anti-CD38 antibody (recognizing the same epitope) mimicking the activity anticipated on target negative cells.

Removal of the O-linked glycosylation site in the attenuated IFN portion of the antibody fusion constructs (by T106A substitution) resulted in a slight increase in ON-target activity as well as slight to no increase in the OFF-target activity relative to O-linked glycosylated proteins. Both O-linked glycosylated and non-glycosylated anti-CD38 antibody attenuated interferon fusion proteins showed high selectivity towards CD38+ cells, while Intron A did not show selectivity.

To further examine the modulation in selectivity index as a result of the removal of the O-linked glycosylation site in the attenuated IFN portion of the antibody fusion constructs, ON-OFF target activity was examined in a range of constructs. The changes examined were based on the A10.21 IgG4 (S228P) IFN (A145D, T106T) construct. These included deletion of threonine 106 (ΔT106), substitution of T106 to serine (T106S), YTE substitution (YTE T106T and YTE T106A), IFN attenuation by substitution from alanine 145 to glutamine (A145Q) and varying antibody isotype to IgG1 (IgG1 T106T and IgG1 T106A).

Figure 20:
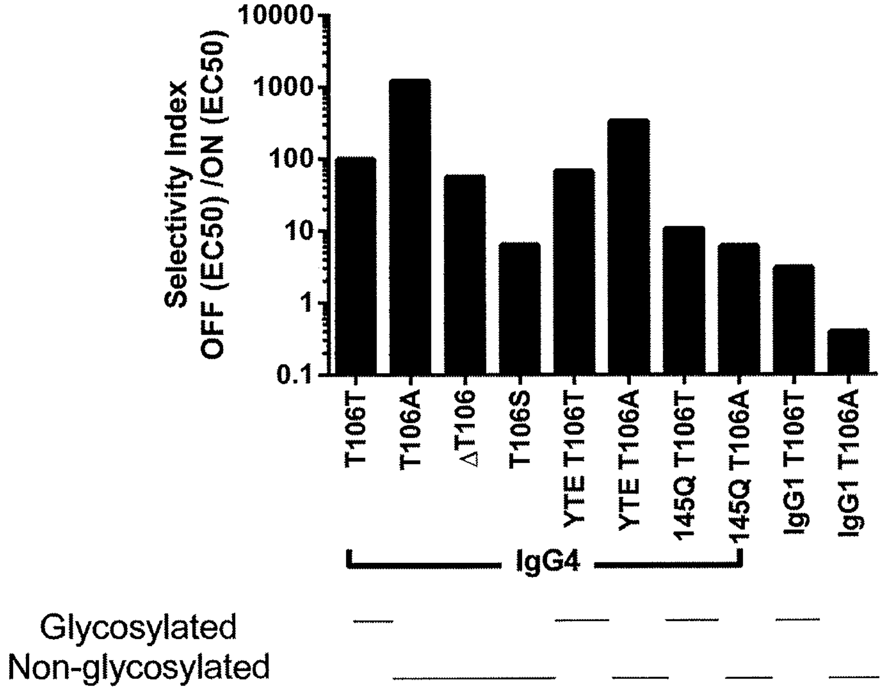
FIG. 20: Selectivity index of A10.21 anti-CD38-attenuated IFNα2b fusion proteins with and without O-linked glycosylation of the IFNα2b in the presence of a variety of amino acid substitutions to remove glycosylation of the IFN, YTE substitutions in the immunoglobulin constant region for extended half-life, IFN attenuation and Fc isotypes.

The majority of constructs demonstrated a selectivity index >1, the magnitude of selectivity towards targeted CD38+ cells varied depending on the anti-CD38 IFN fused construct (FIG. 20). The highest selectivity was observed in A10.21 IgG4 (S228P) IFN (A145D, T106A).

Example 4

Off-Target Activity of Anti-CD38 Antibody-Attenuated IFNα2b Fusion Proteins

HEK-Blue™ IFN-α/β cells allow the detection of bioactive human type I IFNs by monitoring the activation of the ISGF3 pathway. Stimulation of HEK-Blue™ IFN-α/β cells with human IFN-α activates the JAK/STAT/ISGF3 pathway and subsequently induces the production of SEAP (a reporter gene under the control of the IFN-α/β inducible ISG54 promoter). Levels of SEAP in the supernatant can be easily determined with QUANTI-Blue™. The effects of removal of O-linked glycosylation from the attenuated interferon portion of the antibody interferon fusion proteins were evaluated using this reporter gene assay.

Antibody/Fc fusion Protein Construct Production

Various transiently transfected cells expressing interferon fusion proteins were harvested and purified using a MABSELECT SURE® Protein A column. Samples were desalted into 200 mM Arginine, 25 mM Histidine pH 6.5 using a HiLoad Superdex 200 column.

TABLE 10

| Antibody Constructs | Seq Id No. Heavy Chain | Seq Id No. Light Chain | Seq Id No. IFN | Seq Id No. VH + IFN |
|---|---|---|---|---|
| A10.21 IgG4 (S228P) IFN (A145D, T106T) | 48 | 81 | 107 | |
| A10.21 IgG4 (S228P) IFN (A145D, T106A) | 48 | 81 | 25 | 87, 31 |
| A10.21 IgG4 (S228P) IFN (A145D, ΔT106) | 48 | 81 | 110 | 61 |
| A10.21 IgG4 (S228P) IFN (A145D, T106S) | 48 | 81 | 25 | 31 |
| A10.21 IgG4 (S228P) IFN (A145D, T106V) | 48 | 81 | 25 | 31 |
| A10.21 IgG4 (S228P) IFN (A145D, T106G) | 48 | 81 | 25 | 31 |
| A10.21 IgG4 (S228P) IFN (A145D, T106E) | 48 | 81 | 25 | 31 |
| A10.21 IgG4 (S228P, M252Y, S254T, T256E) IFN (A145D, T106T) | 49 | 81 | 107 | |
| A10.21 IgG4 (S228P, M252Y, S254T, T256E) IFN (A145D, T106A) | 49 | 81 | 25 | 62 |
| A10.21 IgG4 (S228P) IFN (R144I T106T) | 48 | 81 | 108 | |
| A10.21 IgG4 (S228P) IFN (R144I, T106A) | 48 | 81 | 24 | 63 |
| A10.21 IgG4 (S228P) IFN (A145K, T106T) | 48 | 81 | 107 | |
| A10.21 IgG4 (S228P) IFN (A145K, T106A) | 48 | 81 | 25 | 64 |
| A10.21 IgG4 (S228P) IFN (A145G, T106T) | 48 | 81 | 107 | |

TABLE 10-continued

| | Seq Id No. | | | |
|---|---|---|---|---|
| Antibody Constructs | Heavy Chain | Light Chain | IFN | VH + IFN |
| A10.21 IgG4 (S228P) IFN (A145G, T106A) | 48 | 81 | 25 | 64 |
| A10.21 IgG4 (S228P) IFN (R33A, T106T) | 48 | 81 | 109 | |
| A10.21 IgG4 (S228P) IFN (R33A, T106A) | 48 | 81 | 13 | 65 |
| A10.21 IgG4 (S228P) IFN (A145Q, T106T) | 48 | 81 | 107 | |
| A10.21 IgG4 (S228P) IFN (A145Q, T106A) | 48 | 81 | 25 | 66 |
| A10.21 IgG4 (S228P) IFN (A145N, T106T) | 48 | 81 | 107 | |
| A10.21 IgG4 (S228P) IFN (A145N, T106A) | 48 | 81 | 25 | 66 |
| A10.21 IgG4 (S228P) IFN (R144N, T106T) | 48 | 81 | 108 | |
| A10.21 IgG4 (S228P) IFN (R144N, T106A) | 48 | 81 | 24 | 67 |
| A10.21 IgG4 (S228P) IFN (R144H, T106T) | 48 | 81 | 108 | |
| A10.21 IgG4 (S228P) IFN (R144H, T106A) | 48 | 81 | 24 | 67 |
| A10.21 IgG1 IFN (A145D, T106T) | 50 | 81 | 107 | |
| A10.21 IgG1 IFN (A145D, T106A) | 50 | 81 | 25 | 68 |
| A10.21 IgG1 IFN (A145D, ΔT106) | 50 | 81 | 110 | 83 |
| A10.21 IgG1 (L235A, G237A) IFN (A145D, T106T) | 51 | 81 | 107 | |
| A10.21 IgG1 (L235A, G237A) IFN (A145D, T106A) | 51 | 81 | 25 | 69 |
| A10.21 IgG1 (L235A, G237A, M252Y, S254T, T256E) IFN (A145D, T106T) | 52 | 81 | 107 | |
| A10.21 IgG1 (L235A, G237A, M252Y, S254T, T256E) IFN (A145D, T106A) | 52 | 81 | 25 | |
| A10.21 IgG1 (M252Y, S254T, T256E) IFN (A145D, T106T) | 52 | 81 | 107 | |
| A10.21 IgG1 (M252Y, S254T, T256E) IFN (A145D, T106A) | 81 | 25 | 70 | |
| A10.21 IgG2 IFN (A145D, T106T) | 53 | 81 | 107 | |
| A10.21 IgG2 IFN (A145D, T106A) | 53 | 81 | 25 | 72 |
| A10.21 IgG2 (M252Y, S254T, T256E) IFN (A145D, T106T) | 54 | 81 | 107 | |
| A10.21 IgG2 (M252Y, S254T, T256E) IFN (A145D, T106A) | 54 | 81 | 25 | 73 |
| A10.43 IgG4 (S228P) IFN (A145D, T106T) | 55 | 81 | 107 | |
| A10.43 IgG4 (S228P) IFN (A145D, T106A) | 55 | 81 | 25 | 74 |
| R10A2 IgG4 (S228P) IFN (A145D, T106T) | 75 | 82 | 107 | |
| R10A2 IgG4 (S228P) IFN (A145D, T106A) | 75 | 82 | 25 | |
| R10A2 IgG4 (S228P) IFN (A145D, T106R) | 75 | 82 | 25 | |
| R10A2 IgG4 (S228P) IFN (A145D, T106N) | 75 | 82 | 25 | |
| R10A2 IgG4 (S228P) IFN (A145D, T106D) | 75 | 82 | 25 | |
| R10A2 IgG4 (S228P) IFN (A145D, T106C) | 75 | 82 | 25 | |
| R10A2 IgG4 (S228P) IFN (A145D, T106E) | 75 | 82 | 25 | |
| R10A2 IgG4 (S228P) IFN (A145D, T106Q) | 75 | 82 | 25 | |
| R10A2 IgG4 (S228P) IFN (A145D, T106G) | 75 | 82 | 25 | |
| R10A2 IgG4 (S228P) IFN (A145D, T106H) | 75 | 82 | 25 | |
| R10A2 IgG4 (S228P) IFN (A145D, T106I) | 75 | 82 | 25 | |
| R10A2 IgG4 (S228P) IFN (A145D, T106L) | 75 | 82 | 25 | |
| R10A2 IgG4 (S228P) IFN (A145D, T106K) | 75 | 82 | 25 | |
| R10A2 IgG4 (S228P) IFN (A145D, T106M) | 75 | 82 | 25 | |
| R10A2 IgG4 (S228P) IFN (A145D, T106F) | 75 | 82 | 25 | |
| R10A2 IgG4 (S228P) IFN (A145D, T106P) | 75 | 82 | 25 | |
| R10A2 IgG4 (S228P) IFN (A145D, T106S) | 75 | 82 | 25 | |
| R10A2 IgG4 (S228P) IFN (A145D, T106W) | 75 | 82 | 25 | |
| R10A2 IgG4 (S228P) IFN (A145D, T106Y) | 75 | 82 | 25 | |
| R10A2 IgG4 (S228P) IFN (A145D, T106V) | 75 | 82 | 25 | |
| A02.12 IgG4 (S228P) IFN (A145D, T106T) | 58 | 84 | 107 | |
| A02.12 IgG4 (S228P) IFN (A145D, T106A) | 58 | 84 | 25 | 77 |
| OPG-Fc (IgG2) IFN (A145D, T106T) | 57 | | 107 | |
| OPG-Fc (IgG2) IFN (A145D, T106A) | 57 | | 25 | 78 |
| Anti-CD138 IgG4 (S228P) IFN (A145D, T106T) | 59 | 85 | 107 | |
| Anti-CD138 IgG4 (S228P) IFN (A145D, T106A) | 59 | 85 | 25 | |
| Anti-HLA IgG4 (S228P) IFN (A145D, T106T) | 60 | 86 | 107 | |
| Anti-HLA IgG4 (S228P) IFN (A145D, T106A) | 60 | 86 | 25 | |

INTRON® A was used as a positive control.

Off-Target Activity Measurement by HEK-Blue Assay

Off-target activity of antibody-IFN fusion was measured using the same method as described in "HEK-Blue Off-target assay" except for the volumes of cells seeded, diluted antibodies and supernatant used. The details of the assay are as follows.

HEK-Blue Off-target assay was used to quantify the ability of antibody-IFN fusion constructs to bind interferon-alpha/β receptor (IFNAR) using the HEK-Blue™ IFN-alpha/β cell line (InvivoGen, San Diego, Calif.). The "off-target (HB-IFN) assay" was performed largely as described by the manufacturer of the HEK-Blue IFN-alpha/β cell line. HEK-Blue™ IFN-alpha/β Cells are specifically designed to monitor the activation of the JAK-STAT pathway, which is induced by type I IFNs. The cells were generated by introducing the human STAT2 and IRF9 genes into HEK293 cells to obtain a fully active type I IFN signaling pathway. The HEK-Blue™ IFN-alpha/β cells stably express a reporter gene, secreted embryonic alkaline phosphatase (SEAP), under the control of the ISG54 promoter. ISG54 is a well-known ISG activated through an ISRE-dependent mechanism by type I IFNs. Upon IFN-alpha or IFNβ stimulation, HEK-Blue™ IFN-alpha/β cells activate the JAK-STAT pathway and then the expression of the SEAP reporter gene. SEAP is secreted into the media and can be quantitated using the colorimetric reagent QUANTI-Blue™.

Briefly, HEK-Blue IFN-alpha/β cells (Invivogen, San Diego Calif. cat # hkb-ifnab) were thawed and cultured in DMEM media (Mediatech, Manassas Va., cat #10-013-CV)+10% FBS (Hyclone, Logan Utah, cat # SH30070.03)

that had been heat inactivated (HI FBS). When the cells reached 60-80% confluence, they were lifted with Cell Stripper (Mediatech, cat #25-056-Cl). Cells were washed twice in DMEM+HI FBS and counted. Cells were adjusted to $2.77\times10^5$ viable cells/mL in DMEM+HI FBS and was seeded at 180 μL per well into a flat bottom 96 well tissue culture plate (hereafter, the "experimental plate"). Then, 204 of IFN-alpha2b or fusion protein construct, diluted into DMEM+HI FBS, was added per well. The plate was incubated at 37° C. 5% $CO_2$ for 16-24 hours. QUANTI-Blue (Invivogen, cat# rep-qbl) was prepared according to the manufacturer's directions. QUANTI-Blue (180 μL) was seeded into each well of a flat bottom plate (hereafter, the "assay plate"). Then, 20 μL supernatant per well from the experimental plate was transferred to assay plate. Assay plate was then incubated at 37° C. for 1-3 hours. Assay plate absorbance at 620 nm was read on a model SpectraMaxPlus 384 Microplate Reader from Molecular Devices. The data was analyzed using Graph Pad Prism.

The impact the presence or the absence of O-linked glycosylation in IFNα2b has on the off-target activity of the attenuated IFN fused anti-CD38 antibodies was evaluated.

The O-linked glycosylation site of an anti-CD38 antibody with attenuated interferon fusion constructs was removed by either substituting threonine 106 (T106) to alanine (shown as T106A) or deleting T106 (shown as ΔT106). The effect on off-target activity was investigated by comparing X10.21 anti-CD38 antibody fused to attenuated IFNα2b with and without O-linked glycosylation.

Figure 5:
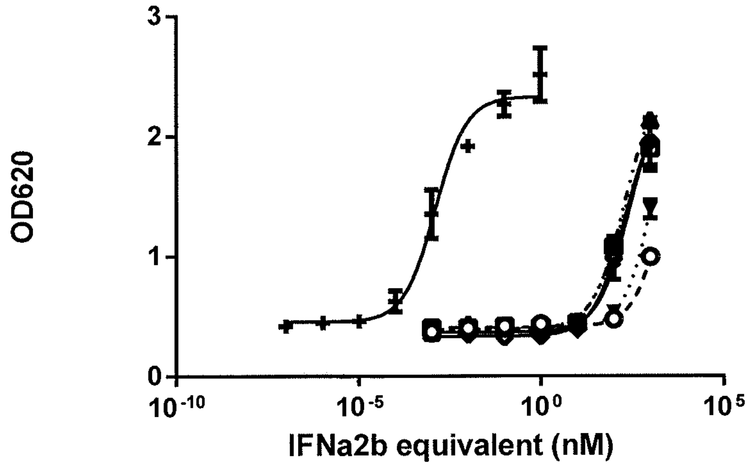
FIG. 5: Off-target activity by anti-CD38-attenuated IFNα2b fusion proteins with (T106T) and without (T106A or ΔT106) O-linked glycosylation of the IFNα2b.
Figure 6A:
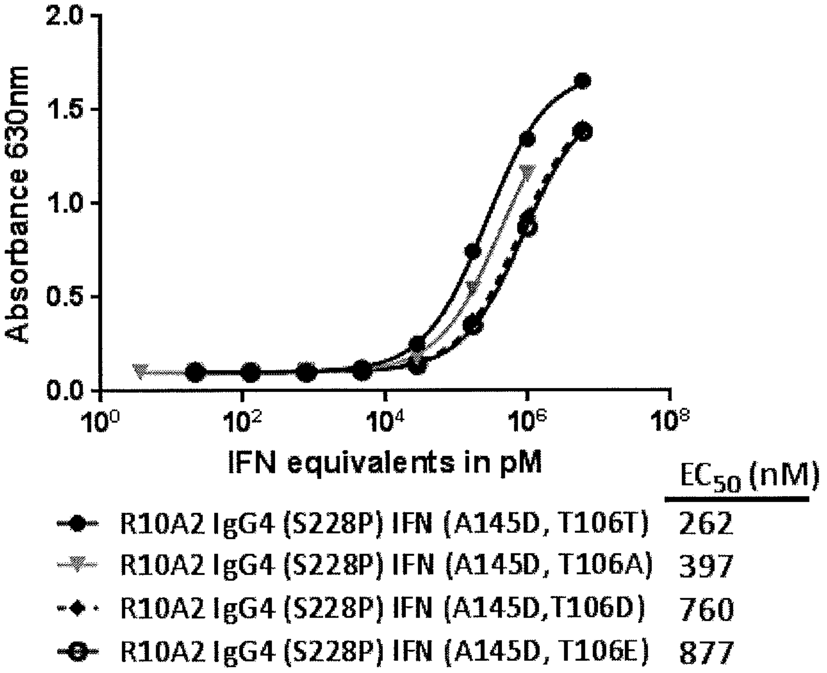
FIG. 6A, FIG. 6B, FIG. 6C, FIG. 6D, FIG. 6E and FIG. 6F: Off-target activity of anti-CD38-attenuated IFNα2b fusion proteins with different amino acid substitutions removing the O-linked glycosylation site from the attenuated IFNα2b.
Figure 6B:
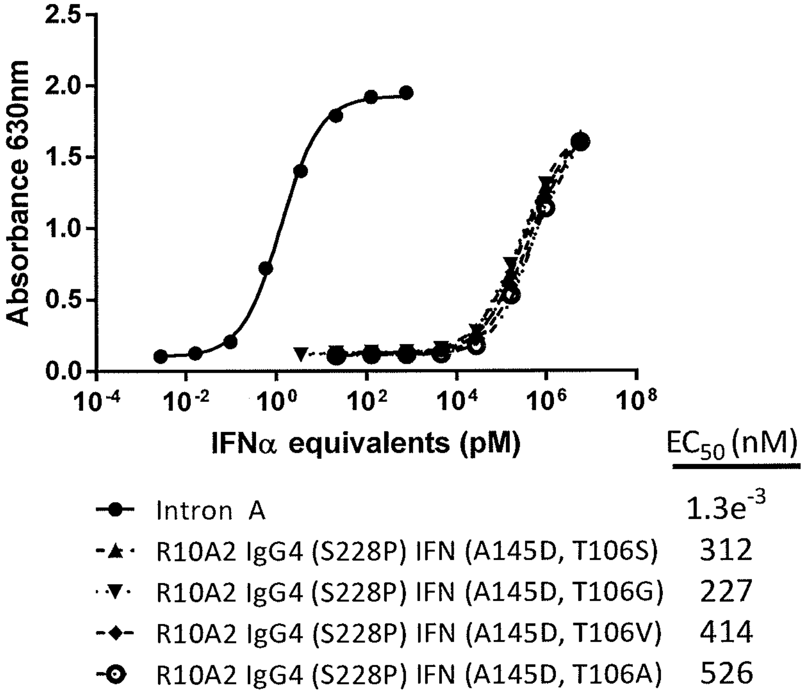
Figure 6C:
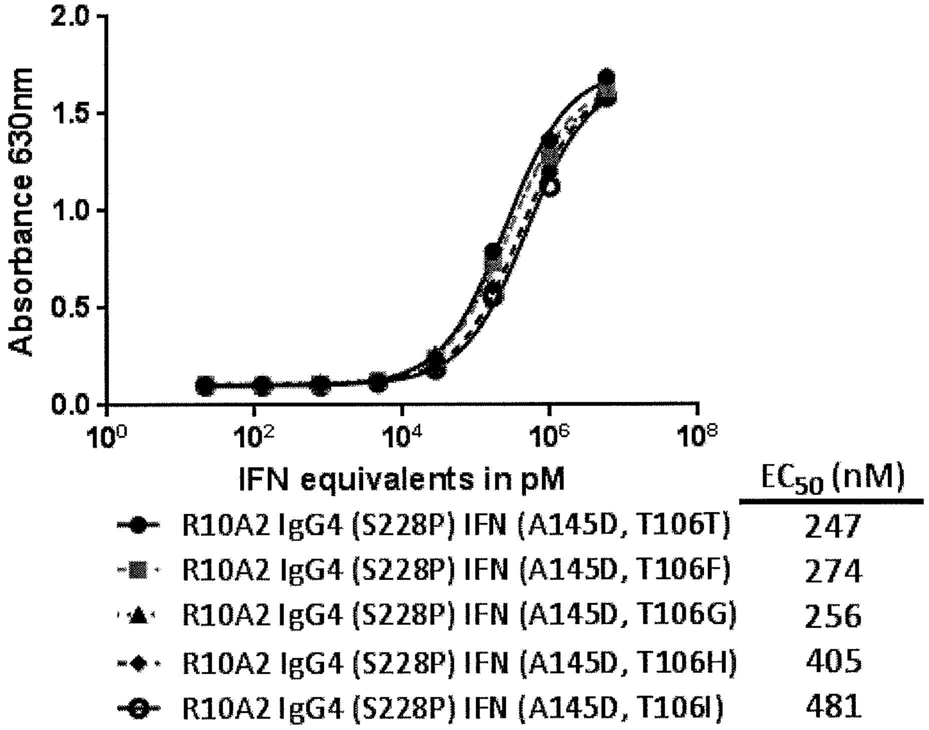
Figure 6D:
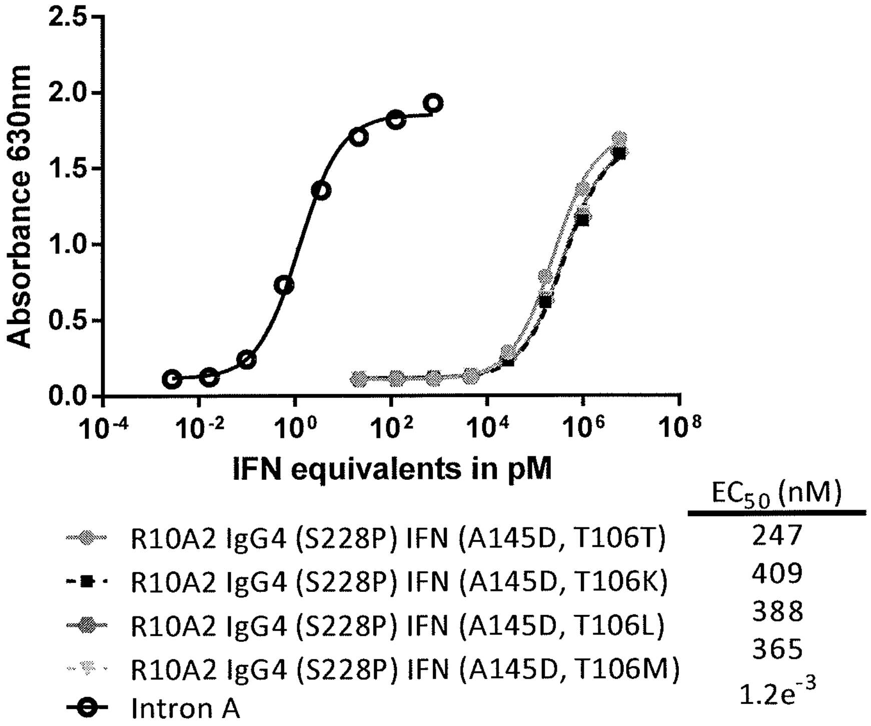
Figure 6E:
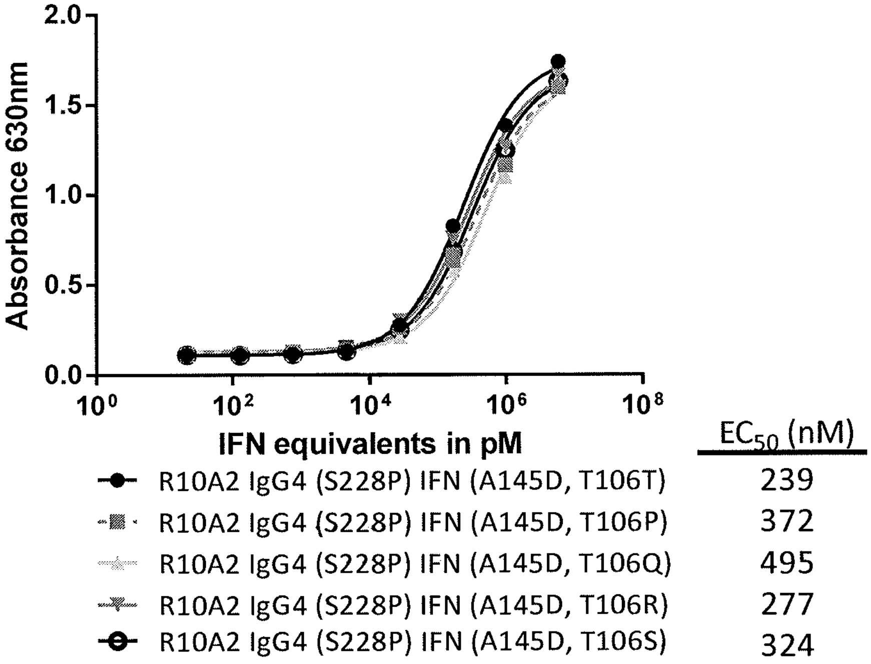
Figure 6F:
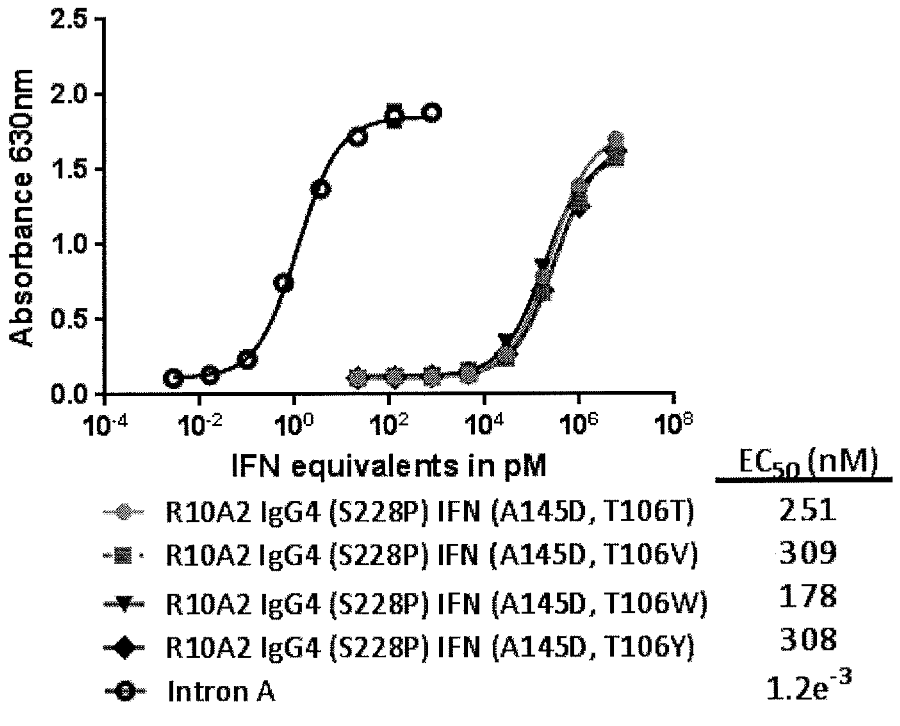
Figure 7:
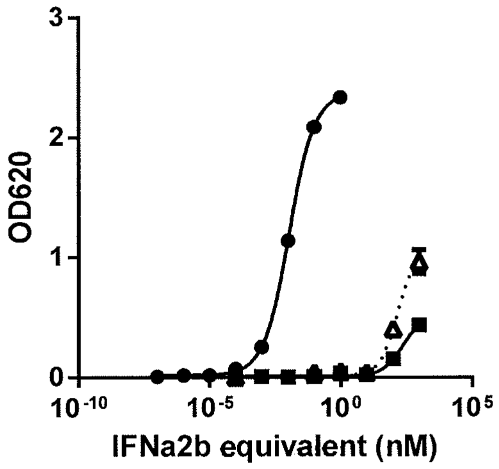
FIG. 7: Off-target activity of A10.43 anti-CD38-attenuated IFNα2b fusion proteins with (T106T) or without (T106A) O-linked glycosylation of the IFNα2b.

Removal of the O-linked glycosylation site in the attenuated IFN portion of the antibody fusion constructs resulted in a slight increase in off-target activity relative to O-linked glycosylated proteins i.e. A10.21 IgG4 IFN (145D, T106T) and A10.21 IgG1 IFN (145D, T106T) (FIG. 5). This trend was consistent regardless of isotype (FIG. 5). However IFNα2b (A145D) is so attenuated that the level of induction of SEAP in this assay is limited even at the highest doses used. Therefore the EC50 is an approximation only.

The off-target activity of antibodies fused with attenuated IFN (R10A2 IgG4 (S228P) IFN (A145D)) possessing different amino acid substitutions for the removal of O-linked glycosylation was examined. All possible amino acid substitutions were tested and the construct are listed in Table 11.

TABLE 11

| Construct Name | Seq Id No. Heavy Chain | Seq Id No. Light Chain | Seq Id No. IFN |
|---|---|---|---|
| R10A2 IgG4 (S228P) IFN (A145D, T106T) | 75 | 82 | 107 |
| R10A2 IgG4 (S228P) IFN (A145D, T106A) | 75 | 82 | 25 |
| R10A2 IgG4 (S228P) IFN (A145D, T106R) | 75 | 82 | 25 |
| R10A2 IgG4 (S228P) IFN (A145D, T106N) | 75 | 82 | 25 |
| R10A2 IgG4 (S228P) IFN (A145D, T106D) | 75 | 82 | 25 |
| R10A2 IgG4 (S228P) IFN (A145D, T106C) | 75 | 82 | 25 |
| R10A2 IgG4 (S228P) IFN (A145D, T106E) | 75 | 82 | 25 |
| R10A2 IgG4 (S228P) IFN (A145D, T106Q) | 75 | 82 | 25 |
| R10A2 IgG4 (S228P) IFN (A145D, T106G) | 75 | 82 | 25 |
| R10A2 IgG4 (S228P) IFN (A145D, T106H) | 75 | 82 | 25 |
| R10A2 IgG4 (S228P) IFN (A145D, T106I) | 75 | 82 | 25 |
| R10A2 IgG4 (S228P) IFN (A145D, T106L) | 75 | 82 | 25 |
| R10A2 IgG4 (S228P) IFN (A145D, T106K) | 75 | 82 | 25 |
| R10A2 IgG4 (S228P) IFN (A145D, T106M) | 75 | 82 | 25 |
| R10A2 IgG4 (S228P) IFN (A145D, T106F) | 75 | 82 | 25 |
| R10A2 IgG4 (S228P) IFN (A145D, T106P) | 75 | 82 | 25 |
| R10A2 IgG4 (S228P) IFN (A145D, T106S) | 75 | 82 | 25 |
| R10A2 IgG4 (S228P) IFN (A145D, T106W) | 75 | 82 | 25 |

TABLE 11-continued

| Construct Name | Seq Id No. Heavy Chain | Seq Id No. Light Chain | Seq Id No. IFN |
|---|---|---|---|
| R10A2 IgG4 (S228P) IFN (A145D, T106Y) | 75 | 82 | 25 |
| R10A2 IgG4 (S228P) IFN (A145D, T106V) | 75 | 82 | 25 |

It was shown that each of these substitutions demonstrated similar or slightly less off-target activity (increased $EC_{50}$) relative to the O-glycosylated IFN fused antibody R10A2 IgG4 (S228P) IFN (A145D, T106T). However, IFNα2b (A145D) is so attenuated that the level of induction of SEAP in this assay is limited even at the highest doses used. Therefore the $EC_{50}$ is an approximation only.

The off-target activity of another anti-CD38 antibody attenuated IFNα2b construct and the impact of removal of O-linked glycosylation by the T106A substitution was investigated. A10.43 has 7 amino acid changes in the heavy chain compared to A10.21 while the two constructs share the same light chain sequence (see Sequence Listing). The results demonstrated that removal of the O-linked glycosylation site by T106A substitution slightly increased the off-target activity of A10.43. However IFNα2b (A145D) is so attenuated that the level of induction of SEAP in this assay is limited even at the highest doses used. Therefore the $EC_{50}$ is an approximation only.

Removal of the O-linked glycosylation site in the attenuated IFN portion of the antibody interferon fusion constructs resulted in slight to no increase in the OFF-target activity as well as a slight increase in ON-target activity relative to O-linked glycosylated proteins. Both O-linked glycosylated and non-glycosylated anti-CD38 antibody attenuated interferon fusion proteins showed high selectivity towards CD38+ cells, while Intron A did not show selectivity.

Example 5

Evaluation of Human Neonatal Fc Receptor (FcRn) Binding to Anti-CD38-Attenuated IFN Poly-his-tagged FcRn was immobilized onto the designated active flow cells of a CMS sensor chip in a Biacore T200 enhanced instrument using an amine coupling protocol, while a blank immobilization was performed on the reference flow cells. Pulses of poly-his-tagged FcRn were injected over the active surfaces to ensure that the solution would pre-concentrate onto the flow cell. The surfaces were then washed with 50 mM NaOH. Both the reference and active surfaces were activated for seven minutes with a mix of 50:50 EDC/NHS. This was followed by a series of pulses of poly-his-tagged FcRn at 2 μg/mL in 10 mM Sodium Acetate pH 5.0 over the active surfaces only. Once the target of 150 RU was reached, both surfaces were deactivated with 1 M ethanolamine pH 8.5 for seven minutes. This protocol resulted in the immobilization of approximately 150 RU of poly-his-tagged FcRn onto the active surfaces. Each active surface was used for one run.

The test antibodies were desalted in PBS-P running buffer (DPBS, pH 7.4 and 0.005% Tween-20 adjusted to pH 6.0 with HCl at 25° C.) using Zeba Spin Desalting Column, 7K MWCO, 0.5 mL (Pierce Product #89882). Following desalting, the concentration of each sample was adjusted to 1 mg/mL.

On the day of the assay the 1 mg/mL solutions were further diluted in running buffer to prepare the highest concentration, and then diluted 1:2 to create the concentration series. The test samples were passed over the surface using a flow rate of 50 μL/minute. The association phase was 100 seconds while the dissociation phase was 300 seconds for all concentrations tested. The active and reference surfaces were regenerated using a 60 second injection of 100 mM Tris, 50 mM NaCl at pH 8.0 to remove the test antibody. Binding constants were determined at 25° C.

The antibody poly-his-FcRn binding interaction was evaluated using the two state reaction model where the $R_{max}$ was set to local and RI (refractive index) parameter was set to local. All data was double reference subtracted: first, the signal in the reference cell (blank immobilization) resulting from antibody binding to the dextran matrix was subtracted, and second, the signal of 0 nM antibody on the active surface was subtracted.

Binding constants were determined on at least two separate runs for each antibody. Prolia Lot 1035726 was tested alongside the anti-CD38/IFN samples as a positive control for each run. Average values for $k_{a1}$, $k_{d1}$, $k_{a2}$, $k_{d2}$ and $K_D$ were determined.

The average kinetic and affinity values for FcRn binding for the 4 anti-CD38/IFN (A10.21 IgG4 (S228P) IFN (A145D, T106A), A10.21 IgG4 (S228P) IFN (A145D, T106T) A10.43 IgG4 (S228P) IFN (A145D, T106A) A10.43 IgG4 (S228P) IFN (A145D, T106T)) were measured. In this sample set the clone A10.21 IgG4 (S228P) IFN (A145D, T106A) displayed the highest affinity for FcRn.

Example 6

Efficacy of Anti-CD38 Antibodies Fused to Attenuated Interferon Alpha 2B With and Without O-Linked Glycosylation in the Mouse NCI-H929 Multiple Myeloma Model Drugs and Treatment:

TABLE 12

| | | Regimen 1 | | | |
|---|---|---|---|---|---|
| Gr. | N | Agent | μg/animal | Route | Schedule |
| 1[#] | 8 | vehicle | 20 | ip | biwk × 5 |
| 2 | 8 | A10.21 IgG4 (S228P) IFN (A145D, T106T) | 20 | ip | biwk × 5 |
| 3 | 8 | A10.21 IgG4 (S228P) IFN (A145D, T106A) | 20 | ip | biwk × 5 |
| 4 | 8 | A10.43 IgG4 (S228P) IFN (A145D, T106T) | 20 | ip | biwk × 5 |
| 5 | 8 | A10.43 IgG4 (S228P) IFN (A145D, T106A) | 20 | ip | biwk × 5 |

[#]Control Group

Procedures:

- Set up CR female CB.17 SCID mice with $1\times10^7$ H929 tumor cells in 50% Matrigel sc in flank.
- Cell Injection Volume is 0.2 mL/mouse.
- Age at Start Date: 8 to 12 weeks.
- Perform a pair match when tumors reach an average size of 170-350 $mm^3$, and begin treatment.
- Dosing volume=0.2 mL/mouse. Do not adjust for body weight.
- Body Weight: qd×5 then biwk to end
- Caliper Measurement: biwk to end
- Endpoint TGD. Animals are to be monitored individually. The endpoint of the experiment is a tumor volume of 2000 $mm^3$ or 60 days, whichever comes first. Responders can be followed longer. When the endpoint is reached, the animals are to be euthanized per SOP #687.

Figure 8:
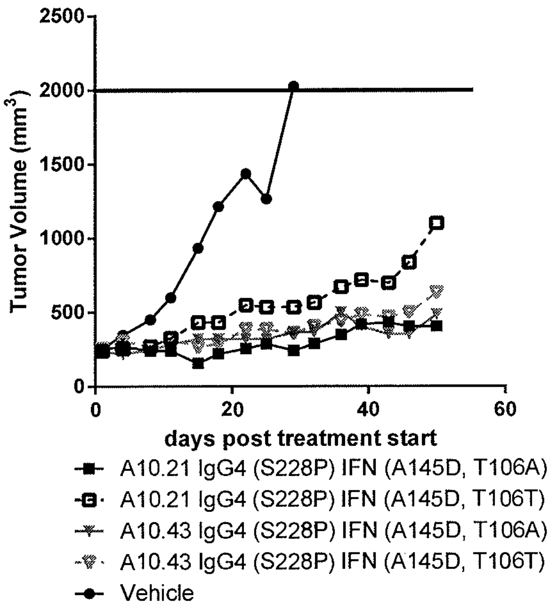
FIG. 8: Potency of sub-optimal dosages of anti-CD38-attenuated IFNα2b fusion proteins with (T106T) or without (T106A) O-linked glycosylation in treating tumours in a murine model of multiple myeloma.

The results are shown in FIG. 8. Roughly equivalent efficacy was seen with and without O-linked glycosylation, with the aglycosylated form slightly more potent in impeding tumour growth.

Example 7

In the evaluation of human neonatal Fc receptor (FcRn) binding to anti-CD38 antibodies fused to attenuated IFN with and without O-linked glycosylation the proteins without O-linked glycosylation displayed the highest affinity for FcRn. The effect of this may be evaluated in cynomolgus monkeys and humanised FcRn mice.

Cynomolgus Monkey Study

Monkey Study Design—to Compare +/−O-glyc

- Single 3 mg/kg intravenous infusion (1 hour) through an indwelling catheter
  - A10.21 IgG4 (S228P) IFN (145D, T106A) (n=4)
  - A10.21 IgG4 (S228P) IFN (145D, T106T) (n=4)
  - A10.21 IgG4 (S228P) IFN (145D, T106A) (n=4)
  - A10.21 IgG4 (S228P) IFN (145D, T106T) (n=4)
- Compare PK and PD (biological effect i.e. serum neopterin levels)
- PK: all monkeys, ≤1 ml, 11 timepoints (Pre.dose, 0 minutes (immediately post end of infusion). 2, 6, 12, 24, 48, 96, 120, 168 and at 240 hours post infusion. Samples (80) are analysed by ELISA.
- TK modelling: WinNonlin Table Assembly {non-compartmental analysis)
- Clinical pathology: Hematology and blood chemistry—all monkeys, 3 occasions (pre-treatment, 24 hours post dose and Day 8)
- Serum neopterin•all monkeys, ~0.5 ml 3 occasions at 5 timepoints (Predose, 12, 24, 96, 168 hours post dose)

Pharmacokinetic Study in Humanised FcRn Mice

1. Thirty two (32) B6.Cg-$Fcgr^{tm1Dcr}$Tg(CAG-FCGRT) 276Dcr/DcrJ (JAX stock #004919) female mice are dosed on day 1 by IP injection of 1 mg/kg of;
   - A10.21 IgG4 (S228P) IFN (145D, T106A) (n=8)
   - A10.21 IgG4 (S228P) IFN (145D, T106T) (n=8)
   - A10.43 IgG4 (S228P) IFN (145D, T106A) (n=8)
   - A10.43 IgG4 (S228P) IFN (145D, T106T) (n=8)
2. Body weight is measured 3 days prior to dosing, the day of dosing and then weekly.
3. Cage side observations are made daily and clinical observations made weekly.
4. Pharmacokinetic blood collection: Mice are bled (25 μl) at pre-dose 3 days and postdose 1, 12, 24, 48 and 72 hours and 5, 7, 10, and 14 days. Mice are bled in 2 cohorts (4 mice/group/cohort).
5. All mice are sacrificed on day 14. Terminal cardiocentesis is performed to collect blood.
6. Blood is collected in lithium heparin tubes and centrifuged at 10,000 rpm for 2 min at 4° C.
7. Plasma samples are diluted 1:10 in PBS and are frozen prior to analysis by binding ELISA for A10.21 IgG4 IFN (145D) A106, A10.21 IgG4 IFN(145D) T106, A10.43 IgG4 IFN(145D) A106 or A10.43 IgG4 IFN(145D) T106.

The invention claimed is:

1. A method of treating a tumour in a subject, the method comprising:

administering to the subject a fusion polypeptide comprising a first domain and a second domain, wherein the first domain comprises an antibody, or antigen-binding portion thereof, which binds to a cell surface-associated antigen on cells of the tumour and the second domain comprises an aglycosylated interferon α 2b (IFNα2b) comprising an amino acid sequence wherein T106 is deleted or substituted with an amino acid selected from the group consisting of A, C, D, E, F, G, H, I, K, L, M, N, P, Q, R, S, V, W, and Y, wherein T106 is relative to SEQ ID NO: 1 and wherein the aglycosylated IFNα2b further comprises one or more amino acid substitutions or deletions that attenuate the activity of the aglycosylated IFNα2b.

2. The method of claim 1, wherein the tumour is selected from multiple myeloma or non-Hodgkin's lymphoma.

3. The method of claim 1, wherein T106 is deleted or substituted with an amino acid selected from the group consisting of A, E, S, and V.

4. The method of claim 1, wherein the T106 is substituted with A.

5. The method of claim 1, comprising:

i) relative to SEQ ID NO: 1, the attenuating mutation A145D; or ii) relative to SEQ ID NO: 1 in which the residue at position 106 is deleted, the attenuating mutation A144D.

6. The method of claim 1, wherein the amino acid sequence of the aglycosylated IFNα2b is modified by the attenuating mutation(s) selected from the group consisting of L15A, R22A, R23A, S25A, L26A, F27A, L30A, L30V, K31A, D32A, R33A, R33K, R33Q, H34A, Q40A, D114R, L117A, R120A, R120E, R125A, R125E, K131A, E132A, K133A, K134A, M148A, R149A, S152A, L153A, N156A, (L30A, H57Y, E58N and Q61S), (R33A, H57Y, E58N, Q61S), (M148A, H57Y, E58N and Q61S), (L153A, H57Y, E58N and Q61S), (R144A, H57Y, E58N and Q61S), (N65A, L80A, Y85A and Y89A), (N65A, L80A, Y85A, Y89A and D114A), (N65A, L80A, Y85A, Y89A and L117A), (N65A, L80A, Y85A, Y89A and R120A), (Y85A, Y89A and D114A), (Y85A, Y89A, and R120A), (D114A and R120A), (L117A and R120A), (L117A, R120A and K121A), (R120A and K121A), (R120E and K121E), replacement of R at position 144 with A, D, E, G, H, I, K, L, N, Q, S, T, V or Y, replacement of A at position 145 with D, E, G, H, I, K, L, M, N, Q, R, S, T, V or Y, and deletion of residues L161 to E165.

7. The method of claim 1, wherein the amino acid sequence of the aglycosylated IFNα2b comprises a deletion of T106 and is further modified by the attenuating mutation(s) selected from the group consisting of L15A, R22A, R23A, S25A, L26A, F27A, L30A, L30V, K31A, D32A, R33A, R33K, R33Q, H34A, Q40A, D113R, L116A, R119A, R119E, R124A, R124E, K130A, E131A, K132A, K133A, M147A, R148A, S149A, L152A, N155A, (L30A, H57Y, E58N and Q61S), (R33A, H57Y, E58N, Q61S), (M147A, H57Y, E58N and Q61S), (L152A, H57Y, E58N and Q61S), (R143A, H57Y, E58N and Q61S), (N65A, L80A, Y85A and Y89A,) (N65A, L80A, Y85A, Y89A and D113A), (N65A, L80A, Y85A, Y89A and L116A), (N65A, L80A, Y85A, Y89A and R1190A), (Y85A, Y89A and D113A), (Y85A, Y89A, and R119A), (D113A and R119A), (L116A and R119A), (L116A, R119A and K120A), (R119A and K120A), (R119E and K120E), replacement of R at position 143 with A, D, E, G, H, I, K, L, N, Q, S, T, V or Y, replacement of A at position 144 with D, E, G, H, I, K, L, M, N, Q, R, S, T, V or Y, and deletion of residues L160 to E164.

8. The method of claim 1, wherein the amino acid sequence of the aglycosylated IFNα2b is selected from the group consisting of SEQ ID NOs: 3 to 30 and SEQ ID NOs: 32 to 47.

9. The method of claim 1, wherein the cell surface-associated antigen is selected from the group consisting of CD38, CD138, RANK-Ligand, HM1.24, CD56, CS1, CD20, CD74, IL-6R, Blys (BAFF), BCMA, HLA-SR, HLA-DR, Kininogen, beta2 microglobulin, Ep-CAM, FGFR3, ICAM-1, matriptase, CD52, EGFR, GM2, alpha4-integrin, IFG-1R, KIR, CD3, CD4, CD8, CD24, CD44, CD69, CD70, CD71, CD79, CD83, CD86, CD96, HLA, PD-1, ICOS, CD33, CD115, CD11c, CD19, CD52, CD14, FSP1, FAP, PDGFR alpha, PDGFR beta, ASGR1, ASGR2, FSP1, RTI140/Ti-alpha, HTI56, VEGF receptor, CD241 the product of the RCHE gene, CD117 (c-kit), CD71 (transferrin receptor), CD36 (thrombospondin receptor), CD34, CD45RO, CD45RA, CD115, CD168, CD235, CD236, CD237, CD238, CD239, and CD240.

10. The method of claim 1, wherein the antibody or antigen-binding portion thereof binds CD38.

11. The method of claim 10, wherein the heavy chain variable region (VH) amino acid sequence of the antibody is selected from the group consisting of SEQ ID NOs: 48 to 56 and 58.

12. The method of claim 11, wherein the light chain variable region (VL) amino acid sequence of the antibody is selected from the group consisting of SEQ ID NOs: 81, 82 and 84.

13. The method of claim 1, wherein the first domain is linked to the second domain via a peptide bond.

14. The method of claim 13, wherein the first domain is linked to the second domain directly via the peptide bond.

15. The method of claim 1, wherein the C-terminus of the first domain is linked to N-terminus of the second domain.

16. The method of claim 1, wherein the amino acid sequence of the aglycosylated IFNα2b is SEQ ID NO: 25.

17. The method of claim 1, wherein the fusion polypeptide comprises an amino acid sequence selected from the group consisting of SEQ ID NOs: 31, 61 to 77, 83 and 87, and an amino acid sequence selected from the group consisting of SEQ ID NOs: 81, 82 and 84.

18. The method of claim 1, wherein the fusion polypeptide comprises the amino acid sequence of SEQ ID NO: 87 and SEQ ID NO: 81.

* * * * *

SEQUENCE LISTING

<160> NUMBER OF SEQ ID NOS: 112

<210> SEQ ID NO 1
<211> LENGTH: 165
<212> TYPE: PRT
<213> ORGANISM: Artificial
<220> FEATURE:
<223> OTHER INFORMATION: Human interferon alpha-2-b with mutation at amino acid position 106
<220> FEATURE:
<221> NAME/KEY: VARIANT
<222> LOCATION: (106)..(106)
<223> OTHER INFORMATION: Xaa can be any amino acid selected from A, C, D, E, F, G, H, I, K, L, M, N, P, Q, R, V, W, Y

<400> SEQUENCE: 1

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Xaa Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 2
<211> LENGTH: 164
<212> TYPE: PRT
<213> ORGANISM: Artificial
<220> FEATURE:
<223> OTHER INFORMATION: Human Interferon alpha-2-b with deletion of amino acid at position 106

<400> SEQUENCE: 2

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95
```

```
Ala Cys Val Ile Gln Gly Val Gly Val Glu Thr Pro Leu Met Lys Glu
            100                 105                 110

Asp Ser Ile Leu Ala Val Arg Lys Tyr Phe Gln Arg Ile Thr Leu Tyr
        115                 120                 125

Leu Lys Glu Lys Lys Tyr Ser Pro Cys Ala Trp Glu Val Val Arg Ala
    130                 135                 140

Glu Ile Met Arg Ser Phe Ser Leu Ser Thr Asn Leu Gln Glu Ser Leu
145                 150                 155                 160

Arg Ser Lys Glu


<210> SEQ ID NO 3
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation L15A

<400> SEQUENCE: 3

Cys Asp Leu Pro Gln Thr His Ser Leu Gly Ser Arg Arg Thr Ala Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 4
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation A19W

<400> SEQUENCE: 4

Cys Asp Leu Pro Gln Thr His Ser Leu Gly Ser Arg Arg Thr Leu Met
1               5                   10                  15

Leu Leu Trp Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45
```

```
Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 5
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation R22A

<400> SEQUENCE: 5

Cys Asp Leu Pro Gln Thr His Ser Leu Gly Ser Arg Arg Thr Leu Met
1               5                   10                  15

Leu Leu Ala Gln Met Ala Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 6
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation R23A

<400> SEQUENCE: 6
```

```
Cys Asp Leu Pro Gln Thr His Ser Leu Gly Ser Arg Arg Thr Leu Met
1               5                   10                  15

Leu Leu Ala Gln Met Arg Ala Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 7
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation S25A

<400> SEQUENCE: 7

Cys Asp Leu Pro Gln Thr His Ser Leu Gly Ser Arg Arg Thr Leu Met
1               5                   10                  15

Leu Leu Ala Gln Met Arg Arg Ile Ala Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 8
```

```
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation L26A

<400> SEQUENCE: 8

Cys Asp Leu Pro Gln Thr His Ser Leu Gly Ser Arg Arg Thr Leu Met
1               5                   10                  15

Leu Leu Ala Gln Met Arg Arg Ile Ser Ala Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 9
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation F27A

<400> SEQUENCE: 9

Cys Asp Leu Pro Gln Thr His Ser Leu Gly Ser Arg Arg Thr Leu Met
1               5                   10                  15

Leu Leu Ala Gln Met Arg Arg Ile Ser Leu Ala Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140
```

Ala Glu Ile Met Arg Ser Phe Ser Leu Ser Thr Asn Leu Gln Glu Ser
145 150 155 160

Leu Arg Ser Lys Glu
165

<210> SEQ ID NO 10
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation L30X, where X can be any amino acid selected from A, V
<220> FEATURE:
<221> NAME/KEY: VARIANT
<222> LOCATION: (30)..(30)
<223> OTHER INFORMATION: Xaa can be any amino acid selected from A, V

<400> SEQUENCE: 10

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Xaa Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Ala Glu Thr Pro Leu Met Lys
100 105 110

Glu Asp Ser Ile Leu Ala Val Arg Lys Tyr Phe Gln Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 11
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation K31A

<400> SEQUENCE: 11

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Ala Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

```
Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 12
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation D32A

<400> SEQUENCE: 12

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Ala
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 13
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation R33X, where X can be any
      amino acid selected from K, A, Q
<220> FEATURE:
<221> NAME/KEY: VARIANT
<222> LOCATION: (33)..(33)
<223> OTHER INFORMATION: Xaa can be any amino acid selected from K, A, Q
```

<400> SEQUENCE: 13

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Xaa His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 14
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation H34A

<400> SEQUENCE: 14

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg Ala Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 15
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation Q40A

<400> SEQUENCE: 15

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Ala Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 16
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation D114R

<400> SEQUENCE: 16

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Arg Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 17
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation L117A

<400> SEQUENCE: 17

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Ala Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 18
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation R120X where X can be any
      amino acid selected from A, E
<220> FEATURE:
<221> NAME/KEY: VARIANT
<222> LOCATION: (120)..(120)
<223> OTHER INFORMATION: Xaa can be any amino acid selected from A, E

<400> SEQUENCE: 18

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe

```
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Xaa Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 19
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation R125X where X can be any
      amino acid selected from A, E
<220> FEATURE:
<221> NAME/KEY: VARIANT
<222> LOCATION: (125)..(125)
<223> OTHER INFORMATION: Xaa can be any amino acid selected from A, E

<400> SEQUENCE: 19

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Xaa Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 20
<211> LENGTH: 165
<212> TYPE: PRT
<213> ORGANISM: Artificial
<220> FEATURE:
<223> OTHER INFORMATION: Aglycosylated (T106A) human interferon
```

alpha-2-b comprising attenuating mutation K131A

<400> SEQUENCE: 20

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Ala Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 21
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation E132A

<400> SEQUENCE: 21

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Ala Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu

165

<210> SEQ ID NO 22
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation K133A

<400> SEQUENCE: 22

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Ala Glu Thr Pro Leu Met Lys
100 105 110

Glu Asp Ser Ile Leu Ala Val Arg Lys Tyr Phe Gln Arg Ile Thr Leu
115 120 125

Tyr Leu Lys Glu Ala Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 23
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation K134A

<400> SEQUENCE: 23

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Ala Glu Thr Pro Leu Met Lys
100 105 110

Glu Asp Ser Ile Leu Ala Val Arg Lys Tyr Phe Gln Arg Ile Thr Leu

```
        115                 120                 125

Tyr Leu Lys Glu Lys Ala Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 24
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation R144X where X can be any amino acid selected from A, D, E, G, H, I, K, L, N, Q, S, T, V, Y
<220> FEATURE:
<221> NAME/KEY: VARIANT
<222> LOCATION: (144)..(144)
<223> OTHER INFORMATION: Xaa can be any amino acid selected from A, D, E, G, H, I, K, L, N, Q, S, T, V, Y

<400> SEQUENCE: 24

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Xaa
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 25
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutation A145X where X can be any amino acid selected from D, E, G, H, I, K, L, M, N, Q, R, S, T, V, Y
<220> FEATURE:
<221> NAME/KEY: VARIANT
<222> LOCATION: (145)..(145)
<223> OTHER INFORMATION: Xaa can be any amino acid selected from D, E, G, H, I, K, L, M, N, Q, R, S, T, V, Y

<400> SEQUENCE: 25

-continued

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Xaa Glu Ile Met Arg Ser Phe Ser Leu Ser Thr Asn Leu Gln Glu Ser
145                 150                 155                 160

Leu Arg Ser Lys Glu
                165


<210> SEQ ID NO 26
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation M148A

<400> SEQUENCE: 26

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Ala Arg Ser Phe Ser Leu Ser Thr Asn Leu Gln Glu Ser
145                 150                 155                 160

Leu Arg Ser Lys Glu
                165


<210> SEQ ID NO 27
```

```
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation R149A

<400> SEQUENCE: 27

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Ala Ser Phe Ser Leu Ser Thr Asn Leu Gln Glu Ser
145                 150                 155                 160

Leu Arg Ser Lys Glu
                165


<210> SEQ ID NO 28
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation S152A

<400> SEQUENCE: 28

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140
```

```
Ala Glu Ile Met Arg Ser Phe Ala Leu Ser Thr Asn Leu Gln Glu Ser
145                 150                 155                 160

Leu Arg Ser Lys Glu
                165


<210> SEQ ID NO 29
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation L153A

<400> SEQUENCE: 29

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Ala Ser Thr Asn Leu Gln Glu Ser
145                 150                 155                 160

Leu Arg Ser Lys Glu
                165


<210> SEQ ID NO 30
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutation N156A

<400> SEQUENCE: 30

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95
```

```
Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Ala Leu Gln Glu Ser
145                 150                 155                 160

Leu Arg Ser Lys Glu
                165


<210> SEQ ID NO 31
<211> LENGTH: 612
<212> TYPE: PRT
<213> ORGANISM: Artificial
<220> FEATURE:
<223> OTHER INFORMATION: A10.21 IgG4 (S228P) IFN (A592D, T553X) where X
      can be any amino acid selected from A, G, E, S, V
<220> FEATURE:
<221> NAME/KEY: VARIANT
<222> LOCATION: (553)..(553)
<223> OTHER INFORMATION: Xaa can be any amino acid selected from A, G,
      E, S, V

<400> SEQUENCE: 31

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

-continued

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Xaa Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Asp
            580                 585                 590

Glu Ile Met Arg Ser Phe Ser Leu Ser Thr Asn Leu Gln Glu Ser Leu
        595                 600                 605

Arg Ser Lys Glu
    610
```

<210> SEQ ID NO 32
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutations L30A, H57Y, E58N and Q61S

<400> SEQUENCE: 32

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Ala Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 33
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutations R33A, H57Y, E58N and Q61S

<400> SEQUENCE: 33

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Ala His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu

```
                165


<210> SEQ ID NO 34
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations M148A, H57Y, E58N and
      Q61S

<400> SEQUENCE: 34

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Ala Arg Ser Phe Ser Leu Ser Thr Asn Leu Gln Glu Ser
145                 150                 155                 160

Leu Arg Ser Lys Glu
                165


<210> SEQ ID NO 35
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations L153A, H57Y, E58N and
      Q61S

<400> SEQUENCE: 35

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110
```

```
Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Ala Ser Thr Asn Leu Gln Glu Ser
145                 150                 155                 160

Leu Arg Ser Lys Glu
                165


<210> SEQ ID NO 36
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations R144A, H57Y, E58N and
      Q61S

<400> SEQUENCE: 36

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Ala
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 37
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations N65A,L80A, Y85A, Y89A

<400> SEQUENCE: 37

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
```

-continued

```
    50                  55                  60

Ala Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 38
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations N65A,L80A, Y85A, Y89A
      and D114A

<400> SEQUENCE: 38

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Ala Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Ala Glu Thr Pro Leu Met Lys
            100                 105                 110

Glu Ala Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 39
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations N65A,L80A, Y85A, Y89A
      and L117A

<400> SEQUENCE: 39
```

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Ala Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Ala Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 40
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations N65A,L80A, Y85A, Y89A
      and R120A

<400> SEQUENCE: 40

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Ala Leu Phe Ser Thr Lys Asp Ser Ser Ala Ala Trp Asp Glu Thr Ala
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Ala Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 41
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutations Y85A, Y89A and R120A

<400> SEQUENCE: 41

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Ala Thr Glu Leu Ala Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Ala Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 42
<211> LENGTH: 165
<212> TYPE: PRT
<213> ORGANISM: Artificial
<220> FEATURE:
<223> OTHER INFORMATION: Aglycosylated (T106A) human interferon alpha-2-b comprising attenuating mutations D114A,R120A

<400> SEQUENCE: 42

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Ala Ser Ile Leu Ala Val Ala Lys Tyr Phe Gln Arg Ile Thr Leu
        115                 120                 125
```

```
Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 43
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations L117A,R120A

<400> SEQUENCE: 43

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Ala Ala Val Ala Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 44
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations L117A,R120A,K121A

<400> SEQUENCE: 44

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80
```

-continued

```
Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Ala Ala Val Ala Ala Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 45
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations R120A,K121A

<400> SEQUENCE: 45

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Ala Glu Thr Pro Leu Met Lys
            100                 105                 110

Glu Asp Ser Ile Leu Ala Val Ala Ala Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 46
<211> LENGTH: 165
<212> TYPE: PRT
<213> ORGANISM: Artificial
<220> FEATURE:
<223> OTHER INFORMATION: Aglycosylated (T106A) human interferon
      alpha-2-b comprising attenuating mutations R120E,K121E

<400> SEQUENCE: 46

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30
```

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Ala Glu Thr Pro Leu Met Lys
100 105 110

Glu Asp Ser Ile Leu Ala Val Glu Glu Tyr Phe Gln Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 47
<211> LENGTH: 160
<212> TYPE: PRT
<213> ORGANISM: Artificial
<220> FEATURE:
<223> OTHER INFORMATION: Aglycosylated (T106A) human interferon alpha-2-b comprising attenuating deletion of residues L161-E165

<400> SEQUENCE: 47

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Ala Glu Thr Pro Leu Met Lys
100 105 110

Glu Asp Ser Ile Leu Ala Val Arg Lys Tyr Phe Gln Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

<210> SEQ ID NO 48
<211> LENGTH: 447
<212> TYPE: PRT
<213> ORGANISM: Artificial
<220> FEATURE:
<223> OTHER INFORMATION: VH sequence of 10.21 formatted as IgG4 incorporating hinge stabilisation substitution S228P

<400> SEQUENCE: 48

-continued

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
```

```
            420                 425                 430

His Asn His Tyr Thr Gln Lys Ser Leu Ser Leu Ser Leu Gly Lys
        435                 440                 445


<210> SEQ ID NO 49
<211> LENGTH: 447
<212> TYPE: PRT
<213> ORGANISM: Artificial
<220> FEATURE:
<223> OTHER INFORMATION: VH sequence of 10.21 formatted as an IgG4
      incorporating hinge stabilisation substitution S228P and YTE
      residues substituted in positions 252, 254, 256 respectively

<400> SEQUENCE: 49

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Tyr Ile Thr Arg Glu
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 50
<211> LENGTH: 450
<212> TYPE: PRT
<213> ORGANISM: Artificial
<220> FEATURE:
<223> OTHER INFORMATION: VH sequence of 10.21 formatted as an IgG1

<400> SEQUENCE: 50

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 51
<211> LENGTH: 450
<212> TYPE: PRT
<213> ORGANISM: Artificial
<220> FEATURE:
<223> OTHER INFORMATION: VH sequence of 10.21 formatted as an IgG1
      incorporating substitutions L238A and G240A to reduce effector
      function

<400> SEQUENCE: 51

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 52
<211> LENGTH: 450
<212> TYPE: PRT
<213> ORGANISM: Artificial
<220> FEATURE:
<223> OTHER INFORMATION: VH sequence of 10.21 formatted as an IgG1
      incorporating substitutions L235A and G237A (reduce effector
      function) and M255Y, S257T, T259E

<400> SEQUENCE: 52

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
```

-continued

```
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 53
<211> LENGTH: 446
<212> TYPE: PRT
<213> ORGANISM: Artificial
<220> FEATURE:
<223> OTHER INFORMATION: VH sequence of 10.21 formatted onto an IgG2 backbone

<400> SEQUENCE: 53

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
```

```
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 54
<211> LENGTH: 446
<212> TYPE: PRT
<213> ORGANISM: Artificial
<220> FEATURE:
<223> OTHER INFORMATION: VH sequence of 10.21 formatted onto an IgG2
      backbone incorporating substitutions M251Y, S253T and T255E

<400> SEQUENCE: 54

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser His Glu Asp Pro Glu Val
            260                 265                 270
```

```
Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 55
<211> LENGTH: 447
<212> TYPE: PRT
<213> ORGANISM: Artificial
<220> FEATURE:
<223> OTHER INFORMATION: VH sequence of 10.43 formatted onto an IgG4
      backbone incorporating the hinge stabilisation substitution S228P

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 56
<211> LENGTH: 447
<212> TYPE: PRT
<213> ORGANISM: Artificial
<220> FEATURE:
<223> OTHER INFORMATION: VH sequence of 10.152 formatted as an IgG4 incorporating the hinge stabilisation substitution S228P

<400> SEQUENCE: 56

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Ser
20 25 30

Val Met Asn Trp Val Gln Gln His Pro Gly Lys Gly Leu Glu Trp Met
35 40 45

Gly Trp Ile Asp Pro Glu Tyr Gly Arg Thr Asp Val Ala Glu Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Thr Lys Tyr Asn Ser Gly Tyr Gly Phe Pro Tyr Trp Gly Gln

```
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 57
<211> LENGTH: 401
<212> TYPE: PRT
<213> ORGANISM: Artificial
<220> FEATURE:
<223> OTHER INFORMATION: OPG-Fc construct

<400> SEQUENCE: 57

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
```

```
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Gly Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Glu Arg Lys
                165                 170                 175

Cys Cys Val Glu Cys Pro Pro Cys Pro Ala Pro Pro Val Ala Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Gln Phe Asn Trp Tyr Val Asp Gly Val Glu Val His Asn
225                 230                 235                 240

Ala Lys Thr Lys Pro Arg Glu Glu Gln Phe Asn Ser Thr Phe Arg Val
                245                 250                 255

Val Ser Val Leu Thr Val Val His Gln Asp Trp Leu Asn Gly Lys Glu
            260                 265                 270

Tyr Lys Cys Lys Val Ser Asn Lys Gly Leu Pro Ala Pro Ile Glu Lys
        275                 280                 285

Thr Ile Ser Lys Thr Lys Gly Gln Pro Arg Glu Pro Gln Val Tyr Thr
    290                 295                 300

Leu Pro Pro Ser Arg Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Met Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys


<210> SEQ ID NO 58
<211> LENGTH: 448
<212> TYPE: PRT
<213> ORGANISM: Artificial
<220> FEATURE:
```

-continued

<223> OTHER INFORMATION: X2.12 VH sequence formatted as an IgG4 (S228P)

<400> SEQUENCE: 58

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly Gly Ala Gly Gly Trp Pro Leu Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
405 410 415

Arg Trp Gln Glu Gly Asn Val Phe Ser Cys Ser Val Met His Glu Ala
420 425 430

Leu His Asn His Tyr Thr Gln Lys Ser Leu Ser Leu Ser Leu Gly Lys
435 440 445

<210> SEQ ID NO 59
<211> LENGTH: 449
<212> TYPE: PRT
<213> ORGANISM: Artificial
<220> FEATURE:
<223> OTHER INFORMATION: Anti-CD138 VH sequence formatted onto an IgG4 (S228P) backbone

<400> SEQUENCE: 59

Gln Val Gln Leu Gln Gln Ser Gly Ser Glu Leu Met Met Pro Gly Ala
1 5 10 15

Ser Val Lys Ile Ser Cys Lys Ala Thr Gly Tyr Thr Phe Ser Asn Tyr
20 25 30

Trp Ile Glu Trp Val Lys Gln Arg Pro Gly His Gly Leu Glu Trp Ile
35 40 45

Gly Glu Ile Leu Pro Gly Thr Gly Arg Thr Ile Tyr Asn Glu Lys Phe
50 55 60

Lys Gly Lys Ala Thr Phe Thr Ala Asp Ile Ser Ser Asn Thr Val Gln
65 70 75 80

Met Gln Leu Ser Ser Leu Thr Ser Glu Asp Ser Ala Val Tyr Tyr Cys
85 90 95

Ala Arg Arg Asp Tyr Tyr Gly Asn Phe Tyr Tyr Ala Met Asp Tyr Trp
100 105 110

Gly Gln Gly Thr Ser Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Lys Thr Tyr Thr Cys Asn Val Asp
195 200 205

His Lys Pro Ser Asn Thr Lys Val Asp Lys Arg Val Glu Ser Lys Tyr
210 215 220

Gly Pro Pro Cys Pro Pro Cys Pro Ala Pro Glu Phe Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Gln Glu Asp
260 265 270

Pro Glu Val Gln Phe Asn Trp Tyr Val Asp Gly Val Glu Val His Asn
275 280 285

Ala Lys Thr Lys Pro Arg Glu Glu Gln Phe Asn Ser Thr Tyr Arg Val
290 295 300

Val Ser Val Leu Thr Val Leu His Gln Asp Trp Leu Asn Gly Lys Glu
305 310 315 320

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 60
<211> LENGTH: 447
<212> TYPE: PRT
<213> ORGANISM: Artificial
<220> FEATURE:
<223> OTHER INFORMATION: Anti-HLA VH sequence formatted onto IgG4
      incorporating the hinge stabilising substitution S228P

<400> SEQUENCE: 60

Gln Val Gln Leu Lys Gln Ser Gly Pro Gly Leu Val Gln Pro Ser Gln
1               5                   10                  15

Ser Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Arg Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 61
<211> LENGTH: 611
<212> TYPE: PRT
<213> ORGANISM: Artificial
<220> FEATURE:
<223> OTHER INFORMATION: A10.21VH sequence formatted onto IgG4 backbone incorporating hinge stabilisation subsitution S228P and the deletion of Threonine residue at position 553 (ie:T106 in interferon sequence)

<400> SEQUENCE: 61

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Ser
20 25 30

Val Met Asn Trp Val Gln Gln Ala Pro Gly Lys Gly Leu Glu Trp Met
35 40 45

Gly Trp Ile Asp Pro Glu Tyr Gly Arg Thr Asp Val Ala Glu Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Thr Lys Tyr Asn Ser Gly Tyr Gly Phe Pro Tyr Trp Gly Gln
100 105 110

Gly Thr Thr Val Thr Val Ser Ser Ala Ser Thr Lys Gly Pro Ser Val
115 120 125

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540
```

```
Cys Val Ile Gln Gly Val Gly Val Glu Thr Pro Leu Met Lys Glu Asp
545                 550                 555                 560

Ser Ile Leu Ala Val Arg Lys Tyr Phe Gln Arg Ile Thr Leu Tyr Leu
                565                 570                 575

Lys Glu Lys Lys Tyr Ser Pro Cys Ala Trp Glu Val Val Arg Asp Glu
            580                 585                 590

Ile Met Arg Ser Phe Ser Leu Ser Thr Asn Leu Gln Glu Ser Leu Arg
        595                 600                 605

Ser Lys Glu
    610


<210> SEQ ID NO 62
<211> LENGTH: 612
<212> TYPE: PRT
<213> ORGANISM: Artificial
<220> FEATURE:
<223> OTHER INFORMATION: A10.21 IgG4 IFN

<400> SEQUENCE: 62

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Tyr Ile Thr Arg Glu
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Asp
            580                 585                 590

Glu Ile Met Arg Ser Phe Ser Leu Ser Thr Asn Leu Gln Glu Ser Leu
        595                 600                 605

Arg Ser Lys Glu
    610
```

<210> SEQ ID NO 63
<211> LENGTH: 612
<212> TYPE: PRT
<213> ORGANISM: Artificial
<220> FEATURE:
<223> OTHER INFORMATION: A10.21 IgG4 IFN

<400> SEQUENCE: 63

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30
```

```
Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
```

```
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Ile Ala
            580                 585                 590

Glu Ile Met Arg Ser Phe Ser Leu Ser Thr Asn Leu Gln Glu Ser Leu
        595                 600                 605

Arg Ser Lys Glu
    610


<210> SEQ ID NO 64
<211> LENGTH: 612
<212> TYPE: PRT
<213> ORGANISM: Artificial
<220> FEATURE:
<223> OTHER INFORMATION: A10.21 IgG4 IFN
<220> FEATURE:
<221> NAME/KEY: VARIANT
<222> LOCATION: (592)..(592)
<223> OTHER INFORMATION: Where Xaa can be any amino acid selected from
      G, K

<400> SEQUENCE: 64

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Xaa
            580                 585                 590
```

Glu Ile Met Arg Ser Phe Ser Leu Ser Thr Asn Leu Gln Glu Ser Leu
595 600 605

Arg Ser Lys Glu
610

<210> SEQ ID NO 65
<211> LENGTH: 612
<212> TYPE: PRT
<213> ORGANISM: Artificial
<220> FEATURE:
<223> OTHER INFORMATION: A10.21 IgG4 IFN

<400> SEQUENCE: 65

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Ser
20 25 30

Val Met Asn Trp Val Gln Gln Ala Pro Gly Lys Gly Leu Glu Trp Met
35 40 45

Gly Trp Ile Asp Pro Glu Tyr Gly Arg Thr Asp Val Ala Glu Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Thr Lys Tyr Asn Ser Gly Tyr Gly Phe Pro Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

```
Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Ala
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Ala
            580                 585                 590

Glu Ile Met Arg Ser Phe Ser Leu Ser Thr Asn Leu Gln Glu Ser Leu
        595                 600                 605

Arg Ser Lys Glu
    610


<210> SEQ ID NO 66
<211> LENGTH: 612
<212> TYPE: PRT
<213> ORGANISM: Artificial
<220> FEATURE:
<223> OTHER INFORMATION: A10.21 IgG4 IFN
<220> FEATURE:
<221> NAME/KEY: VARIANT
<222> LOCATION: (592)..(592)
<223> OTHER INFORMATION: Where Xaa can be any amino acid selected from
      the group Q, N

<400> SEQUENCE: 66

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
```

-continued

```
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480
```

```
His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Xaa
            580                 585                 590

Glu Ile Met Arg Ser Phe Ser Leu Ser Thr Asn Leu Gln Glu Ser Leu
        595                 600                 605

Arg Ser Lys Glu
    610
```

<210> SEQ ID NO 67
<211> LENGTH: 612
<212> TYPE: PRT
<213> ORGANISM: Artificial
<220> FEATURE:
<223> OTHER INFORMATION: A10.21 IgG4 IFN
<220> FEATURE:
<221> NAME/KEY: VARIANT
<222> LOCATION: (591)..(591)
<223> OTHER INFORMATION: Where Xaa can be any amino acid selected from H, N

<400> SEQUENCE: 67

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Xaa Ala
            580                 585                 590

Glu Ile Met Arg Ser Phe Ser Leu Ser Thr Asn Leu Gln Glu Ser Leu
        595                 600                 605

Arg Ser Lys Glu
```

610

<210> SEQ ID NO 68
<211> LENGTH: 615
<212> TYPE: PRT
<213> ORGANISM: Artificial
<220> FEATURE:
<223> OTHER INFORMATION: A10.21 IgG1 IFN

<400> SEQUENCE: 68

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Cys Asp Leu Pro Gln Thr His Ser Leu Gly Ser Arg Arg Thr
    450                 455                 460

Leu Met Leu Leu Ala Gln Met Arg Arg Ile Ser Leu Phe Ser Cys Leu
465                 470                 475                 480

Lys Asp Arg His Asp Phe Gly Phe Pro Gln Glu Glu Phe Gly Asn Gln
                485                 490                 495

Phe Gln Lys Ala Glu Thr Ile Pro Val Leu His Glu Met Ile Gln Gln
            500                 505                 510

Ile Phe Asn Leu Phe Ser Thr Lys Asp Ser Ser Ala Ala Trp Asp Glu
        515                 520                 525

Thr Leu Leu Asp Lys Phe Tyr Thr Glu Leu Tyr Gln Gln Leu Asn Asp
    530                 535                 540

Leu Glu Ala Cys Val Ile Gln Gly Val Gly Val Ala Glu Thr Pro Leu
545                 550                 555                 560

Met Lys Glu Asp Ser Ile Leu Ala Val Arg Lys Tyr Phe Gln Arg Ile
                565                 570                 575

Thr Leu Tyr Leu Lys Glu Lys Lys Tyr Ser Pro Cys Ala Trp Glu Val
            580                 585                 590

Val Arg Asp Glu Ile Met Arg Ser Phe Ser Leu Ser Thr Asn Leu Gln
        595                 600                 605

Glu Ser Leu Arg Ser Lys Glu
    610                 615


<210> SEQ ID NO 69
<211> LENGTH: 615
<212> TYPE: PRT
<213> ORGANISM: Artificial
<220> FEATURE:
<223> OTHER INFORMATION: A10.21 IgG1 IFN

<400> SEQUENCE: 69

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
```

-continued

```
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Cys Asp Leu Pro Gln Thr His Ser Leu Gly Ser Arg Arg Thr
    450                 455                 460

Leu Met Leu Leu Ala Gln Met Arg Arg Ile Ser Leu Phe Ser Cys Leu
465                 470                 475                 480

Lys Asp Arg His Asp Phe Gly Phe Pro Gln Glu Glu Phe Gly Asn Gln
                485                 490                 495

Phe Gln Lys Ala Glu Thr Ile Pro Val Leu His Glu Met Ile Gln Gln
            500                 505                 510

Ile Phe Asn Leu Phe Ser Thr Lys Asp Ser Ser Ala Ala Trp Asp Glu
        515                 520                 525
```

Thr Leu Leu Asp Lys Phe Tyr Thr Glu Leu Tyr Gln Gln Leu Asn Asp
    530                 535                 540

Leu Glu Ala Cys Val Ile Gln Gly Val Gly Val Ala Glu Thr Pro Leu
545                 550                 555                 560

Met Lys Glu Asp Ser Ile Leu Ala Val Arg Lys Tyr Phe Gln Arg Ile
                565                 570                 575

Thr Leu Tyr Leu Lys Glu Lys Lys Tyr Ser Pro Cys Ala Trp Glu Val
            580                 585                 590

Val Arg Asp Glu Ile Met Arg Ser Phe Ser Leu Ser Thr Asn Leu Gln
        595                 600                 605

Glu Ser Leu Arg Ser Lys Glu
    610                 615

<210> SEQ ID NO 70
<211> LENGTH: 615
<212> TYPE: PRT
<213> ORGANISM: Artificial
<220> FEATURE:
<223> OTHER INFORMATION: A10.21 IgG1 IFN

<400> SEQUENCE: 70

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Cys Asp Leu Pro Gln Thr His Ser Leu Gly Ser Arg Arg Thr
    450                 455                 460

Leu Met Leu Leu Ala Gln Met Arg Arg Ile Ser Leu Phe Ser Cys Leu
465                 470                 475                 480

Lys Asp Arg His Asp Phe Gly Phe Pro Gln Glu Glu Phe Gly Asn Gln
                485                 490                 495

Phe Gln Lys Ala Glu Thr Ile Pro Val Leu His Glu Met Ile Gln Gln
            500                 505                 510

Ile Phe Asn Leu Phe Ser Thr Lys Asp Ser Ser Ala Ala Trp Asp Glu
        515                 520                 525

Thr Leu Leu Asp Lys Phe Tyr Thr Glu Leu Tyr Gln Gln Leu Asn Asp
    530                 535                 540

Leu Glu Ala Cys Val Ile Gln Gly Val Gly Val Ala Glu Thr Pro Leu
545                 550                 555                 560

Met Lys Glu Asp Ser Ile Leu Ala Val Arg Lys Tyr Phe Gln Arg Ile
                565                 570                 575

Thr Leu Tyr Leu Lys Glu Lys Lys Tyr Ser Pro Cys Ala Trp Glu Val
            580                 585                 590

Val Arg Asp Glu Ile Met Arg Ser Phe Ser Leu Ser Thr Asn Leu Gln
        595                 600                 605

Glu Ser Leu Arg Ser Lys Glu
    610                 615

<210> SEQ ID NO 71
<211> LENGTH: 615
<212> TYPE: PRT
<213> ORGANISM: Artificial
<220> FEATURE:
<223> OTHER INFORMATION: A10.21 IgG1 IFN

<400> SEQUENCE: 71

Glu Val Gln Leu Val Gln Ser Gly Ala Glu Val Lys Lys Pro Gly Ala
1               5                   10                  15

-continued

```
Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly Lys Cys Asp Leu Pro Gln Thr His Ser Leu Gly Ser Arg Arg Thr
    450                 455                 460

Leu Met Leu Leu Ala Gln Met Arg Arg Ile Ser Leu Phe Ser Cys Leu
465                 470                 475                 480

Lys Asp Arg His Asp Phe Gly Phe Pro Gln Glu Glu Phe Gly Asn Gln
                485                 490                 495

Phe Gln Lys Ala Glu Thr Ile Pro Val Leu His Glu Met Ile Gln Gln
            500                 505                 510

Ile Phe Asn Leu Phe Ser Thr Lys Asp Ser Ser Ala Ala Trp Asp Glu
        515                 520                 525

Thr Leu Leu Asp Lys Phe Tyr Thr Glu Leu Tyr Gln Gln Leu Asn Asp
    530                 535                 540

Leu Glu Ala Cys Val Ile Gln Gly Val Gly Val Ala Glu Thr Pro Leu
545                 550                 555                 560

Met Lys Glu Asp Ser Ile Leu Ala Val Arg Lys Tyr Phe Gln Arg Ile
                565                 570                 575

Thr Leu Tyr Leu Lys Glu Lys Lys Tyr Ser Pro Cys Ala Trp Glu Val
            580                 585                 590

Val Arg Asp Glu Ile Met Arg Ser Phe Ser Leu Ser Thr Asn Leu Gln
        595                 600                 605

Glu Ser Leu Arg Ser Lys Glu
    610                 615


<210> SEQ ID NO 72
<211> LENGTH: 611
<212> TYPE: PRT
<213> ORGANISM: Artificial
<220> FEATURE:
<223> OTHER INFORMATION: A10.21 IgG2 IFN

<400> SEQUENCE: 72

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

```
Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Cys Asp
        435                 440                 445

Leu Pro Gln Thr His Ser Leu Gly Ser Arg Arg Thr Leu Met Leu Leu
    450                 455                 460

Ala Gln Met Arg Arg Ile Ser Leu Phe Ser Cys Leu Lys Asp Arg His
465                 470                 475                 480

Asp Phe Gly Phe Pro Gln Glu Glu Phe Gly Asn Gln Phe Gln Lys Ala
                485                 490                 495

Glu Thr Ile Pro Val Leu His Glu Met Ile Gln Gln Ile Phe Asn Leu
            500                 505                 510

Phe Ser Thr Lys Asp Ser Ser Ala Ala Trp Asp Glu Thr Leu Leu Asp
        515                 520                 525

Lys Phe Tyr Thr Glu Leu Tyr Gln Gln Leu Asn Asp Leu Glu Ala Cys
    530                 535                 540

Val Ile Gln Gly Val Gly Val Ala Glu Thr Pro Leu Met Lys Glu Asp
545                 550                 555                 560

Ser Ile Leu Ala Val Arg Lys Tyr Phe Gln Arg Ile Thr Leu Tyr Leu
                565                 570                 575

Lys Glu Lys Lys Tyr Ser Pro Cys Ala Trp Glu Val Val Arg Asp Glu
            580                 585                 590

Ile Met Arg Ser Phe Ser Leu Ser Thr Asn Leu Gln Glu Ser Leu Arg
```

595 600 605

Ser Lys Glu
610

<210> SEQ ID NO 73
<211> LENGTH: 611
<212> TYPE: PRT
<213> ORGANISM: Artificial
<220> FEATURE:
<223> OTHER INFORMATION: A10.21 IgG2 IFN

<400> SEQUENCE: 73

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Ser
20 25 30

Val Met Asn Trp Val Gln Gln Ala Pro Gly Lys Gly Leu Glu Trp Met
35 40 45

Gly Trp Ile Asp Pro Glu Tyr Gly Arg Thr Asp Val Ala Glu Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Thr Lys Tyr Asn Ser Gly Tyr Gly Phe Pro Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Asn Phe Gly Thr Gln Thr Tyr Thr Cys Asn Val Asp His Lys
195 200 205

Pro Ser Asn Thr Lys Val Asp Lys Thr Val Glu Arg Lys Cys Cys Val
210 215 220

Glu Cys Pro Pro Cys Pro Ala Pro Pro Val Ala Gly Pro Ser Val Phe
225 230 235 240

Leu Phe Pro Pro Lys Pro Lys Asp Thr Leu Tyr Ile Thr Arg Glu Pro
245 250 255

Glu Val Thr Cys Val Val Val Asp Val Ser His Glu Asp Pro Glu Val
260 265 270

Gln Phe Asn Trp Tyr Val Asp Gly Val Glu Val His Asn Ala Lys Thr
275 280 285

Lys Pro Arg Glu Glu Gln Phe Asn Ser Thr Phe Arg Val Val Ser Val
290 295 300

Leu Thr Val Val His Gln Asp Trp Leu Asn Gly Lys Glu Tyr Lys Cys
305 310 315 320

Lys Val Ser Asn Lys Gly Leu Pro Ala Pro Ile Glu Lys Thr Ile Ser
325 330 335

Lys Thr Lys Gly Gln Pro Arg Glu Pro Gln Val Tyr Thr Leu Pro Pro

```
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Cys Asp
        435                 440                 445

Leu Pro Gln Thr His Ser Leu Gly Ser Arg Arg Thr Leu Met Leu Leu
    450                 455                 460

Ala Gln Met Arg Arg Ile Ser Leu Phe Ser Cys Leu Lys Asp Arg His
465                 470                 475                 480

Asp Phe Gly Phe Pro Gln Glu Glu Phe Gly Asn Gln Phe Gln Lys Ala
                485                 490                 495

Glu Thr Ile Pro Val Leu His Glu Met Ile Gln Gln Ile Phe Asn Leu
            500                 505                 510

Phe Ser Thr Lys Asp Ser Ser Ala Ala Trp Asp Glu Thr Leu Leu Asp
        515                 520                 525

Lys Phe Tyr Thr Glu Leu Tyr Gln Gln Leu Asn Asp Leu Glu Ala Cys
    530                 535                 540

Val Ile Gln Gly Val Gly Val Ala Glu Thr Pro Leu Met Lys Glu Asp
545                 550                 555                 560

Ser Ile Leu Ala Val Arg Lys Tyr Phe Gln Arg Ile Thr Leu Tyr Leu
                565                 570                 575

Lys Glu Lys Lys Tyr Ser Pro Cys Ala Trp Glu Val Val Arg Asp Glu
            580                 585                 590

Ile Met Arg Ser Phe Ser Leu Ser Thr Asn Leu Gln Glu Ser Leu Arg
        595                 600                 605

Ser Lys Glu
    610


<210> SEQ ID NO 74
<211> LENGTH: 612
<212> TYPE: PRT
<213> ORGANISM: Artificial
<220> FEATURE:
<223> OTHER INFORMATION: A10.43 IgG4 IFN

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
```

-continued

```
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510
```

Leu Phe Ser Thr Lys Asp Ser Ser Ala Ala Trp Asp Glu Thr Leu Leu
515 520 525

Asp Lys Phe Tyr Thr Glu Leu Tyr Gln Gln Leu Asn Asp Leu Glu Ala
530 535 540

Cys Val Ile Gln Gly Val Gly Val Ala Glu Thr Pro Leu Met Lys Glu
545 550 555 560

Asp Ser Ile Leu Ala Val Arg Lys Tyr Phe Gln Arg Ile Thr Leu Tyr
565 570 575

Leu Lys Glu Lys Lys Tyr Ser Pro Cys Ala Trp Glu Val Val Arg Asp
580 585 590

Glu Ile Met Arg Ser Phe Ser Leu Ser Thr Asn Leu Gln Glu Ser Leu
595 600 605

Arg Ser Lys Glu
610

<210> SEQ ID NO 75
<211> LENGTH: 612
<212> TYPE: PRT
<213> ORGANISM: Artificial
<220> FEATURE:
<223> OTHER INFORMATION: R10A2 IgG4 IFN
<220> FEATURE:
<221> NAME/KEY: VARIANT
<222> LOCATION: (553)..(553)
<223> OTHER INFORMATION: Where Xaa can be any amino acid selected from
A, C, D, E, F, G, H, I, L, K, M, N, P, Q, R, S, V, W, Y

<400> SEQUENCE: 75

Glu Val Gln Leu Gln Gln Ser Gly Pro Glu Val Gly Arg Pro Gly Ser
1 5 10 15

Ser Val Lys Ile Ser Cys Lys Ala Ser Gly Tyr Thr Phe Thr Asp Ser
20 25 30

Val Met Asn Trp Val Lys Gln Ser Pro Gly Gln Gly Leu Glu Trp Ile
35 40 45

Gly Trp Ile Asp Pro Glu Tyr Gly Arg Thr Asp Val Ala Glu Lys Phe
50 55 60

Lys Lys Lys Ala Thr Leu Thr Ala Asp Ser Ser Ser Ser Thr Ala Tyr
65 70 75 80

Ile Tyr Leu Ser Gly Leu Thr Ser Glu Asp Thr Ala Thr Tyr Phe Cys
85 90 95

Ala Arg Thr Lys Tyr Asn Ser Gly Tyr Gly Phe Pro Tyr Trp Gly Gln
100 105 110

Gly Ser Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

-continued

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Xaa Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Asp
            580                 585                 590

Glu Ile Met Arg Ser Phe Ser Leu Ser Thr Asn Leu Gln Glu Ser Leu
        595                 600                 605

Arg Ser Lys Glu
    610
```

<210> SEQ ID NO 76
<211> LENGTH: 612
<212> TYPE: PRT

```
<213> ORGANISM: Artificial
<220> FEATURE:
<223> OTHER INFORMATION: A10.152 IgG4 IFN

<400> SEQUENCE: 76

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln His Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys Cys
435 440 445

Asp Leu Pro Gln Thr His Ser Leu Gly Ser Arg Arg Thr Leu Met Leu
450 455 460

Leu Ala Gln Met Arg Arg Ile Ser Leu Phe Ser Cys Leu Lys Asp Arg
465 470 475 480

His Asp Phe Gly Phe Pro Gln Glu Glu Phe Gly Asn Gln Phe Gln Lys
485 490 495

Ala Glu Thr Ile Pro Val Leu His Glu Met Ile Gln Gln Ile Phe Asn
500 505 510

Leu Phe Ser Thr Lys Asp Ser Ser Ala Ala Trp Asp Glu Thr Leu Leu
515 520 525

Asp Lys Phe Tyr Thr Glu Leu Tyr Gln Gln Leu Asn Asp Leu Glu Ala
530 535 540

Cys Val Ile Gln Gly Val Gly Val Ala Glu Thr Pro Leu Met Lys Glu
545 550 555 560

Asp Ser Ile Leu Ala Val Arg Lys Tyr Phe Gln Arg Ile Thr Leu Tyr
565 570 575

Leu Lys Glu Lys Lys Tyr Ser Pro Cys Ala Trp Glu Val Val Arg Asp
580 585 590

Glu Ile Met Arg Ser Phe Ser Leu Ser Thr Asn Leu Gln Glu Ser Leu
595 600 605

Arg Ser Lys Glu
610

<210> SEQ ID NO 77
<211> LENGTH: 613
<212> TYPE: PRT
<213> ORGANISM: Artificial
<220> FEATURE:
<223> OTHER INFORMATION: A02.12 IgG4 IFN

<400> SEQUENCE: 77

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Ser Trp Ile Arg Gln His Pro Gly Lys Gly Leu Glu
35 40 45

Trp Ile Gly Tyr Ile Tyr Tyr Ser Gly Ser Thr Asn Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Val Gly Gly Ala Gly Gly Trp Pro Leu Asp Val Trp Gly
100 105 110

Gln Gly Thr Thr Val Thr Val Ser Ser Ala Ser Thr Lys Gly Pro Ser
115 120 125

Val Phe Pro Leu Ala Pro Cys Ser Arg Ser Thr Ser Glu Ser Thr Ala

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

Cys Asp Leu Pro Gln Thr His Ser Leu Gly Ser Arg Arg Thr Leu Met
    450                 455                 460

Leu Leu Ala Gln Met Arg Arg Ile Ser Leu Phe Ser Cys Leu Lys Asp
465                 470                 475                 480

Arg His Asp Phe Gly Phe Pro Gln Glu Glu Phe Gly Asn Gln Phe Gln
                485                 490                 495

Lys Ala Glu Thr Ile Pro Val Leu His Glu Met Ile Gln Gln Ile Phe
            500                 505                 510

Asn Leu Phe Ser Thr Lys Asp Ser Ser Ala Ala Trp Asp Glu Thr Leu
        515                 520                 525

Leu Asp Lys Phe Tyr Thr Glu Leu Tyr Gln Gln Leu Asn Asp Leu Glu
    530                 535                 540

Ala Cys Val Ile Gln Gly Val Gly Val Ala Glu Thr Pro Leu Met Lys
545                 550                 555                 560
```

```
Glu Asp Ser Ile Leu Ala Val Arg Lys Tyr Phe Gln Arg Ile Thr Leu
                565                 570                 575

Tyr Leu Lys Glu Lys Lys Tyr Ser Pro Cys Ala Trp Glu Val Val Arg
            580                 585                 590

Asp Glu Ile Met Arg Ser Phe Ser Leu Ser Thr Asn Leu Gln Glu Ser
        595                 600                 605

Leu Arg Ser Lys Glu
    610


<210> SEQ ID NO 78
<211> LENGTH: 566
<212> TYPE: PRT
<213> ORGANISM: Artificial
<220> FEATURE:
<223> OTHER INFORMATION: OPG-Fc (IgG2) IFN

<400> SEQUENCE: 78

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
        35                  40                  45

Tyr Thr Asp Ser Trp His Thr Ser Asp Glu Cys Leu Tyr Cys Ser Pro
    50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Gly Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
    130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Glu Arg Lys
                165                 170                 175

Cys Cys Val Glu Cys Pro Pro Cys Pro Ala Pro Pro Val Ala Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Gln Phe Asn Trp Tyr Val Asp Gly Val Glu Val His Asn
225                 230                 235                 240

Ala Lys Thr Lys Pro Arg Glu Glu Gln Phe Asn Ser Thr Phe Arg Val
                245                 250                 255

Val Ser Val Leu Thr Val Val His Gln Asp Trp Leu Asn Gly Lys Glu
            260                 265                 270

Tyr Lys Cys Lys Val Ser Asn Lys Gly Leu Pro Ala Pro Ile Glu Lys
        275                 280                 285

Thr Ile Ser Lys Thr Lys Gly Gln Pro Arg Glu Pro Gln Val Tyr Thr
    290                 295                 300
```

Leu Pro Pro Ser Arg Glu Glu Met Thr Lys Asn Gln Val Ser Leu Thr
305 310 315 320

Cys Leu Val Lys Gly Phe Tyr Pro Ser Asp Ile Ala Val Glu Trp Glu
325 330 335

Ser Asn Gly Gln Pro Glu Asn Asn Tyr Lys Thr Thr Pro Pro Met Leu
340 345 350

Asp Ser Asp Gly Ser Phe Phe Leu Tyr Ser Lys Leu Thr Val Asp Lys
355 360 365

Ser Arg Trp Gln Gln Gly Asn Val Phe Ser Cys Ser Val Met His Glu
370 375 380

Ala Leu His Asn His Tyr Thr Gln Lys Ser Leu Ser Leu Ser Pro Gly
385 390 395 400

Lys Cys Asp Leu Pro Gln Thr His Ser Leu Gly Ser Arg Arg Thr Leu
405 410 415

Met Leu Leu Ala Gln Met Arg Arg Ile Ser Leu Phe Ser Cys Leu Lys
420 425 430

Asp Arg His Asp Phe Gly Phe Pro Gln Glu Glu Phe Gly Asn Gln Phe
435 440 445

Gln Lys Ala Glu Thr Ile Pro Val Leu His Glu Met Ile Gln Gln Ile
450 455 460

Phe Asn Leu Phe Ser Thr Lys Asp Ser Ser Ala Ala Trp Asp Glu Thr
465 470 475 480

Leu Leu Asp Lys Phe Tyr Thr Glu Leu Tyr Gln Gln Leu Asn Asp Leu
485 490 495

Glu Ala Cys Val Ile Gln Gly Val Gly Val Ala Glu Thr Pro Leu Met
500 505 510

Lys Glu Asp Ser Ile Leu Ala Val Arg Lys Tyr Phe Gln Arg Ile Thr
515 520 525

Leu Tyr Leu Lys Glu Lys Lys Tyr Ser Pro Cys Ala Trp Glu Val Val
530 535 540

Arg Asp Glu Ile Met Arg Ser Phe Ser Leu Ser Thr Asn Leu Gln Glu
545 550 555 560

Ser Leu Arg Ser Lys Glu
565

<210> SEQ ID NO 79
<211> LENGTH: 614
<212> TYPE: PRT
<213> ORGANISM: Artificial
<220> FEATURE:
<223> OTHER INFORMATION: Anti-CD138 IgG4 IFN

<400> SEQUENCE: 79

Gln Val Gln Leu Gln Gln Ser Gly Ser Glu Leu Met Met Pro Gly Ala
1 5 10 15

Ser Val Lys Ile Ser Cys Lys Ala Thr Gly Tyr Thr Phe Ser Asn Tyr
20 25 30

Trp Ile Glu Trp Val Lys Gln Arg Pro Gly His Gly Leu Glu Trp Ile
35 40 45

Gly Glu Ile Leu Pro Gly Thr Gly Arg Thr Ile Tyr Asn Glu Lys Phe
50 55 60

Lys Gly Lys Ala Thr Phe Thr Ala Asp Ile Ser Ser Asn Thr Val Gln
65 70 75 80

Met Gln Leu Ser Ser Leu Thr Ser Glu Asp Ser Ala Val Tyr Tyr Cys
85 90 95

-continued

```
Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Cys Asp Leu Pro Gln Thr His Ser Leu Gly Ser Arg Arg Thr Leu
    450                 455                 460

Met Leu Leu Ala Gln Met Arg Arg Ile Ser Leu Phe Ser Cys Leu Lys
465                 470                 475                 480

Asp Arg His Asp Phe Gly Phe Pro Gln Glu Glu Phe Gly Asn Gln Phe
                485                 490                 495

Gln Lys Ala Glu Thr Ile Pro Val Leu His Glu Met Ile Gln Gln Ile
            500                 505                 510
```

```
Phe Asn Leu Phe Ser Thr Lys Asp Ser Ser Ala Ala Trp Asp Glu Thr
        515                 520                 525

Leu Leu Asp Lys Phe Tyr Thr Glu Leu Tyr Gln Gln Leu Asn Asp Leu
    530                 535                 540

Glu Ala Cys Val Ile Gln Gly Val Gly Val Ala Glu Thr Pro Leu Met
545                 550                 555                 560

Lys Glu Asp Ser Ile Leu Ala Val Arg Lys Tyr Phe Gln Arg Ile Thr
                565                 570                 575

Leu Tyr Leu Lys Glu Lys Lys Tyr Ser Pro Cys Ala Trp Glu Val Val
            580                 585                 590

Arg Asp Glu Ile Met Arg Ser Phe Ser Leu Ser Thr Asn Leu Gln Glu
        595                 600                 605

Ser Leu Arg Ser Lys Glu
    610
```

<210> SEQ ID NO 80
<211> LENGTH: 612
<212> TYPE: PRT
<213> ORGANISM: Artificial
<220> FEATURE:
<223> OTHER INFORMATION: Anti-HLA IgG4 IFN

<400> SEQUENCE: 80

```
Gln Val Gln Leu Lys Gln Ser Gly Pro Gly Leu Val Gln Pro Ser Gln
1               5                   10                  15

Ser Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Arg Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460

Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Asp
            580                 585                 590

Glu Ile Met Arg Ser Phe Ser Leu Ser Thr Asn Leu Gln Glu Ser Leu
        595                 600                 605

Arg Ser Lys Glu
    610
```

<210> SEQ ID NO 81
<211> LENGTH: 214
<212> TYPE: PRT
<213> ORGANISM: Artificial
<220> FEATURE:
<223> OTHER INFORMATION: A10.21 and A10.43 light chain

<400> SEQUENCE: 81

-continued

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Asp Ser Asp
20 25 30

Val Asp Trp Tyr Gln Gln Lys Pro Gly Lys Ala Pro Lys Leu Leu Ile
35 40 45

Tyr Lys Ala Ser Asn Asp Tyr Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Met Gln Ser Asn Thr His Pro Arg
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 82
<211> LENGTH: 214
<212> TYPE: PRT
<213> ORGANISM: Artificial
<220> FEATURE:
<223> OTHER INFORMATION: R10A2 light chain

<400> SEQUENCE: 82

Asp Ile Val Met Thr Gln Ser Pro Thr Ser Ile Ser Ile Ser Val Gly
1 5 10 15

Glu Arg Val Thr Met Asn Cys Lys Ala Ser Gln Asn Val Asp Ser Asp
20 25 30

Val Asp Trp Tyr Gln Gln Lys Thr Gly Gln Ser Pro Lys Leu Leu Ile
35 40 45

Tyr Lys Ala Ser Asn Arg Tyr Thr Gly Val Pro Asp Arg Phe Thr Gly
50 55 60

Ser Gly Ser Gly Thr Asp Phe Thr Phe Thr Ile Ser Asn Met Gln Ala
65 70 75 80

Glu Asp Leu Ala Val Tyr Tyr Cys Met Gln Ser Asn Thr His Pro Arg
85 90 95

Thr Phe Gly Gly Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 83
<211> LENGTH: 614
<212> TYPE: PRT
<213> ORGANISM: Artificial
<220> FEATURE:
<223> OTHER INFORMATION: A10.21 IgG1 IFN

<400> SEQUENCE: 83

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Ser
20 25 30

Val Met Asn Trp Val Gln Gln Ala Pro Gly Lys Gly Leu Glu Trp Met
35 40 45

Gly Trp Ile Asp Pro Glu Tyr Gly Arg Thr Asp Val Ala Glu Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Thr Lys Tyr Asn Ser Gly Tyr Gly Phe Pro Tyr Trp Gly Gln
100 105 110

Gly Thr Thr Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Cys Asp Leu Pro Gln Thr His Ser Leu Gly Ser Arg Arg Thr
    450                 455                 460

Leu Met Leu Leu Ala Gln Met Arg Arg Ile Ser Leu Phe Ser Cys Leu
465                 470                 475                 480

Lys Asp Arg His Asp Phe Gly Phe Pro Gln Glu Glu Phe Gly Asn Gln
                485                 490                 495

Phe Gln Lys Ala Glu Thr Ile Pro Val Leu His Glu Met Ile Gln Gln
            500                 505                 510

Ile Phe Asn Leu Phe Ser Thr Lys Asp Ser Ser Ala Ala Trp Asp Glu
        515                 520                 525

Thr Leu Leu Asp Lys Phe Tyr Thr Glu Leu Tyr Gln Gln Leu Asn Asp
    530                 535                 540

Leu Glu Ala Cys Val Ile Gln Gly Val Gly Val Glu Thr Pro Leu Met
545                 550                 555                 560

Lys Glu Asp Ser Ile Leu Ala Val Arg Lys Tyr Phe Gln Arg Ile Thr
                565                 570                 575

Leu Tyr Leu Lys Glu Lys Lys Tyr Ser Pro Cys Ala Trp Glu Val Val
            580                 585                 590

Arg Asp Glu Ile Met Arg Ser Phe Ser Leu Ser Thr Asn Leu Gln Glu
        595                 600                 605

Ser Leu Arg Ser Lys Glu
    610
```

<210> SEQ ID NO 84
<211> LENGTH: 222
<212> TYPE: PRT
<213> ORGANISM: Artificial
<220> FEATURE:
<223> OTHER INFORMATION: A02.12 lambda light chain

<400> SEQUENCE: 84

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30
```

-continued

```
Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
    130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220


<210> SEQ ID NO 85
<211> LENGTH: 214
<212> TYPE: PRT
<213> ORGANISM: Artificial
<220> FEATURE:
<223> OTHER INFORMATION: Anti-CD138 light chain

<400> SEQUENCE: 85

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 86
<211> LENGTH: 215
<212> TYPE: PRT
<213> ORGANISM: Artificial
<220> FEATURE:
<223> OTHER INFORMATION: Anti-HLA light chain

<400> SEQUENCE: 86

Ser Ile Val Met Thr Gln Thr Pro Lys Phe Leu Leu Val Ser Ala Gly
1 5 10 15

Asp Arg Val Thr Ile Thr Cys Lys Ala Ser Gln Ser Val Ser Asn Asp
20 25 30

Val Ala Trp Tyr Gln Gln Lys Pro Gly Gln Ser Pro Lys Leu Leu Ile
35 40 45

Tyr Tyr Ala Ser Asn Arg Tyr Thr Gly Val Pro Asp Arg Phe Thr Gly
50 55 60

Ser Gly Tyr Gly Thr Asp Phe Thr Phe Thr Ile Ser Thr Val Gln Ala
65 70 75 80

Glu Asp Leu Ala Val Tyr Phe Cys Gln Gln Asp Tyr Ser Ser Pro Pro
85 90 95

Trp Thr Phe Gly Gly Gly Thr Lys Leu Glu Ile Arg Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 87
<211> LENGTH: 612
<212> TYPE: PRT
<213> ORGANISM: Artificial
<220> FEATURE:
<223> OTHER INFORMATION: A10.21 IgG4 (S228P) IFN (A145D, T106A)

<400> SEQUENCE: 87

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Ser
20 25 30

Val Met Asn Trp Val Gln Gln Ala Pro Gly Lys Gly Leu Glu Trp Met
35 40 45

```
Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Cys
        435                 440                 445

Asp Leu Pro Gln Thr His Ser Leu Gly Ser Arg Arg Thr Leu Met Leu
    450                 455                 460
```

```
Leu Ala Gln Met Arg Arg Ile Ser Leu Phe Ser Cys Leu Lys Asp Arg
465                 470                 475                 480

His Asp Phe Gly Phe Pro Gln Glu Glu Phe Gly Asn Gln Phe Gln Lys
                485                 490                 495

Ala Glu Thr Ile Pro Val Leu His Glu Met Ile Gln Gln Ile Phe Asn
            500                 505                 510

Leu Phe Ser Thr Lys Asp Ser Ser Ala Ala Trp Asp Glu Thr Leu Leu
        515                 520                 525

Asp Lys Phe Tyr Thr Glu Leu Tyr Gln Gln Leu Asn Asp Leu Glu Ala
    530                 535                 540

Cys Val Ile Gln Gly Val Gly Val Ala Glu Thr Pro Leu Met Lys Glu
545                 550                 555                 560

Asp Ser Ile Leu Ala Val Arg Lys Tyr Phe Gln Arg Ile Thr Leu Tyr
                565                 570                 575

Leu Lys Glu Lys Lys Tyr Ser Pro Cys Ala Trp Glu Val Val Arg Asp
            580                 585                 590

Glu Ile Met Arg Ser Phe Ser Leu Ser Thr Asn Leu Gln Glu Ser Leu
        595                 600                 605

Arg Ser Lys Glu
    610
```

<210> SEQ ID NO 88
<211> LENGTH: 495
<212> TYPE: DNA
<213> ORGANISM: Artificial
<220> FEATURE:
<223> OTHER INFORMATION: IFN alpha-2-beta

<400> SEQUENCE: 88

```
tgtgatctgc ctcaaaccca cagcctgggt agcaggagga ccttgatgct cctggcacag     60

atgaggagaa tctctctttt ctcctgcttg aaggacagac atgactttgg atttccccag    120

gaggagtttg gcaaccagtt ccaaaaggct gaaaccatcc ctgtcctcca tgagatgatc    180

cagcagatct tcaatctctt cagcacaaag gactcatctg ctgcttggga tgagaccctc    240

ctagacaaat tctacactga actctaccag cagctgaatg acctggaagc ctgtgtgata    300

caggggggtgg gggtgacaga gactcccctg atgaaggagg actccattct ggctgtgagg    360

aaatacttcc aaagaatcac tctctatctg aaagagaaga aatacagccc ttgtgcctgg    420

gaggttgtca gagcagaaat catgagatct tttttctttgt caacaaactt gcaagaaagt    480

ttaagaagta aggaa                                                     495
```

<210> SEQ ID NO 89
<211> LENGTH: 1341
<212> TYPE: DNA
<213> ORGANISM: Artificial
<220> FEATURE:
<223> OTHER INFORMATION: Polynucleotide of 10.21 as an IgG2
      incorporating S228P

<400> SEQUENCE: 89

```
gaagtgcagc tggtgcagtc tggcgccgaa gtgaagaaac ccggcgctac cgtgaagatc     60

tcctgcaagg tgtccggcta caccttcacc gactccgtga tgaactgggt gcagcaggcc    120

cctggcaagg gcctggaatg gatgggctgg atcgaccccg agtacggcag aaccgacgtg    180

gccgagaagt tccagggcag agtgaccatc accgccgaca cctccaccga caccgcctac    240

atggaactgt cctccctgcg gagcgaggac accgccgtgt actactgcgc ccggaccaag    300
```

tacaactccg gctacggctt cccctactgg ggccagggca ccaccgtgac cgtgtcctcc 360
gcctccacca agggcccctc cgtgttccct ctggcccctt gctcccggtc cacctccgag 420
tctaccgccg ctctgggctg cctggtcaag gactacttcc ccgagcctgt gacagtgtcc 480
tggaactctg gcgccctgac ctccggcgtg cacaccttcc ctgccgtgct gcagtcctcc 540
ggcctgtact ccctgtcctc cgtcgtgacc gtgccttcca gctccctggg caccaagacc 600
tacacctgta acgtggacca caagccctcc aacaccaagg tggacaagcg ggtggaatct 660
aagtacggcc ctccctgccc cccctgccct gcccctgaat ttctgggcgg accttccgtg 720
ttcctgttcc ccccaaagcc caaggacacc ctgatgatct cccggacccc cgaagtgacc 780
tgcgtggtgg tggacgtgtc ccaagaggac cccgaggtgc agttcaattg gtacgtggac 840
ggcgtggaag tgcacaacgc caagaccaag cccagagagg aacagttcaa ctccacctac 900
cgggtggtgt ccgtgctgac cgtgctgcac caggactggc tgaacggcaa agaatacaag 960
tgcaaagtct ccaacaaggg cctgccctcc agcatcgaaa agaccatctc caaggccaag 1020
ggacagcccc gcgagcccca ggtgtacacc ctgcccccta gccaagagga aatgaccaag 1080
aaccaggtgt ccctgacctg cctcgtgaag ggcttctacc cctccgatat cgccgtggaa 1140
tgggagtcca acggccagcc cgagaacaac tacaagacca ccccccctgt gctggactcc 1200
gacggctcct tcttcctgta ctctcggctg accgtggaca agtcccggtg gcaagagggc 1260
aacgtgttct cctgctccgt gatgcacgag gccctgcaca accactacac ccagaagtcc 1320
ctgtccctga gcctgggcaa g 1341

<210> SEQ ID NO 90
<211> LENGTH: 1341
<212> TYPE: DNA
<213> ORGANISM: Artificial
<220> FEATURE:
<223> OTHER INFORMATION: Polynucleotide sequence of 10.43 as an IgG4 incorporating S228P

<400> SEQUENCE: 90
caggtgcagc tggtgcagtc tggcgccgaa gtgaagaaac ctggcgcctc cgtgaaggtg 60
tcctgcaagg tgtccggcta caccctgacc gactccgtga tgaactgggt ccgacaggcc 120
cctggcaagg gcctggaatg gatgggctgg atcgaccccg agtacggcag aaccgacgtg 180
gcccagaaat tccagggcag agtgaccatg accgccgaca cctccaccga caccgcctac 240
atggaactgt cctccctgcg gagcgaggac accgccgtgt actactgcgc ccggaccaag 300
tacaactccg gctacggctt cccctactgg ggccagggca ccaccgtgac cgtgtcctct 360
gcttccacca agggcccctc cgtgttccct ctggcccctt gctcccggtc cacctccgag 420
tctaccgccg ctctgggctg cctggtcaag gactacttcc ccgagcctgt gacagtgtcc 480
tggaactctg gcgccctgac ctccggcgtg cacaccttcc ctgccgtgct gcagtcctcc 540
ggcctgtact ccctgtcctc cgtcgtgacc gtgccttcca gctccctggg caccaagacc 600
tacacctgta acgtggacca caagccctcc aacaccaagg tggacaagcg ggtggaatct 660
aagtacggcc ctccctgccc cccctgccct gcccctgaat ttctgggcgg accttccgtg 720
ttcctgttcc ccccaaagcc caaggacacc ctgatgatct cccggacccc cgaagtgacc 780
tgcgtggtgg tggacgtgtc ccaagaggac cccgaggtgc agttcaattg gtacgtggac 840
ggcgtggaag tgcacaacgc caagaccaag cccagagagg aacagttcaa ctccacctac 900
cgggtggtgt ccgtgctgac cgtgctgcac caggactggc tgaacggcaa agaatacaag 960
tgcaaagtct ccaacaaggg cctgccctcc agcatcgaaa agaccatctc caaggccaag 1020
ggacagcccc gcgagcccca ggtgtacacc ctgcccccta gccaagagga aatgaccaag 1080
aaccaggtgt ccctgacctg cctcgtgaag ggcttctacc cctccgatat cgccgtggaa 1140
tgggagtcca acggccagcc cgagaacaac tacaagacca ccccccctgt gctggactcc 1200
gacggctcct tcttcctgta ctctcggctg accgtggaca agtcccggtg gcaagagggc 1260
aacgtgttct cctgctccgt gatgcacgag gccctgcaca accactacac ccagaagtcc 1320
ctgtccctga gcctgggcaa g 1341

<210> SEQ ID NO 91
<211> LENGTH: 1344
<212> TYPE: DNA
<213> ORGANISM: Artificial
<220> FEATURE:
<223> OTHER INFORMATION: Polynucleotide of 2.12 formatted an an IgG4 incorporating S228P

<400> SEQUENCE: 91
cagctgcagc tgcaggaatc tggccctggc ctcgtgaagc ccagcgagac actgagcctg 60
acctgtaccg tgtccggcgg cagcatcagc agcagctcct actactggtc ctggatcaga 120
cagcaccccg gcaagggcct ggaatggatc ggctacatct actacagcgg cagcaccaac 180
tacaacccca gcctgaagtc cagagtgacc atcagcgtgg acaccagcaa gaaccagttc 240
tccctgaagc tgagcagcgt gacagccgcc gataccgccg tgtactactg tgccagagtg 300
ggcggagctg gcggctggcc tctggatgtg tggggacagg gcaccaccgt gacagtgtcc 360
tcagctagca ccaagggccc cagcgtgttc cctctggccc cttgtagcag aagcaccagc 420
gagtctacag ccgccctggg ctgcctcgtg aaggactact ttcccgagcc cgtcaccgtg 480
tcctggaact ctggcgctct gacaagcggc gtgcacacct ttccagccgt gctgcagagc 540
agcggcctgt actctctgag cagcgtcgtg accgtgccca gctctagcct gggcaccaag 600
acctacacct gtaacgtgga ccacaagccc agcaacacca aggtggacaa gcgggtggaa 660
tctaagtacg gccctccctg ccctccttgc ccagcccctg aatttctggg cggaccctcc 720
gtgttcctgt tcccccaaa gcccaaggac accctgatga tcagccggac ccccgaagtg 780
acctgcgtgg tggtggatgt gtcccaggaa gatcccgagg tgcagttcaa ttggtacgtg 840
gacggcgtgg aagtgcacaa cgccaagacc aagcccagag aggaacagtt caacagcacc 900
taccgggtgg tgtccgtgct gacagtgctg caccaggact ggctgaacgg caaagagtac 960
aagtgcaagg tgtccaacaa gggcctgcct agcagcatcg agaaaaccat cagcaaggcc 1020
aagggccagc cccgcgaacc tcaggtgtac acactgcccc ctagccagga agagatgacc 1080
aagaaccagg tgtccctgac ctgtctcgtg aaaggcttct acccctccga tatcgccgtg 1140
gaatgggaga gcaacggcca gcccgagaac aactacaaga ccacccccc tgtgctggac 1200 agcgacggct cattcttcct gtacagcaga ctgaccgtgg acaagagccg gtggcaggaa 1260
ggcaacgtgt tcagctgcag cgtgatgcac gaggccctgc acaaccacta cacccagaag 1320
tccctgtccc tgtctctggg caag 1344

<210> SEQ ID NO 92
<211> LENGTH: 1341
<212> TYPE: DNA
<213> ORGANISM: Artificial
<220> FEATURE:
<223> OTHER INFORMATION: Polynucleotide of R10A2 formatted as an IgG4 incorporating S228P

<400> SEQUENCE: 92
gaagtccagc tgcagcagtc tggccccgaa gtgggcagac ctggctcctc cgtgaagatc 60
tcctgcaagg cctccggcta caccttcacc gactccgtga tgaactgggt caagcagtct 120
cccggccagg gcctggaatg gatcggatgg atcgaccccg agtacggcag aaccgacgtg 180
gccgagaagt tcaagaagaa ggccaccctg accgccgact cctccagctc caccgcctac 240
atctacctgt ccggcctgac ctccgaggac accgccacct acttttgcgc ccggaccaag 300
tacaacagcg gctacggctt cccctactgg ggacagggct ctctcgtgac agtgtcctca 360
gcctccacca agggcccctc cgtgttccct ctggcccctt gctcccggtc cacctccgag 420
tctaccgccg ctctgggctg cctggtgaaa gactacttcc ccgagcctgt gaccgtgagc 480
tggaactctg gcgccctgac ctccggcgtg cacaccttcc ctgccgtgct gcagtcctcc 540
ggcctgtact ccctgtcctc cgtggtgaca gtgccctcct ccagcctggg caccaagacc 600
tacacctgta acgtggacca caagccctcc aacaccaagg tggacaagcg ggtggaatct 660
aagtacggcc ctccctgccc cccctgccct gcccctgaat ttctgggcgg accttccgtg 720
tttctgttcc ccccaaagcc caaggacacc ctgatgatct cccggacccc cgaagtgacc 780
tgcgtggtgg tggacgtgtc ccaggaagat ccagaggtgc agttcaattg gtacgtggac 840
ggcgtggaag tgcacaacgc caagaccaag cccagagagg aacagttcaa ctccacctac 900
cgggtggtgt ccgtgctgac cgtgctgcac caggactggc tgaacggcaa agagtacaag 960
tgcaaggtgt ccaacaaggg cctgccctcc agcatcgaaa agaccatctc caaggccaag 1020
ggccagcccc gcgagcccca ggtgtacacc ctgcccccta gccaggaaga gatgaccaag 1080
aaccaggtgt ccctgacctg tctggtgaaa ggcttctacc cctccgacat tgccgtggaa 1140
tgggagtcca acggccagcc cgagaacaac tacaagacca ccccccctgt gctggactcc 1200
gacggctcct tcttcctgta ctctcggctg acagtggata agtcccggtg gcaggaaggc 1260
aacgtgttct cctgcagcgt gatgcacgag gccctgcaca accactatac ccagaagtcc 1320
ctgtccctga gcctgggcaa g 1341

<210> SEQ ID NO 93
<211> LENGTH: 642
<212> TYPE: DNA
<213> ORGANISM: Artificial
<220> FEATURE:
<223> OTHER INFORMATION: Polynucleotide sequence of R10A2 VK

<400> SEQUENCE: 93
gacatcgtga tgacccagag ccccacctcc atctccatca gcgtgggcga gcgcgtgacc 60
atgaactgca aggcctccca gaacgtggac agcgacgtgg actggtatca gcagaaaacc 120
ggccagtccc ccaagctgct gatctacaag gccagcaaca gatacaccgg cgtgcccgac 180
aggttcaccg gctctggctc tggaaccgac ttcaccttca ccatcagcaa catgcaggcc 240
gaggatctgg ccgtgtacta ctgtatgcag tccaacaccc acccccggac cttcggcgga 300
ggcaccaaac tggaactgaa gcggaccgtg gccgctccca gcgtgttcat cttccccccc 360
agcgacgagc agctgaagag cggcaccgcc agcgtggtct gcctgctgaa caacttctac 420
ccccgggagg ccaaggtgca gtggaaggtg gacaacgccc tgcagtctgg caacagccag 480
gaaagcgtca ccgagcagga cagcaaggat agcacctaca gcctgagcag caccctgacc 540
ctgagcaagg ccgactacga gaagcacaag gtgtacgcct gcgaggtcac ccaccagggc 600
ctgtctagcc ccgtcaccaa gagcttcaac cggggcgagt gc 642

<210> SEQ ID NO 94
<211> LENGTH: 642
<212> TYPE: DNA
<213> ORGANISM: Artificial
<220> FEATURE:
<223> OTHER INFORMATION: Polynucleotide sequence of VK used to generate antibody 10.21 and antibody 10.43

<400> SEQUENCE: 94
gacatccaga tgacccagtc cccctccagc ctgtccgctt ccgtgggcga cagagtgacc 60
atcacatgca aggcctccca gaacgtggac tccgacgtgg actggtatca gcagaagccc 120
ggcaaggccc ccaagctgct gatctacaag gcctccaacg actacaccgg cgtgccctcc 180
agattctccg gctccggctc tggcaccgac ttcaccttca ccatctccag cctgcagccc 240
gaggatatcg ccacctacta ctgcatgcag agcaacaccc acccccggac cttcggcgga 300
ggcaccaagg tggaaatcaa gcggaccgtg gccgctccct ccgtgttcat cttcccaccc 360
tccgacgagc agctgaagtc cggcaccgcc tccgtcgtgt gcctgctgaa caacttctac 420
ccccgcgagg ccaaggtgca gtggaaggtg gacaacgccc tgcagtccgg caactcccaa 480
gagtccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtccagcc ccgtgaccaa gtccttcaac cggggcgagt gc 642

<210> SEQ ID NO 95
<211> LENGTH: 1341
<212> TYPE: DNA
<213> ORGANISM: Artificial
<220> FEATURE:
<223> OTHER INFORMATION: Polynucleotide sequence of 10.152 formatted as an IgG4 incorporating S228P

<400> SEQUENCE: 95
gaagtgcagc tggtgcagtc tggcgccgaa gtgaagaaac ccggcgctac cgtgaagatc 60
tcctgcaagg tgtccggcta caccttcacc gactccgtga tgaactgggt gcagcagcat 120
cccggcaagg gcctggaatg gatgggctgg atcgaccccg agtacggcag aaccgacgtg 180
gccgagaagt tccagggcag agtgaccatc accgccgaca cctccaccga caccgcctac 240
atggaactgt cctccctgcg gagcgaggac accgccgtgt actactgcgc ccggaccaag 300
tacaactccg gctacggctt cccctactgg ggccagggca ccaccgtgac cgtgtcctct 360
gcctccacca agggcccctc cgtgttccct ctggcccctt gctcccggtc cacctccgag 420
tctaccgccg ctctgggctg cctggtcaag gactacttcc ccgagcctgt gacagtgtcc 480
tggaactctg gcgccctgac ctccggcgtg cacaccttcc ctgccgtgct gcagtcctcc 540
ggcctgtact ccctgtcctc cgtcgtgacc gtgccttcca gctccctggg caccaagacc 600
tacacctgta acgtggacca caagccctcc aacaccaagg tggacaagcg ggtggaatct 660
aagtacggcc ctccctgccc cccctgccct gcccctgaat ttctgggcgg accttccgtg 720
ttcctgttcc ccccaaagcc caaggacacc ctgatgatct cccggacccc cgaagtgacc 780
tgcgtggtgg tggacgtgtc ccaagaggac cccgaggtgc agttcaattg gtacgtggac 840
ggcgtggaag tgcacaacgc caagaccaag cccagagagg aacagttcaa ctccacctac 900
cgggtggtgt ccgtgctgac cgtgctgcac caggactggc tgaacggcaa agaatacaag 960
tgcaaagtct ccaacaaggg cctgccctcc agcatcgaaa agaccatctc caaggccaag 1020

```
ggacagcccc gcgagcccca ggtgtacacc ctgcccccta gccaagagga aatgaccaag   1080

aaccaggtgt ccctgacctg cctcgtgaag ggcttctacc cctccgatat cgccgtggaa   1140

tgggagtcca acggccagcc cgagaacaac tacaagacca cccccctgt gctggactcc    1200

gacggctcct tcttcctgta ctctcggctg accgtggaca agtcccggtg gcaagagggc   1260

aacgtgttct cctgctccgt gatgcacgag gccctgcaca accactacac ccagaagtcc   1320

ctgtccctga gcctgggcaa g                                             1341
```

<210> SEQ ID NO 96
<211> LENGTH: 214
<212> TYPE: PRT
<213> ORGANISM: Artificial
<220> FEATURE:
<223> OTHER INFORMATION: Amino acid sequence of 10.152 light chain

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 97
<211> LENGTH: 642
<212> TYPE: DNA
<213> ORGANISM: Artificial
<220> FEATURE:
<223> OTHER INFORMATION: Polynucleotide sequence of 10.152 light chain

<400> SEQUENCE: 97

```
gacatccaga tgactcagag cccgtcctcg ctttcggctt ccgtcggcga ccgcgtgacc     60

atcacttgtc aggcgtcgca gaacgtcgat tccgacgtgg actggtacca acagaagccg    120
```

```
gggaaagcgc ccaagctgct gatctacaag gcctccaatg attacactgg agtgcctagc    180

cggttcagcg gatcagggtc gggaacggac ttcactttta ccatctcaag cctccaacca    240

gaagatattg ccacctatta ctgcgcacaa tcaaacaccc acccgagaac cttcggcgga    300

ggaaccaagg tggagatcaa acgtacggtg gcggcgccca gcgtgttcat cttcccaccc    360

agcgacgagc agctgaagtc cggcacagcc agcgtggtgt gcctgctgaa caacttctac    420

ccccgcgagg ccaaggtgca gtggaaggtg gacaacgccc tgcagagcgg caacagccag    480

gaaagcgtga ccgagcagga cagcaaggac tccacctaca gcctgagcag caccctgacc    540

ctgagcaagg ccgactacga gaagcacaag gtgtacgcct gcgaagtgac ccaccagggc    600

ctgtccagcc ccgtgaccaa gagcttcaac cggggcgagt gc                        642
```

```
<210> SEQ ID NO 98
<211> LENGTH: 666
<212> TYPE: DNA
<213> ORGANISM: Artificial
<220> FEATURE:
<223> OTHER INFORMATION: Polynucleotide sequence of 2.12 light chain

<400> SEQUENCE: 98

caggccgtgc tgacccagcc tgcctccctg tctgcctctc ctggcgagtc cgccagactg     60

acctgcaccc tgccctccga catcaacgtg cggtactaca acatctactg gtatcagcag    120

aagcccggca gcccccccag atacctgctg tactactact ccgactccca caagggccag    180

ggctccggcg tgccctccag attctccggc tccaaggacg tgtccaccaa ctccggcatc    240

ctgctgatct ccggcctgca gtccgaggac attgccacct actactgcat gacttggagc    300

agcaacggca gcggcgtgtt cggcggaggc acccagctga ccgtcctagg tcagcccaag    360

gccgctccca gcgtgaccct gttcccccca agcagcgagg aactgcaggc caacaaggcc    420

accctggtgt gcctgatcag cgacttctac cctggggccg tgaccgtggc ctggaaggcc    480

gatagcagcc ctgtgaaggc cggcgtggaa accaccaccc cctccaagca gagcaacaac    540

aaatacgccg ccagcagcta cctgtccctg acccccgagc agtggaagtc ccaccggtcc    600

tacagctgcc aggtgacaca cgagggcagc accgtggaaa agaccgtggc ccccaccgag    660

tgcagc                                                                666
```

```
<210> SEQ ID NO 99
<211> LENGTH: 642
<212> TYPE: DNA
<213> ORGANISM: Artificial
<220> FEATURE:
<223> OTHER INFORMATION: Polynucleotide sequence of Anti-CD138 kappa
      light chain

<400> SEQUENCE: 99

gacatccaga tgacccagag cacatcctct ctgagcgcct ccctgggcga tcgcgtgact     60

atcagttgca gcgcttccca agggattaac aattacctca actggtacca gcagaagccc    120

gacggaaccg tcgagctgct catctattac acatctacgc tgcaaagcgg cgtgccttcc    180

aggttctcag ggagcggttc cggaactgat tactctctga ccattagcaa tctcgaacca    240

gaagacatcg gcacatatta ctgtcagcag tactccaagc tgccccggac ttttggggga    300

ggcaccaaac tggagatcaa gcgtacggtg gcggcgccca gcgtgttcat cttcccaccc    360

agcgacgagc agctgaagtc cggcacagcc agcgtggtgt gcctgctgaa caacttctac    420

ccccgcgagg ccaaggtgca gtggaaggtg gacaacgccc tgcagagcgg caacagccag    480
```

gaaagcgtga ccgagcagga cagcaaggac tccacctaca gcctgagcag caccctgacc 540
ctgagcaagg ccgactacga gaagcacaag gtgtacgcct gcgaagtgac ccaccagggc 600
ctgtccagcc ccgtgaccaa gagcttcaac cggggcgagt gc 642

<210> SEQ ID NO 100
<211> LENGTH: 1347
<212> TYPE: DNA
<213> ORGANISM: Artificial
<220> FEATURE:
<223> OTHER INFORMATION: Polynucleotide sequence of Anti-CD138 IgG4 (S228P)

<400> SEQUENCE: 100
caggtgcagc tccaacagag cggctccgaa ctgatgatgc ctggggcctc tgtcaagatt 60
tcctgcaaag ctaccggcta cacattcagc aactattgga ttgagtgggt gaagcagcgc 120
ccagggcacg gtctggagtg gatcggagag atcctgccag gcaccgggag gactatttac 180
aatgaaaagt ttaaaggaaa ggccacattc accgcagaca tctctagcaa cactgttcaa 240
atgcagctct cctctctgac ctccgaggat agcgccgtgt attactgtgc tcggagagac 300
tactatggca atttttacta tgctatggat tactggggac agggcacatc tgtgaccgtc 360
agctccgcta gcaccaaggg ccccagcgtg ttccccctgg ccccttgtag cagaagcacc 420
agcgagagca cagccgccct gggctgcctg gtgaaagact acttccccga gcccgtcacc 480
gtgtcctgga acagcggagc cctgaccagc ggcgtgcaca cctttccagc cgtgctgcag 540
agcagcggcc tgtacagcct gagcagcgtg gtgacagtgc cctccagcag cctgggcacc 600
aagacctaca cctgtaacgt ggaccacaag cccagcaaca ccaaggtgga caagcgggtg 660
gaatctaagt acggcccacc ctgccccccc tgccctgccc ctgaatttct gggcggaccc 720
tccgtgttcc tgttcccccc aaagcccaag gacaccctga tgatcagccg gacccccgaa 780
gtgacctgcg tggtggtgga cgtgtcccag gaagatcccg aggtccagtt caattggtac 840
gtggacggcg tggaagtgca caacgccaag accaagccca gagaggaaca gttcaacagc 900
acctaccggg tggtgtccgt gctgaccgtg ctgcaccagg actggctgaa cggcaaagag 960
tacaagtgca aagtctccaa caagggcctg cccagctcca tcgagaaaac catcagcaag 1020
gccaagggcc agccccgcga gcctcaggtg tacacactgc cccccagcca ggaagagatg 1080
accaagaacc aggtgtccct gacctgtctg gtgaaaggct tctaccccag cgatatcgcc 1140
gtggaatggg agagcaacgg ccagcccgag aacaactaca agaccacccc ccctgtgctg 1200
gacagcgacg gcagcttctt cctgtactcc cggctgaccg tggacaagag ccggtggcag 1260
gaaggcaacg tcttcagctg cagcgtgatg cacgaggccc tgcacaacca ctacacccag 1320
aagtccctga gcctgagcct gggcaag 1347

<210> SEQ ID NO 101
<211> LENGTH: 1341
<212> TYPE: DNA
<213> ORGANISM: Artificial
<220> FEATURE:
<223> OTHER INFORMATION: Polynucleotide sequence of Anti-HLA IgG4 (S228P)

<400> SEQUENCE: 101
caggtccaac tcaagcagtc cggtccgggg ctggtccagc catctcaatc actgtctctt 60
acttgcaccg tgtccggatt cagcctgacc tcatacggag tgcattgggt gcggcagcct 120
cccgggaaag gactggagtg gctcggagtc atttggtccg gtggatcaac tgactacaat 180
gccgctttca tcagcaggct gagcattcgg aaggacaact ctaagagcca agtgttcttc 240
aagatgaact cactccaggc cgatgacacc gccatctact attgtgccag aaccttcacc 300
accagcacct ctgcatggtt tgcatactgg ggccagggca ctcttgtgac cgtgtcagct 360
gctagcacca agggccccag cgtgttcccc ctggcccctt gtagcagaag caccagcgag 420
agcacagccg ccctgggctg cctggtgaaa gactacttcc ccgagcccgt caccgtgtcc 480
tggaacagcg gagccctgac cagcggcgtg cacacctttc cagccgtgct gcagagcagc 540
ggcctgtaca gcctgagcag cgtggtgaca gtgccctcca gcagcctggg caccaagacc 600
tacacctgta acgtggacca caagcccagc aacaccaagg tggacaagcg ggtggaatct 660
aagtacggcc caccctgccc cccctgccct gcccctgaat ttctgggcgg accctccgtg 720
ttcctgttcc ccccaaagcc caaggacacc ctgatgatca gccggacccc cgaagtgacc 780
tgcgtggtgg tggacgtgtc ccaggaagat cccgaggtcc agttcaattg gtacgtggac 840
ggcgtggaag tgcacaacgc caagaccaag cccagagagg aacagttcaa cagcacctac 900
cgggtggtgt ccgtgctgac cgtgctgcac caggactggc tgaacggcaa agagtacaag 960
tgcaaagtct ccaacaaggg cctgcccagc tccatcgaga aaaccatcag caaggccaag 1020
ggccagcccc gcgagcctca ggtgtacaca ctgcccccca gccaggaaga gatgaccaag 1080
aaccaggtgt ccctgacctg tctggtgaaa ggcttctacc ccagcgatat cgccgtggaa 1140
tgggagagca acggccagcc cgagaacaac tacaagacca ccccccctgt gctggacagc 1200
gacggcagct tcttcctgta ctcccggctg accgtggaca agagccggtg gcaggaaggc 1260
aacgtcttca gctgcagcgt gatgcacgag gccctgcaca accactacac ccagaagtcc 1320
ctgagcctga gcctgggcaa g 1341

<210> SEQ ID NO 102
<211> LENGTH: 645
<212> TYPE: DNA
<213> ORGANISM: Artificial
<220> FEATURE:
<223> OTHER INFORMATION: Polynucleotide sequence of Anti-HLA VK

<400> SEQUENCE: 102
tctatcgtca tgacccagac cccgaagttc ctcctggtgt cagctggtga tcgggtgacc 60
atcacttgta aggcctctca gtctgtctca aacgacgtcg catggtacca acaaaagcct 120
gggcagtcac ctaagcttct gatctactat gcttccaatc gctacaccgg cgtgcccgac 180
aggttcaccg gatcagggta cggaaccgac ttcaccttta ctatttccac cgtgcaggcc 240
gaggacctcg ccgtgtattt ctgccagcaa gattacagca gcccaccctg gactttcggt 300
ggaggaacta aactggaaat tagacgtacg gtggcggcgc ccagcgtgtt catcttccca 360
cccagcgacg agcagctgaa gtccggcaca gccagcgtgg tgtgcctgct gaacaacttc 420
tacccccgcg aggccaaggt gcagtggaag gtggacaacg ccctgcagag cggcaacagc 480
caggaaagcg tgaccgagca ggacagcaag gactccacct acagcctgag cagcaccctg 540
accctgagca aggccgacta cgagaagcac aaggtgtacg cctgcgaagt gacccaccag 600
ggcctgtcca gccccgtgac caagagcttc aaccggggcg agtgc 645

<210> SEQ ID NO 103
<211> LENGTH: 1203
<212> TYPE: DNA
<213> ORGANISM: Artificial
<220> FEATURE:

<223> OTHER INFORMATION: Polynucleotide sequence of OPG-Fc

<400> SEQUENCE: 103
gaaacctttc cgccgaaata tctgcattat gatgaagaaa ccagccatca gctgctgtgc 60
gataaatgcc cgccgggcac ctatctgaaa cagcattgca ccgcgaaatg gaaaaccgtg 120
tgcgcgccgt gcccggatca ttattatacc gatagctggc ataccagcga tgaatgcctg 180
tattgcagcc cggtgtgcaa agaactgcag tatgtgaaac aggaatgcaa ccgcacccat 240
aaccgcgtgt gcgaatgcaa agaaggccgc tatctggaag gcgaattttg cctgaaacat 300
cgcagctgcc cgccgggctt tggcgtggtg caggcgggca ccccggaacg caacaccgtg 360
tgcaaacgct gcccggatgg ctttttttagc aacgaaacca gcagcaaagc gccgtgccgc 420
aaacatacca actgcagcgt gtttggcctg ctgctgaccc agaaaggcaa cgcgacccat 480
gataacattt gcagcggcaa cagcgaaagc acccagaaag aacgcaaatg ctgcgtggaa 540
tgcccgccgt gcccggcgcc gccggtggcg ggcccgagcg tgtttctgtt tccgccgaaa 600
ccgaaagata ccctgatgat tagccgcacc ccggaagtga cctgcgtggt ggtggatgtg 660
agccatgaag atccggaagt gcagtttaac tggtatgtgg atggcgtgga agtgcataac 720
gcgaaaacca aaccgcgcga agaacagttt aacagcacct ttcgcgtggt gagcgtgctg 780
accgtggtgc atcaggattg gctgaacggc aaagaatata aatgcaaagt gagcaacaaa 840
ggcctgccgg cgccgattga aaaaaccatt agcaaaacca aaggccagcc gcgcgaaccg 900
caggtgtata ccctgccgcc gagccgcgaa gaaatgacca aaaaccaggt gagcctgacc 960
tgcctggtga aaggctttta tccgagcgat attgcggtgg aatgggaaag caacggccag 1020
ccggaaaaca actataaaac caccccgccg atgctggata gcgatggcag cttttttctg 1080
tatagcaaac tgaccgtgga taaaagccgc tggcagcagg gcaacgtgtt tagctgcagc 1140
gtgatgcatg aagcgctgca taaccattat acccagaaaa gcctgagcct gagcccgggc 1200
aaa 1203

<210> SEQ ID NO 104
<211> LENGTH: 1350
<212> TYPE: DNA
<213> ORGANISM: Artificial
<220> FEATURE:
<223> OTHER INFORMATION: Polynucleotide sequence of 10.21 formatted as
an IgG1

<400> SEQUENCE: 104
gaagtgcagc tggtgcagtc tggcgccgaa gtgaagaaac ctggcgccac cgtgaagatc 60
agctgcaagg tgtccggcta caccttcacc gacagcgtga tgaactgggt gcagcaggcc 120
cctggcaagg gcctggaatg gatgggatgg atcgaccccg agtacggcag aaccgacgtg 180
gccgagaagt tccagggcag agtgaccatc accgccgaca ccagcaccga caccgcctac 240
atggaactga gcagcctgcg gagcgaggac accgccgtgt actactgtgc ccggaccaag 300
tacaacagcg gctacggctt cccctactgg ggccagggca caaccgtgac agtgtcctca 360
gctagcacca agggacccag cgtgttccct ctggccccta gcagcaagag cacatctggc 420
ggaacagccg ccctgggctg cctcgtgaag gactactttc ccgagcctgt caccgtgtct 480
tggaactctg gcgccctgac aagcggcgtg cacacctttc cagccgtgct gcagagcagc 540
ggcctgtact ctctgagcag cgtcgtgaca gtgcccagct ctagcctggg cacccagacc 600
tacatctgca acgtgaacca caagcccagc aacaccaagg tggacaagaa ggtggaaccc 660
aagagctgcg acaagaccca cacctgtccc ccttgtcctg cccccgaact gctgggaggc 720
ccttccgtgt tcctgttccc cccaaagccc aaggacaccc tgatgatcag ccggaccccc 780
gaagtgacct gcgtggtggt ggatgtgtcc cacgaggacc ctgaagtgaa gttcaattgg 840
tacgtggacg gcgtggaagt gcacaacgcc aagaccaagc ccagagagga acagtacaac 900
agcacctacc gggtggtgtc cgtgctgaca gtgctgcacc aggactggct gaacggcaaa 960
gagtacaagt gcaaggtgtc caacaaggcc ctgcctgccc ccatcgagaa aaccatcagc 1020
aaggccaagg gccagccccg cgaaccccag gtgtacacac tgcccccaag cagggacgag 1080
ctgaccaaga accaggtgtc cctgacctgt ctcgtgaaag gcttctaccc ctccgatatc 1140
gccgtggaat gggagagcaa cggccagccc gagaacaact acaagaccac ccccccgtg 1200 ctggacagcg acggctcatt cttcctgtac agcaagctga ccgtggacaa gtcccggtgg 1260
cagcagggca acgtgttcag ctgcagcgtg atgcacgagg ccctgcacaa ccactacacc 1320
cagaagtccc tgagcctgag ccccggcaag 1350

<210> SEQ ID NO 105
<211> LENGTH: 1338
<212> TYPE: DNA
<213> ORGANISM: Artificial
<220> FEATURE:
<223> OTHER INFORMATION: Polynucleotide sequence of 10.21 IgG2

<400> SEQUENCE: 105
gaagtgcagc tggtgcagtc tggcgccgaa gtgaagaaac ctggcgccac cgtgaagatc 60
agctgcaagg tgtccggcta caccttcacc gacagcgtga tgaactgggt gcagcaggcc 120
cctggcaagg gcctggaatg gatgggatgg atcgaccccg agtacggcag aaccgacgtg 180
gccgagaagt tccagggcag agtgaccatc accgccgaca ccagcaccga caccgcctac 240
atggaactga gcagcctgcg gagcgaggac accgccgtgt actactgtgc ccggaccaag 300
tacaacagcg gctacggctt cccctactgg ggccagggca caaccgtgac agtgtcctca 360
gccagcacca agggccccag cgtgttcccc ctggcccccct gcagcagaag caccagcgag 420
agcacagccg ccctgggctg cctggtgaag gactacttcc ccgagcccgt gacagtgagc 480
tggaacagcg gagccctgac ctccggtgta cacaccttcc ccgccgtgct gcagagcagc 540
ggcctgtact ccctgagcag cgtggtgacc gtgcccagca gcaacttcgg cacccagacc 600
tacacctgca acgtggacca caagcccagc aacaccaagg tggacaagac cgtggagagg 660
aagtgctgcg tggagtgccc cccctgccca gcccccccag tggccggacc ctccgtgttt 720
ctgttccccc ccaagcccaa ggacaccctg atgatcagca ggacccccga ggtgacctgc 780
gtggtggtgg acgtgagcca cgaggatccg gaggtgcagt tcaactggta cgtggacggc 840
gtggaggtgc acaacgccaa gaccaagccc agagaggagc agtttaacag caccttcagg 900
gtggtgtccg tgctgaccgt ggtgcaccag gactggctga acggcaagga atacaagtgc 960
aaggtctcca acaagggcct gccagccccc atcgagaaaa ccatcagcaa gaccaagggc 1020
cagccacggg agccccaagt gtataccctg cccccccagcc gggaggagat gaccaagaac 1080
caggtgtccc tgacctgtct ggtgaagggc ttctacccca gcgacatcgc cgtggagtgg 1140
gagagcaacg gccagcccga gaacaactac aagaccaccc cccccatgct ggacagcgac 1200
ggcagcttct tcctgtactc caagctgaca gtggacaagt ccaggtggca gcagggcaac 1260
gtgttcagct gcagcgtgat gcacgaggcc ctgcacaacc actacaccca gaagagcctg 1320
agcctgtccc ccggcaag 1338

<210> SEQ ID NO 106
<211> LENGTH: 1491
<212> TYPE: DNA
<213> ORGANISM: Artificial
<220> FEATURE:
<223> OTHER INFORMATION: Polynucleotide sequence of 10.21 IgG3

<400> SEQUENCE: 106
gaagtgcagc tggtgcagtc tggcgccgaa gtgaagaaac ctggcgccac cgtgaagatc 60
agctgcaagg tgtccggcta caccttcacc gacagcgtga tgaactgggt gcagcaggcc 120
cctggcaagg gcctggaatg gatgggatgg atcgaccccg agtacggcag aaccgacgtg 180
gccgagaagt tccagggcag agtgaccatc accgccgaca ccagcaccga caccgcctac 240
atggaactga gcagcctgcg gagcgaggac accgccgtgt actactgtgc ccggaccaag 300
tacaacagcg gctacggctt cccctactgg ggccagggca caaccgtgac agtgtcctca 360
gcgagcacca aaggcccgag cgtgtttccg ctggcgccgt gcagccgcag caccagcggc 420
ggcaccgcgg cgctgggctg cctggtgaaa gattattttc cggaaccggt gaccgtgagc 480
tggaacagcg gcgcgctgac cagcggcgtg catacctttc cggcggtgct gcagagcagc 540
ggcctgtata gcctgagcag cgtggtgacc gtgccgagca gcagcctggg cacccagacc 600
tatacctgca acgtgaacca taaaccgagc aacaccaaag tggataaacg cgtggaactg 660
aaaaccccgc tgggcgatac cacccatacc tgcccgcgct gcccggaacc gaaaagctgc 720
gataccccgc cgccgtgccc gcgctgcccg gaaccgaaaa gctgcgatac cccgccgccg 780
tgcccgcgct gcccggaacc gaaaagctgc gataccccgc cgccgtgccc gcgctgcccg 840
gcgccggaac tgctgggcgg cccgagcgtg tttctgtttc cgccgaaacc gaaagatacc 900
ctgatgatta gccgcacccc ggaagtgacc tgcgtggtgg tggatgtgag ccatgaagat 960
ccggaagtgc agtttaaatg gtatgtggat ggcgtggaag tgcataacgc gaaaaccaaa 1020
ccgcgcgaag aacagtttaa cagcaccttt cgcgtggtga gcgtgctgac cgtgctgcat 1080
caggattggc tgaacggcaa agaatataaa tgcaaagtga gcaacaaagc gctgccggcg 1140
ccgattgaaa aaaccattag caaaaccaaa ggccagccgc gcgaaccgca ggtgtatacc 1200
ctgccgccga gccgcgaaga aatgaccaaa aaccaggtga gcctgacctg cctggtgaaa 1260
ggcttttatc cgagcgatat tgcggtggaa tgggaaagca gcggccagcc ggaaaacaac 1320
tataacacca ccccgccgat gctggatagc gatggcagct tttttctgta tagcaaactg 1380
accgtggata aaagccgctg gcagcagggc aacattttta gctgcagcgt gatgcatgaa 1440
gcgctgcata accgctttac ccagaaaagc ctgagcctga gcccgggcaa a 1491

<210> SEQ ID NO 107
<211> LENGTH: 165
<212> TYPE: PRT
<213> ORGANISM: Artificial
<220> FEATURE:
<223> OTHER INFORMATION: Glycosylated (T106T) human interferon alpha-2-b comprising attenuating mutation A145X where X can be any amino acid selected from D, E, G, H, I, K, L, M, N, Q, R, S, T, V, Y
<220> FEATURE:
<221> NAME/KEY: VARIANT
<222> LOCATION: (145)..(145)
<223> OTHER INFORMATION: Xaa can be any amino acid selected from D, E, G, H, I, K, L, M, N, Q, R, S, T, V, Y

<400> SEQUENCE: 107

Cys Asp Leu Pro Gln Thr His Ser Leu Gly Ser Arg Arg Thr Leu Met

-continued

```
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Xaa Glu Ile Met Arg Ser Phe Ser Leu Ser Thr Asn Leu Gln Glu Ser
145                 150                 155                 160

Leu Arg Ser Lys Glu
                165


<210> SEQ ID NO 108
<211> LENGTH: 165
<212> TYPE: PRT
<213> ORGANISM: Artificial
<220> FEATURE:
<223> OTHER INFORMATION: Glycosylated (T106T) human interferon alpha-2-b
      comprising attenuating mutation R144X where X can be any amino
      acid selected from A, D, E, G, H, I, K, L, N, Q, S, T, V, Y
<220> FEATURE:
<221> NAME/KEY: VARIANT
<222> LOCATION: (144)..(144)
<223> OTHER INFORMATION: Xaa can be any amino acid selected from A, D,
      E, G, H, I, K, L, N, Q, S, T, V, Y

<400> SEQUENCE: 108

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Xaa
    130                 135                 140

Ala Glu Ile Met Arg Ser Phe Ser Leu Ser Thr Asn Leu Gln Glu Ser
145                 150                 155                 160
```

```
Leu Arg Ser Lys Glu
                165


<210> SEQ ID NO 109
<211> LENGTH: 165
<212> TYPE: PRT
<213> ORGANISM: Artificial
<220> FEATURE:
<223> OTHER INFORMATION: Glycosylated (T106T) human interferon alpha-2-b
      comprising attenuating mutation R33X, where X can be any amino
      acid selected from K, A, Q
<220> FEATURE:
<221> NAME/KEY: VARIANT
<222> LOCATION: (33)..(33)
<223> OTHER INFORMATION: Xaa can be any amino acid selected from K, A, Q

<400> SEQUENCE: 109

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Xaa His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 110
<211> LENGTH: 164
<212> TYPE: PRT
<213> ORGANISM: Artificial
<220> FEATURE:
<223> OTHER INFORMATION: Human interferon alpha-2-b comprising with
      deletion of amino acid at position 106 and comprising attenuating
      mutation A144X where X, can be any amino acid selected from D, E,
      G, H, I, K, L, M, N, Q, R, S, T, V, Y
<220> FEATURE:
<221> NAME/KEY: VARIANT
<222> LOCATION: (144)..(144)
<223> OTHER INFORMATION: Xaa can be any amino acid selected from D, E,
      G, H, I, K, L, M, N, Q, R, S, T, V, Y

<400> SEQUENCE: 110

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45
```

```
Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Glu Thr Pro Leu Met Lys Glu
            100                 105                 110

Asp Ser Ile Leu Ala Val Arg Lys Tyr Phe Gln Arg Ile Thr Leu Tyr
        115                 120                 125

Leu Lys Glu Lys Lys Tyr Ser Pro Cys Ala Trp Glu Val Val Arg Xaa
    130                 135                 140

Glu Ile Met Arg Ser Phe Ser Leu Ser Thr Asn Leu Gln Glu Ser Leu
145                 150                 155                 160

Arg Ser Lys Glu


<210> SEQ ID NO 111
<211> LENGTH: 450
<212> TYPE: PRT
<213> ORGANISM: Artificial
<220> FEATURE:
<223> OTHER INFORMATION: VH sequence of 10.21 formatted as an IgG1
      incorporating substitutions M255Y, S257T, T259E

<400> SEQUENCE: 111

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 112
<211> LENGTH: 446
<212> TYPE: PRT
<213> ORGANISM: Artificial
<220> FEATURE:
<223> OTHER INFORMATION: VH sequence of 10.21 formatted onto an IgG2
      backbone incorporating substitutions A330S and P331S

<400> SEQUENCE: 112

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```